United States Patent [19]
Korneluk et al.

[11] Patent Number: 6,156,535
[45] Date of Patent: Dec. 5, 2000

[54] MAMMALIAN IAP GENE FAMILY, PRIMERS, PROBES, AND DETECTION METHODS

[75] Inventors: Robert G. Korneluk; Alexander E. MacKenzie; Stephen Baird; Peter Liston, all of Ottawa, Canada

[73] Assignee: University of Ottawa, Ottawa, Canada

[21] Appl. No.: 08/576,956

[22] Filed: Dec. 22, 1995

Related U.S. Application Data

[63] Continuation-in-part of application No. 08/511,485, Aug. 4, 1995, Pat. No. 5,919,912.

[51] Int. Cl.[7] .............................. C12N 15/12; C12P 21/00
[52] U.S. Cl. ......................................... 435/69.1; 536/23.5
[58] Field of Search ................................. 536/23.1, 23.5; 435/6, 69.1

[56] References Cited

FOREIGN PATENT DOCUMENTS

| WO 94/06814 | 3/1994 | WIPO . |
| WO 95/19431 | 7/1995 | WIPO . |
| WO 95/28497 | 10/1995 | WIPO . |

OTHER PUBLICATIONS

Liston et al., "Suppression of apoptosis in mammalian cells by NAIP and a related family of IAP genes", *Nature,* 379: 349–353, (1996).
Duckett et al., "A conserved family of cellular genes related to the baculovirus iap gene and encoding apoptosis inhibitors", *The EMBO Journal,* 15: 2685–2694, (1996).
Clem et al., "Anti–apoptotic genes of baculovirus", *Cell Death and Differentiation,* 3: 9–16, (1996).
Rothe et al., "The TNFR2–TRAF Signaling Complex Contains Two Novel Proteins Related to Baculoviral Inhibitor of Apoptosis Proteins", *Cell,* 83: 1243–1252, (1995).
Hillier, L., et al., Mar. 27, 1995, GenBank Accession No. T96284.
H. Steller, "Mechanisms and Genes of Cellular Suicide", Science 267:1445, 1995.
Williams et al., "Apoptosis: final control point in cell biology", Trends in Cell Biology 2:263, 1992.
S. Korsmeyer, "Regulators of cell death", TIG 11:101, 1995.
Birnbaum et al, "An apoptosis–inhibiting gene from a nuclear polyhedrosis virus encoding a polypeptide with Cys/His sequence motifs", J. of Virol. 68:2521, 1994.
Crook et al., "An apoptosis–inhibiting baculovirus gene with a zinc finger–like motif", J. of Virol. 67:2168, 1993.
A. Wyllie, "Death gets a brake", Naature 369:272, 1994.
Clem et al., "Control of programmed cell death by the baculovirus genes p35 and iap", Mol. and Cell. Biology 14:5212, 1994.
Clem et al., "Prevention of apoptosis by a baculovirus gene during infection of insect cells", Science 254:1388, 1991.
Nunez et al., "The Bcl–2 family of proteins: regulators of cell death and survival", Trends in Cell Biology 4:399, 1994.
Golstein et al., "Homology between reaper and the cell death domains of Fas and TNFR1", Cell 81:185, 1995.

Clem et al., "Induction and inhibition of apoptosis by insect viruses", *Apoptosis II: The Molecular Basis of Apoptosis in Disease,* Cold Spring Harbor Laboratory Press, p. 89, 1994.
J. Kerr, "Neglected opportunities in apoptosis research", Trends in Cell Biology 5:55, 1995.
Roy et al., "The gene for neuronal apoptosis inhibitory protein is partially deleted in individuals with spinal muscular atrophy", Cell 80:167, 1995.
Osborne et al., "Essential genes that regulate apoptosis", Trends in Cell Biology 4:394, 1994.
White et al., "Genetic control of programmed cell death in drosophila", Science 264:677, 1994.
Fisher et al., "Dominant interfering Fas gene mutations impair apoptosis in a human autoimmune lymphoproliferative syndrome", Cell 81:935, 1995.
Rieux–Laucat et al., "Mutations in Fas associated with human lymphoproliferative syndrome and autoimmunity", Science 268:1347, 1995.
Katsikis et al., "Fas antigen stimulation induces marked apoptosis of T lymphocytes in human immunodeficiency virus–infected individuals", Abstract, J. Exp. Med. 1815:2029, 1995.
Muro–Cacho et al., "Analysis of apoptosis in lymph nodes of HIV–infected persons . . . ", Abstract, J. Immunol. 154:5555, 1995.
Li et al., "Induction of apoptosis in uninfected lymphocytes by HIV–1 Tat protein", Abstract, Science 268:429, 1995.
Westendorp et al., "Sensitization of T cells to CD95–mediated apoptosis by HIV–1 Tat and gp120", Nature 375:497, 1995.
Walkinshaw et al., "Induction of apoptosis in catecholaminergic PC12 cells by L–DOPA . . . ", Abstract, J. Clin. Invest. 95::2458, 1995.
Gibellini et al., "Tat–expression Jurkat cells show an increased resistance to different apoptic stimuli . . . " Abstract, Br. J. Haematol 89:24, 1995.
Martin et al., "HIV–1 infection of human CD4+ T cells in vitro . . . ", Abstract, J. Immunol. 152:330, 1994.
Terai et al., "Apoptosis as a mechanism of cell death in cultured T lymphoblasts acutely infected with HIV–1" Abstract, J. Clin. Invest 87:1710, 1991.
Dhein et al., "Autocrine T–cells suicide mediated by APO–1(Fas/CD95)", Abstract, Nature 373:438, 1995.
Vossbeck et al., "Direct transforming activity of TGF–beta on rat fibroblasts", Abstract, Int. J. Cancer 61:92, 1995.

(List continued on next page.)

*Primary Examiner*—Robert A. Schwartzman
*Attorney, Agent, or Firm*—Clark & Elbing LLP; Kristina Bieker Brady

[57] ABSTRACT

Disclosed is substantially pure DNA encoding mammalian IAP polypeptides; substantially pure polypeptides; and methods of using such DNA to express the IAP polypeptides in cells and animals to inhibit apoptosis. Also disclosed are conserved regions characteristic of the IAP family and primers and probes for the identification and isolation of additional IAP genes. In addition, methods for treating diseases and disorders involving apoptosis are provided.

15 Claims, 53 Drawing Sheets

OTHER PUBLICATIONS

Goruppi et al., "Dissection of c–myc domains involved in S phase induction of NIH3T3 fibroblasts", Abstract, Oncogene 9:1537, 1994.

Fernandez et al., "Differential sensitivity of normal and Ha–ras–transformed C3H mouse embryo fibroblasts to tumor necrosis factor: . . . ", Abstract, Oncogene 9:2009, 1994.

Harrington et al., "c–Myc–induced apoptosis in fibroblasts is inherited by specific cytokines", Abstract, EMBO J. 13:3286, 1994.

Itoh et al., "A novel protein required for apoptosis . . . ", Abstract, J. Biol. Chem. 268:10932, 1993.

Melino et al., "Tissue transglutaminase and apoptosis: sense and antisense transfection studies . . . " Abstract, Mol. Cell. Biol. 14:6584, 1994.

Rosenbaum et al., "Evidence for hypoxia–induced, programmed cell death of cultured neurons", Abstract, Ann. Neurol. 36:864, 1994.

Sato et al., "Neuronal differentiation of PC12 cells as a result of prevention of cell death by bcl–2", Abstract, J. Neurobiol. 25:1227, 1994.

Ferrari et al., "N–acetylcysteine (D– and L–stereoisomers) prevents apoptotic death of neuronal cells", Abstract, J. Neurosci. 1516:2857, 1995.

Talley et al., "Tumor necrosis factor alpha–induced apoptosis in human neuronal cells: . . . ", Abstract, Mol. Cell. Biol. 1585:2359, 1995.

Rabizadeh et al., "Expression of the baculovirus p35 gene inhibits mammalian neural cell death", Abstract, J. Neurochem. 61:2318, 1993.

Birnbaum et al., "An apoptosis–inhibiting gene from a nuclear polyhedrosis virus encoding a polypeptide with Cys/His sequence motifs", Abstract, J. Virol. 68:2521, 1994.

HUMAN xiap

```
     1 gaaaggtgtggacaagtcctaattcaagagagatgactttaacagttttgaaggatct  60
                                       M  T  F  N  S  F  E  G  S 61 aaaacttgtgtacctgcagacatcaataaggaagaagaatttgtagaagagtttaataga 120
       K  T  C  V  P  A  D  I  N  K  E  E  F  V  E  E  F  N  R 121 ttaaaaacttttgctaattttccaagtggtagtcctgtttcagcatcaacactggcacga 180
       L  K  T  F  A  N  F  P  S  G  S  P  V  S  A  S  T  L  A  R 181 gcagggtttctttatactggtgaaggagataccgtgcggtgcttagttgtcatgcagct 240
       A  G  F  L  Y  T  G  E  G  D  T  V  R  C  F  S  C  H  A  A 241 gtagatagatggcaatatggagactcagcagtggaagacacaggaaagtatccccaaat 300
       V  D  R  W  Q  Y  G  D  S  A  V  G  R  H  R  K  V  S  P  N 301 tgcagatttatcaacggcttttatcttgaaaatagtgccacgcagtctacaaattctggt 360
       C  R  F  I  N  G  F  Y  L  E  N  S  A  T  Q  S  T  N  S  G
```

SEQ ID NO:3
SEQ ID NO:4

Fig. 1 (page 1 of 7)

HUMAN xiap

```
      atccagaatggtcagtacaaagttgaaactatctgggaagcagagatcatttgccta
361   ------+---------+---------+---------+---------+---------+  420
       I  Q  N  G  Q  Y  K  V  E  N  Y  L  G  S  R  D  H  F  A  L gacaggccatctgagacacatgcagactacctatctttgagaactgggcaggttgtagatata
421   ------+---------+---------+---------+---------+---------+  480
       D  R  P  S  E  T  H  A  D  Y  L  L  R  T  G  Q  V  V  D  I tcagacaccatataccgaggaacctgccatgtattgtgaagaagctagattaaagtcc
481   ------+---------+---------+---------+---------+---------+  540
       S  D  T  I  Y  P  R  N  P  A  M  Y  C  E  E  A  R  L  K  S tttcagaactgccagactatgctcacctaaccccaagagagttagcaagtgctggactc
541   ------+---------+---------+---------+---------+---------+  600
       F  Q  N  W  P  D  Y  A  H  L  T  P  R  E  L  A  S  A  G  L tactacacaggtattggtgaccaagtgcagtgcttttgtgtggaaaactgaaaaat
601   ------+---------+---------+---------+---------+---------+  660
       Y  Y  T  G  I  G  D  Q  V  Q  C  F  C  C  G  G  K  L  K  N tgggaacctttgtgatcgtgcctggtcagaacacaggcgacacttcctaattgcttcttt
661   ------+---------+---------+---------+---------+---------+  720
       W  E  P  C  D  R  A  W  S  E  H  R  R  H  F  P  N  C  F  F
```

Fig. 1 (page 2 of 7)

HUMAN xiap

```
721  gttttgggccggaatcttaatattcgaagtgaattcgatgctgtgagttctgataggaat  780
     ---------+---------+---------+---------+---------+---------+
 a    V  L  G  R  N  L  N  I  R  S  E  S  D  A  V  S  S  D  R  N 781  ttcccaaattcaacaaatcttccaagaaatccatggcagattatgaagcacggatc  840
     ---------+---------+---------+---------+---------+---------+
 a    F  P  N  S  T  N  L  P  R  N  P  S  M  A  D  Y  E  A  R  I 841  tttacttttgggacatggatatactcagttaacaaggagcagcttgcaagagctggattt  900
     ---------+---------+---------+---------+---------+---------+
 a    F  T  F  G  T  W  I  Y  S  V  N  K  E  Q  L  A  R  A  G  F 901  tatgctttaggtgaaggtgataaagtgctttcactgtggaggggctaactgat  960
     ---------+---------+---------+---------+---------+---------+
 a    Y  A  L  G  E  G  D  K  V  K  C  F  H  C  G  G  G  L  T  D 961  tggaagcccagtgaagaccctgggaacacatgctaaatggtatccaggggtgcaaatat  1020
     ---------+---------+---------+---------+---------+---------+
 a    W  K  P  S  E  D  P  W  E  Q  H  A  K  W  Y  P  G  C  K  Y 1021 ctgttagaacagaagggacaagaatataacaatattcattaactcattcacttgag  1080
     ---------+---------+---------+---------+---------+---------+
 a    L  L  E  Q  K  G  Q  E  Y  I  N  N  I  H  L  T  H  S  L  E
```

Fig. 1 (page 3 of 7)

HUMAN xiap

```
1081   gagtgtctggtaagaactactgagaaacaccatcactaactagaagaattgatgatacc  1140
       ---------+---------+---------+---------+---------+---------+
    a  E   C   L   V   R   T   T   E   K   T   P   S   L   T   R   R   I   D   D   T 1141   atcttccaaaatccctatggtacaagaagctatacgaatggggttcagtttcaaggacatt  1200
       ---------+---------+---------+---------+---------+---------+
    a  I   F   Q   N   P   M   V   Q   E   A   I   R   M   G   F   S   F   K   D   I 1201   aagaaaataatggaggaaaaattcagatatctgggagcaactataaatcacttgaggtt  1260
       ---------+---------+---------+---------+---------+---------+
    a  K   K   I   M   E   E   K   I   Q   I   S   G   S   N   Y   K   S   L   E   V 1261   ctggttgcagatctagtgaatgctcagaaagacagtatgcaagatgagtcaagtcagact  1320
       ---------+---------+---------+---------+---------+---------+
    a  L   V   A   D   L   V   N   A   Q   K   D   S   M   Q   D   E   S   S   Q   T 1321   tcattacagaaagagattagtactgaagagcagctaaggcgcctgcaagaggagaagctt  1380
       ---------+---------+---------+---------+---------+---------+
    a  S   L   Q   K   E   I   S   T   E   E   Q   L   R   R   L   Q   E   E   K   L 1381   tgcaaaatctgtatggatagaaatattgctatcgttttgttccttgtggacatctagtc  1440
       ---------+---------+---------+---------+---------+---------+
```

Fig. 1 (page 4 of 7)

HUMAN xiap

```
       C  K  I  C  M  D  R  N  I  A  I  V  F  V  P  C  G  H  L  V
1441   acttgtaaacaatgtgctgaagcagttgacaagtgtcccatgtgctacacagtcattact   1500
       T  C  K  Q  C  A  E  A  V  D  K  C  P  M  C  Y  T  V  I  T
1501   ttcaagcaaaaatttttatgtcttaactctatagtaggcatgttatgttgttct         1560
       F  K  Q  K  I  F  M  S  *
1561   tattaccctgattgaatgtgtgatgtgaactgactttaagtaatcaggattgaattccat   1620
1621   tagcatttgctaccaagtaggaaaaaaatgtacatgcagtgttttagttggcaatata    1680
1681   atctttgaatttcttgattttcagggtattagctgtattatccatttttttactgtta    1740
1741   tttaattgaaaccatagactaagaataagaagcatcatactataactgaacacaatgtgt   1800
```

Fig. 1 (page 5 of 7)

HUMAN xiap

```
1801  attcatagtatactgatttaattctaagtgtaagtgaattaatcatctgatttttat  1860
      ----+----+----+----+----+----+----+----+----+----+----+----+
   a 1861  tcttttcagataggcttaacaaatggagctttctgtatataaatgtggagattagagtta  1920
      ----+----+----+----+----+----+----+----+----+----+----+----+
   a 1921  atctccccaatcacataatttgttttgtgtgaaaaaggaataaaattgttccatgctggtg  1980
      ----+----+----+----+----+----+----+----+----+----+----+----+
   a 1981  gaaagatagagagattgttttagaggttgttgtgtgttttaggattctgtgtccatttct  2040
      ----+----+----+----+----+----+----+----+----+----+----+----+
   a 2041  tgtaaagnnataaacacgnacntgtgcgaaatatnttgtaaagtgatttgccattnttg  2100
      ----+----+----+----+----+----+----+----+----+----+----+----+
   a 2101  aaagcgtatttaatgatagaatactatcgagccaacatgtactgacacatggaaagatgtca  2160
      ----+----+----+----+----+----+----+----+----+----+----+----+
   a
```

Fig. 1 (page 6 of 7)

HUMAN xiap

```
2161 nagatatgttaagtgtaaaatgcaagtggcnnnacactatgtatagtctgagccagatca 2220
     ------+---------+---------+---------+---------+---------+
   a 2221 aagtatgtatgttnttaatatgcatagaacnanagatttggaaagatatacaccaaactg 2280
     ------+---------+---------+---------+---------+---------+
   a 2281 ttaaatgtggtttctctcttcggggagggggattggggagggcccagaggggtttta 2340
     ------+---------+---------+---------+---------+---------+
   a 2341 nagggggcctttcactttcnacttttcattttgttctgttcgnattttttataagtat 2400
     ------+---------+---------+---------+---------+---------+
   a 2401 gtanaccccnaagggttttatgnaactaacatcagtaacctaaccccgtgactatcct 2460
     ------+---------+---------+---------+---------+---------+
   a 2461 gtnctctttcctaggagctgtntgtttccaccaccaccccttccctctgaacaaatgc 2520
     ------+---------+---------+---------+---------+---------+
   a 2521 ctgagtgtgctggggcactttn 2540
     ------+---------+
   a
```

Fig. 1 (page 7 of 7)

HUMAN hiap-1

```
SEQ ID NO:5
         1  TCCTTGAGATGTATCAGTATATAGGATTTAGGATCTCCATGTTGGAACTCTAAATGCATAGA   60
                                                                           c
        61  AATGGAAATAATGGAAATTTTTCATTTTGGCTTTTTCAGCCTAGTATTAAAACTGATAAAA  120
                                                                           c
       121  GCAAAGCCATGCACAAAACTACCTCCCTAGAGAAAGGCTAGTCCCTTTTCTTCCCCATTC   180
                                                                           c
       181  ATTTCATTATGAACATAGTAGAAAAACAGCATATATTCTTATCAAATTTGATGAAAAGCGCCA  240
                 M  N  I  V  E  N  S  I  F  L  S  N  L  M  K  S  A  N  -
SEQ ID NO:6 c
       241  ACACGTTTGAACTGAAATACGACTTGTCATGTGAACTGTACCGAATGTCTACGTATTCCA   300
              T  F  E  L  K  Y  D  L  S  C  E  L  Y  R  M  S  T  Y  S  T  -
            c
       301  CTTTTCCTGCTGGGGGTTCCTGTCTCAGAAAGGAGTCTTGCTCGTGCTGGTTTCTATTACA   360
              F  P  A  G  V  P  V  S  E  R  S  L  A  R  A  G  F  Y  Y  T  -
            c
```

Fig. 2 (page 1 of 8)

HUMAN hiap-1

```
       CTGGTGTGAATGACAAGGTCAAATGCTTCTGTTGTGGCCTGATGCTGGATAACTGGAAAA
361    ------+---------+---------+---------+---------+---------+ 420
    c    G  V  N  D  K  V  K  C  F  C  C  G  L  M  L  D  N  W  K  R  -

GAGGAGACAGTCCTACTGAAAAGCATAAAAAGTTGTATCCTAGCTGCAGATTCGTTCAGA
421    ------+---------+---------+---------+---------+---------+ 480
    c    G  D  S  P  T  E  K  H  K  K  L  Y  P  S  C  R  F  V  Q  -

GTCTAAATTCCGTTAACAACTTGGAAGCTACCTCTCAGCCTACTTTTCCTTCTTCAGTAA
481    ------+---------+---------+---------+---------+---------+ 540
    c    S  L  N  S  V  N  N  L  E  A  T  S  Q  P  T  F  P  S  S  V  T  -

CACATTCCACACACTCATTACTTCCGGGTACAGAAAACAGTGGATATTCCGTGGCTCTT
541    ------+---------+---------+---------+---------+---------+ 600
    c    H  S  T  H  S  L  L  P  G  T  E  N  S  G  Y  F  R  G  S  Y  -

ATTCAAACTCTCCATCAAATCCTGTAAAACTCCAGAGCAAATCAAGAATTTTCTGCCTTGA
601    ------+---------+---------+---------+---------+---------+ 660
    c    S  N  P  S  N  P  V  N  S  R  A  N  Q  E  F  S  A  L  M  -

TGAGAAGTTCCTACCCCTGTCCAATGAATAACGAAAATGCCAGATTACTTACTTTTCAGA
661    ------+---------+---------+---------+---------+---------+ 720
    c    R  S  S  Y  P  C  P  M  N  N  E  N  A  R  L  L  T  F  Q  T  -
```

Fig. 2 (page 2 of 8)

HUMAN hiap-1

```
      CATGGCCATTGACTTTTCTGTGCGCCAACAGATCTGGCACGAGCAGGCTTTTACTACATAG
721   ------------------------------------------------------------ + 780
       W  P  L  T  F  L  S  P  T  D  L  A  R  A  G  F  Y  Y  I  G  -

GACCTGGAGACAGAGTGGCTTGCTTTGCCTGTGGTGGAAAATTGAGCAATTGGGAACCGA
781   ------------------------------------------------------------ + 840
       P  G  D  R  V  A  C  F  A  C  G  G  K  L  S  N  W  E  P  K  -

AGGATAAATGCTATGTCAGAACACCTGAGACATTTTCCCAAATGCCCATTTATAGAAAATC
841   ------------------------------------------------------------ + 900
       D  N  A  M  S  E  H  L  R  H  F  P  K  C  P  F  I  E  N  Q  -

AGCTTCAAGACACTTCAAGATACACAGTTTCTAATCTGAGCATGCAGACACATGCAGCCC
901   ------------------------------------------------------------ + 960
       L  Q  D  T  S  R  Y  T  V  S  N  L  S  M  Q  T  H  A  A  R  -

GCTTTAAAACATTCTTTAACTGGCCCTCTAGTGTTCTAGTTAATCCTGAGCAGCTTGCAA
961   ------------------------------------------------------------ + 1020
       F  K  T  F  F  N  W  P  S  S  V  L  V  N  P  E  Q  L  A  S  -

GTGCGGGTTTTTATTATGTGGGTAACAGTGATGATGTCAAAATGCTTTGCTGTGATGGTG
1021  ------------------------------------------------------------ + 1080
       A  G  F  Y  Y  V  G  N  S  D  D  V  K  C  F  C  C  D  G  G  -
```

Fig. 2 (page 3 of 8)

HUMAN hiap-1

```
        GACTCAGGTGTTGGGAATCTGGAGATGATCCATGGGTTCAACATGCCAAGTGGTTTCCAA
1081    ------+---------+---------+---------+---------+---------+   1140
         L  R  C  W  E  S  G  D  D  P  W  V  Q  H  A  K  W  F  P  R

GGTGTGAGTACTTGATAAGAATTAAAGGACAGAGTTCATCCGTCAAGTTCAAGCCAGTT
1141    ------+---------+---------+---------+---------+---------+   1200
         C  E  Y  L  I  R  I  K  G  Q  E  F  I  R  Q  V  Q  A  S  Y

ACCCTCATCTACTTGAACAGCTGCTATCCACATCAGACAGCCCAGGAGATGAAAATGCAG
1201    ------+---------+---------+---------+---------+---------+   1260
         P  H  L  L  E  Q  L  L  S  T  S  D  S  P  G  D  E  N  A  E

AGTCATCAATTATCCATTTGGAACCTGGAGAAGACCATTCAGAAGATGCAATCATGATGA
1261    ------+---------+---------+---------+---------+---------+   1320
         S  I  I  H  L  E  P  G  E  D  H  S  E  D  A  I  M  M  N

ATACTCCTGTGATTAATGCTGCCGTGGAAATGGGCTTTAGTAGAAGCCTGGTAAAACAGA
1321    ------+---------+---------+---------+---------+---------+   1380
         T  P  V  I  N  A  A  V  E  M  G  F  S  R  S  L  V  K  Q  T

CAGTTCAGAGAAAATCCTAGCAACTGGAGAGAATTATAGACTAGTCAATGATCTTGTGT
1381    ------+---------+---------+---------+---------+---------+   1440
         V  Q  R  K  I  L  A  T  G  E  N  Y  R  L  V  N  D  L  V  L
```

Fig. 2 (page 4 of 8)

HUMAN hiap-1

```
1441 TAGACTTACTCAATGCAGAAGATGAAATAAGGGAAGAGAGAAAGAGCAACTGAGG 1500
       D  L  N  A  E  D  E  I  R  E  E  E  R  E  R  A  T  E  E
1501 AAAAAGAATCAAATGATTTATTATTAATCCGGAAGAATAGAATGGCACTTTTTCAACATT 1560
       K  E  S  N  D  L  L  L  I  R  K  N  R  M  A  L  F  Q  H  L
1561 TGACTTGTGTAATTCCAATCCTGGATAGTCTACTAACTGCCGGAATTATTAATGAACAAG 1620
       T  C  V  I  P  I  L  D  S  L  L  T  A  G  I  I  N  E  Q  E
1621 AACATGATGTTATTAAACAGAAGACACAGACGTCTTTACAAGCAAGAGAACTGATTGATA 1680
       H  D  V  I  K  Q  K  T  Q  T  S  L  Q  A  R  E  L  I  D  T
1681 CGATTTTAGTAAAAGGAAATATTGCAGCCACTGTATTCAGAAACTCTCTGCAAGAAGCTG 1740
       I  L  V  K  G  N  I  A  A  T  V  F  R  N  S  L  Q  E  A  E
1741 AAGCTGTGTTATATGAGCATTTATTTGTGCAACAGCACATAAAATATATTCCCACAGAAG 1800
       A  V  L  Y  E  H  L  F  V  Q  Q  D  I  K  Y  I  P  T  E  D
```

Fig. 2 (page 5 of 8)

HUMAN hiap-1

```
      ATGTTTCAGATCTACCAGTGGAAGAACAATTGCGGAGACTACCAGAAGAAAGAACATGTA
1801  ------------------------------------------------------------  1860
   c
       V  S  D  L  P  V  E  E  Q  L  R  R  L  P  E  E  R  T  C  K

AAGTGTGTATGGACAAAGAAGAAGTGTCCATAGTGTTTATTCCTTGTGGTCATCTAGTAAT
1861  ------------------------------------------------------------  1920
   c
       V  C  M  D  K  E  V  S  I  V  F  I  P  C  G  H  L  V  V  C

GCAAAGATTGTGCTCCTCCTTCTTTAAGAAAGTGTCCTATTTGTAGGAGTACAATCAAGGGTA
1921  ------------------------------------------------------------  1980
   c
       K  D  C  A  P  S  L  R  K  C  P  I  C  R  S  T  I  K  G  T

CAGTTCGTACATTTCTTTCATGAAGAAGAACCAAAACATCGTCTAAACTTTAGAATTAAT
1981  ------------------------------------------------------------  2040
   c
       V  R  T  F  F  L  S  *

TTATTAAATGTATTATATAACTTTTAACTTTTATCCTAAATTGGTTTCCTTAAAATTTTTATT
2041  ------------------------------------------------------------  2100
   c

TATTTACAACTCAAAAAACATTGTTTTGTGTAACATATATTTATATATGTATCTAAACCATA
2101  ------------------------------------------------------------  2160
   c
```

Fig. 2 (page 6 of 8)

HUMAN hiap-1

```
      TGAACATATATTTTTTAGAAACTAAGAGAATGATAGGCTTTTGTTCTTATGAACGAAAAA
2161  ------------------------------------------------------------ 2220
                                                                     c

GAGGTAGCACTACAAACACAATATTCAATCCAAATTTCAGCATTATTGAAATTGTAAGTG
2221  ------------------------------------------------------------ 2280
                                                                     c

AAGTAAAACTTAAGATATTTGAGTTAACCTTTAAGAATTTTAAATATTTTGGCATTGTAC
2281  ------------------------------------------------------------ 2340
                                                                     c

TAATACCGGGAACATGAAGCCAGGTGTGGTGGTATGTACCTGTAGTCCCCAGGCTGAGGCA
2341  ------------------------------------------------------------ 2400
                                                                     c

AGAGAATTACTTGAGCCCAGGAGTTTGAATCCATCCTGGGCAGCATACTGAGACCCTGCC
2401  ------------------------------------------------------------ 2460
                                                                     c

TTTAAAAACXAACAGXACCAAAXCCAAACACCAGGGACACATTTCTCTGTCTTTTTGAT
2461  ------------------------------------------------------------ 2520
                                                                     c
```

HUMAN hiap-1

```
2521 CAGTGTCCTATACATCGAAGGTGTGCATATATGTTGAATCACATTTTAGGGACATGGTGT 2580
     ------+---------+---------+---------+---------+---------+
                                                                  -

2581 TTTTATAAAGAATTCTGTGAGXAAAAATTTAATAAAGCAACCXAAATTACTCTTAAAAAA 2640
     ------+---------+---------+---------+---------+---------+
                                                                  -

2641 AAAAAAAAAAAAAAAAACTCGAGGGGCCCGTACCAAT 2676
     ------+---------+---------+-------
                                         -
```

Fig. 2 (page 8 of 8)

HUMAN hiap-2

```
SEQ ID NO:7          TTAGGTTACCTGAAAGAGTTACTACAACCCCAAAGAGTTGTGTTCTAAGTAGTATCTTGG
                1    ------+---------+---------+---------+---------+---------+   60
                 a   TTAAGGTTACCTGAAAGAGTTACTACAACCCCAAAGAGTTGTGTTCTAAGTAGTATCTTGG

TAATTCAGAGAGATACTCATCCTACCTGAATATAAACTGAGATAAATCCAGTAAAGAAAG
               61    ------+---------+---------+---------+---------+---------+   120
                 a   TAATTCAGAGAGATACTCATCCTACCTGAATATAAACTGAGATAAATCCAGTAAAGAAAG

TGTAGTAAATTCTACATATAAGAGTCTATCATTGATTTCTTTTTGTGGTGGAAATCTTAGTT
              121    ------+---------+---------+---------+---------+---------+   180
                 a   TGTAGTAAATTCTACATATAAGAGTCTATCATTGATTTCTTTTTGTGGTGGAAATCTTAGTT

CATGTGAAGAAATTTCATGTGAATGTTTTAGCTATCAAACAGTACTGTCACCTACTCATG
              181    ------+---------+---------+---------+---------+---------+   240
                 a   CATGTGAAGAAATTTCATGTGAATGTTTTAGCTATCAAACAGTACTGTCACCTACTCATG
                                                                              M

CACAAAACTGCCTCCCAAAGACTTTTCCCAGGTCCCTCGTATCAAAACATTAAGAGTATA
              241    ------+---------+---------+---------+---------+---------+   300
                 a   CACAAAACTGCCTCCCAAAGACTTTTCCCAGGTCCCTCGTATCAAAACATTAAGAGTATA
                     H  K  T  A  S  Q  R  L  F  P  G  P  S  Y  Q  N  I  K  S  I

ATGGAAGATAGCACGATCTTGTCAGATTGGACAAACAGCAACAAACAAAAATGAAGTAT
SEQ ID NO:8 a  301   ------+---------+---------+---------+---------+---------+   360
                 a   ATGGAAGATAGCACGATCTTGTCAGATTGGACAAACAGCAACAAACAAAAATGAAGTAT
                     M  E  D  S  T  I  L  S  D  W  T  N  S  N  K  Q  K  M  K  Y
```

Fig. 3 (page 1 of 7)

HUMAN hiap-2

```
       GACTTTTCCTGTGAACTCTACAGAATGTCTACATATTCAACTTTCCCGCCGGGGTGCCT
361    ------------------------------------------------------------ 420
    a   D   F   S   C   E   L   Y   R   M   S   T   Y   S   T   F   P   A   G   V   P

GTCTCAGAAAGGAGTCTTGCCTCGTGCTGGTTTTTATTATACTGGTGTGAATGACAAGGTC
421    ------------------------------------------------------------ 480
    a   V   S   E   R   S   L   A   R   A   G   F   Y   Y   T   G   V   N   D   K   V

AAATGCTTCTGTTGTGGCCCTGATGCTGGATAACTGGAAACTAGGAGACAGTCCTATTCAA
481    ------------------------------------------------------------ 540
    a   K   C   F   C   C   G   L   M   L   D   N   W   K   L   G   D   S   P   I   Q

AAGCATAAACAGCTATATCCTAGCTGTGTAGCTTTATTCAGAATCTGGTTTCAGCTAGTCTG
541    ------------------------------------------------------------ 600
    a   K   H   K   Q   L   Y   P   S   C   S   F   I   Q   N   L   V   S   A   S   L

GGATCCACCTCTAAGAATACGTCTCCAATGAGAAACAGTTTTGCACATTCATTATCTCCC
601    ------------------------------------------------------------ 660
    a   G   S   T   S   K   N   T   S   P   M   R   N   S   F   A   H   S   L   S   P

ACCTTGGAACATAGTAGCTTGTTCAGTGGTTCTTACTCCAGCCTTCCTCCAAACCCTCTT
661    ------------------------------------------------------------ 720
    a   T   L   E   H   S   S   L   F   S   G   S   Y   S   S   L   P   P   N   P   L
```

Fig. 3 (page 2 of 7)

HUMAN hiap-2

```
     AATTCTAGAGCAGTTGAAGACATCTCTTCATCGAGGACTAACCCCTACAGTTATGCAATG
721  ------+---------+---------+---------+---------+---------+ 780
      N  S  R  A  V  E  D  I  S  S  R  T  N  P  Y  S  Y  A  M

AGTACTGAAGAAGCCAGATTTCTTACCTACCATATGTGGCCATTAACTTTTTGTCACCA
781  ------+---------+---------+---------+---------+---------+ 840
      S  T  E  E  A  R  F  L  T  Y  H  M  W  P  L  T  F  L  S  P

TCAGAATTGGCAAGAGCTGGTTTTTATTATATAGGACCTGGAGATAGGGTAGCCTGCTTT
841  ------+---------+---------+---------+---------+---------+ 900
      S  E  L  A  R  A  G  F  Y  Y  I  G  P  G  D  R  V  A  C  F

GCCTGTGGTGGGAAGCTCAGTAACTGGGAACCAAAGGATGATGCTATGTCAGAACACCGG
901  ------+---------+---------+---------+---------+---------+ 960
      A  C  G  G  K  L  S  N  W  E  P  K  D  D  A  M  S  E  H  R

AGGCATTTTCCCAACTGTCCATTTTTGGAAAATTCTCTAGAAACTCTGAGGTTTAGCATT
961  ------+---------+---------+---------+---------+---------+ 1020
      R  H  F  P  N  C  P  F  L  E  N  S  L  E  T  L  R  F  S  I

TCAAATCTGAGCATGCAGACACATGCAGCTCGAATGAGAACATTTATGTACTGGCCATCT
1021 ------+---------+---------+---------+---------+---------+ 1080
      S  N  L  S  M  Q  T  H  A  A  R  M  R  T  F  M  Y  W  P  S
```

Fig. 3 (page 3 of 7)

HUMAN hiap-2

```
      AGTGTTCCAGTTCAGCCCTGAGCAGCTTGCAAGTGCTGGTTTTTATTATGTGGGTCGCAAT
1081  ------------+---------+---------+---------+---------+---------+  1140
   a   S  V  P  V  Q  P  E  Q  L  A  S  A  G  F  Y  Y  V  G  R  N

GATGATGTCAAATGCTTTGGTTGTGATGGTGGCTTGAGGTGTTGGGAATCTGGAGATGAT
1141  ------------+---------+---------+---------+---------+---------+  1200
   a   D  D  V  K  C  F  G  C  D  G  G  L  R  C  W  E  S  G  D  D

CCATGGGTAGAACATGCCAAGTGGTTTCCAAGGTGTGAGTTCTTGATACGAATGAAAGGC
1201  ------------+---------+---------+---------+---------+---------+  1260
   a   P  W  V  E  H  A  K  W  F  P  R  C  E  F  L  I  R  M  K  G

CAAGAGTTTGTTGATGAGATTCAAGGTAGATATCCTCATCTTCTTGAACAGCTGTTGTCA
1261  ------------+---------+---------+---------+---------+---------+  1320
   a   Q  E  F  V  D  E  I  Q  G  R  Y  P  H  L  L  E  Q  L  L  S

ACTTCAGATACCACTGGAGAAGAAAATGCTGACCCCACCAATTATTCATTTTGGACCTGGA
1321  ------------+---------+---------+---------+---------+---------+  1380
   a   T  S  D  T  T  G  E  E  N  A  D  P  P  I  H  F  G  P  G

GAAAGTTCTTCAGAAGATGCTGTCATGATGAATACACCTGTGGTTAAATCTGCCTTGAA
1381  ------------+---------+---------+---------+---------+---------+  1440
   a   E  S  S  E  D  A  V  M  M  N  T  P  V  V  K  S  A  L  E
```

Fig. 3 (page 4 of 7)

HUMAN hiap-2

```
1441  ATGGGCTTTAATAGAGACCTGGTGAAACAACAGTTCTAAGTAAAATCCTGACAACTGGA
      ----+----+----+----+----+----+----+----+----+----+----+----+ 1500
       M  G  F  N  R  D  L  V  K  Q  T  V  L  S  K  I  L  T  T  G

1501  GAGAACTATAAAACAGTTAATGATATTGTGTCAGCACTTCTTAATGCTGAAGATGAAAAA
      ----+----+----+----+----+----+----+----+----+----+----+----+ 1560
       E  N  Y  K  T  V  N  D  I  V  S  A  L  L  N  A  E  D  E  K

1561  AGAGAAGAGGAGAAGAAACAAGCTGAAGAAATGGCATCAGATGATTGTCATTAATT
      ----+----+----+----+----+----+----+----+----+----+----+----+ 1620
       R  E  E  E  K  E  K  Q  A  E  E  M  A  S  D  D  L  S  L  I

1621  CGGAAGAACACAGAATGGCTCTCTCTTTCAACAATTGACACATGTGTGCTTCCTATCCTGGATAAT
      ----+----+----+----+----+----+----+----+----+----+----+----+ 1680
       R  K  N  R  M  A  L  F  Q  Q  L  T  C  V  L  P  I  L  D  N

1681  CTTTTAAAGGCCAATGTAATTAATAAACAGAGAACATGATATTATTAAACAAAAACACAG
      ----+----+----+----+----+----+----+----+----+----+----+----+ 1740
       L  L  K  A  N  V  I  N  K  Q  E  H  D  I  I  K  Q  K  T  Q

1741  ATACCCTTTACAAGCGGAGAGAACTGATTGATACCATTTGGGTTAAAGGAAAATGCTGCGGCC
      ----+----+----+----+----+----+----+----+----+----+----+----+ 1800
       I  P  L  Q  A  R  E  L  I  D  T  I  W  V  K  G  N  A  A  A
```

Fig. 3 (page 5 of 7)

HUMAN hiap-2

```
1801 AACATCTTCAAAAACTGTCTAAAGAAATTGACTCTACATTGTATAAGAACTTATTTGTG 1860
      N  I  F  K  N  C  L  K  E  I  D  S  T  L  Y  K  N  L  F  V
1861 GATAAGAATATGAAGTATATTCCAACAGAAGATGTTTCAGGTCTCTGTCACTGGAAGAACAA 1920
      D  K  N  M  K  Y  I  P  T  E  D  V  S  G  L  S  L  E  E  Q
1921 TTGAGGAGGTTGCAAGAAGAACGAACTTGTAAAGTGTGTATGGACAAAGAAGTTTCTGTT 1980
      L  R  R  L  Q  E  E  R  T  C  K  V  C  M  D  K  E  V  S  V
1981 GTATTTATTCCTTGTGGTCATCTGGTAGTATGCCAGGAATGTGCCCCTTCTCTAAGAAAA 2040
      V  F  I  P  C  G  H  L  V  V  C  Q  E  C  A  P  S  L  R  K
2041 TGCCCTATTTGCAGGGGTATAATCAAGGGTACTGTTCGTACATTTCTCTCTTAAAGAAAA 2100
      C  P  I  C  R  G  I  I  K  G  T  V  R  T  F  L  S  *
2101 ATAGTCTATATATTTTAACCTGCATAAAAAGGTCTTTAAAATATTGTTGAACACTTGAAGCC 2160
```

Fig. 3 (page 6 of 7)

HUMAN hiap-2

```
2161 ATCTAAAGTAAAAAGGGAATTATGAGTTTTCAATTAGTAACATTCATGTTCTAGTCTGC 2220
     ----+----+----+----+----+----+----+----+----+----+----+----+
2221 TTTGGTACTAATAATCTTGTTTCTGAAAAGATGGTATCATATATTTAATCTTAATCTGTT 2280
     ----+----+----+----+----+----+----+----+----+----+----+----+
2281 TATTTACAAGGGAAGATTTATGTTTGGTGAACTATATTAGTATGTGTACCTAAGGG 2340
     ----+----+----+----+----+----+----+----+----+----+----+----+
2341 AGTAGCGTCXCTGCTTGTTATGCATCATTTCAGGAGTTACTGGATTTGTTGTTCTTTCAG 2400
     ----+----+----+----+----+----+----+----+----+----+----+----+
2401 AAAGCTTTGAAXACTAAATTATAGTGTAGAAAAGAACTGGAAACCAGGAACTCTGGAGTT 2460
     ----+----+----+----+----+----+----+----+----+----+----+----+
2461 CATCAGAGAGTTATGGTGCCGAATTGTCTTTGGTGCTTTTCACTTGTGTTTAAAATAAGGA 2520
     ----+----+----+----+----+----+----+----+----+----+----+----+
2521 TTTTTCTCTTATTTCTCCCCCTAGTTTGTGAGAAACATCTCAATAAAGTGCTTTAAAAAG 2580
     ----+----+----+----+----+----+----+----+----+----+----+----+
```

Fig. 3 (page 7 of 7)

MOUSE xiap

```
SEQ ID NO:9      1   GACACTCTGCTGGGCGGCGGGCCGCCCCTCCTCCGGGAACCTCCCCTCGGGAACCGTCGCCC
                     ---------+---------+---------+---------+---------+---------+   60

61   GCGGCGCTTAGTTAGGACTGGAGTGCTTGGCGCGGAAAAGGTGGACAAGTCCTATTTTCCA
                     ---------+---------+---------+---------+---------+---------+  120

121   GAGAAGATGACTTTTTAAACAGTTTTGAAGGAACTAGAACTTTTGTACTTGCAGACACCAAT
                     ---------+---------+---------+---------+---------+---------+  180

SEQ ID NO:10           M  T  F  N  S  F  E  G  T  R  T  F  V  L  A  D  T  N

181   AAGGATGAAGAATTTGTAGAAGAGTTTAATAGATTAAAAACATTTGCTAACTTCCCAAGT
                     ---------+---------+---------+---------+---------+---------+  240
                       K  D  E  E  F  V  E  E  F  N  R  L  K  T  F  A  N  F  P  S

241   AGTAGTCCTGTTTCAGCATCAACATTGGCGCGAGCTGGGTTTCTTTATACCGGTGAAGGA
                     ---------+---------+---------+---------+---------+---------+  300
                       S  S  P  V  S  A  S  T  L  A  R  A  G  F  L  Y  T  G  E  G

301   GACACCGTGCAATGTTTCAGTTGTCATGCGGCAATAGATAGATGGCAGTATGGAGACTCA
                     ---------+---------+---------+---------+---------+---------+  360
                       D  T  V  Q  C  F  S  C  H  A  A  I  D  R  W  Q  Y  G  D  S
```

Fig. 4 (page 1 of 6)

MOUSE xiap

```
361  GCTGTTGGAAGACACAGGAGAATATCCCCAAATTGCAGATTTATCAATGGTTTTTATTTT   420
     ------+---------+---------+---------+---------+---------+
   a  A  V  G  R  H  R  R  I  S  P  N  C  R  F  I  N  G  F  Y  F

421  GAAAATGGTGCTGCACAGTCTACAAATCCTGGTATCCAAAATGGCCAGTACAAATCTGAA   480
     ------+---------+---------+---------+---------+---------+
   a  E  N  G  A  A  Q  S  T  N  P  G  I  Q  N  G  Q  Y  K  S  E

481  AACTGTGTGGGAAATAGAAATCCTTTTGCCCCTGACAGGCCACCTGAGACTCATGCTGAT   540
     ------+---------+---------+---------+---------+---------+
   a  N  C  V  G  N  R  N  P  F  A  P  D  R  P  P  E  T  H  A  D

541  TATCTCTTGAGAACTGGACAGGTTGTAGATATTTCAGAACACCATATACCCGAGAACCCT   600
     ------+---------+---------+---------+---------+---------+
   a  Y  L  L  R  T  G  Q  V  V  D  I  S  D  T  I  Y  P  R  N  P

601  GCCATGTGTAGTGAAGAAGCCAGATTGAAGTCATTTCAGAACTGGCCGGACTATGCTCAT   660
     ------+---------+---------+---------+---------+---------+
   a  A  M  C  S  E  E  A  R  L  K  S  F  Q  N  W  P  D  Y  A  H

661  TTAACCCCCAGAGAGTTAGCTGCTAGTGCTGGCCTCTACTACACAGGGGCTGATGATCAAGTG   720
     ------+---------+---------+---------+---------+---------+
   a  L  T  P  R  E  L  A  S  A  G  L  Y  Y  T  G  A  D  D  Q  V
```

Fig. 4 (page 2 of 6)

MOUSE xiap

```
      CAATGCTTTTGTTGTGGGGAAAACTGAAAAATTGGAACCCTGTGATCGTGCCTGGTCA
721   ------------------------------------------------------------  780
      Q  C  F  C  C  G  G  K  L  K  N  W  E  P  C  D  R  A  W  S

GAACACAGGAGAGACACTTTCCCAATTGCTTTTTTGTTTTGGGCCGGAACGTTAATGTTCGA
781   ------------------------------------------------------------  840
      E  H  R  R  H  F  P  N  C  F  F  V  L  G  R  N  V  N  V  R

AGTGAATCTGGTGTGAGTTCTGATAGGAATTCCCAAATTCAACAAACTCTCCAAGAAAT
841   ------------------------------------------------------------  900
      S  E  S  G  V  S  S  D  R  N  F  P  N  S  T  N  S  P  R  N

CCAGCCATGGCAGAATATGAAGCACGGATCGTTACTTTTGGAACATGGATATACTCAGTT
901   ------------------------------------------------------------  960
      P  A  M  A  E  Y  E  A  R  I  V  T  F  F  G  T  W  I  Y  S  V

AACAAGGAGCAGCTTGCAAGAGCTGGATTTTATGCTTTAGGTGAAGGCGATAAAGTGAAG
961   ------------------------------------------------------------  1020
      N  K  E  Q  L  A  R  A  G  F  Y  A  L  G  E  G  D  K  V  K

TGCTTCCACTGTGGAGAGGGCTCACGGATTGGAAGCCAAGTGAAGACCCCTGGGACCAG
1021  ------------------------------------------------------------  1080
      C  F  H  C  G  G  G  L  T  D  W  K  P  S  E  D  P  W  D  Q
```

Fig. 4 (page 3 of 6)

MOUSE xiap

```
1081  CATGCTAAGTGCTACCCAGGTGCAAATACCTATTGGATGAGAAGGGGCAAGAATATATA   1140
       H  A  K  C  Y  P  G  C  K  Y  L  L  D  E  K  G  Q  E  Y  I

1141  AATAATATTCATTTAACCCATCCACTTGAGGAATCTTTGGGAAGAACTGCTGAAAAAACA   1200
       N  N  I  H  L  T  H  P  L  E  E  S  L  G  R  T  A  E  K  T

1201  CCACCGCTAACTAAAAAAATCGATGATACCATCTTCCAGAATCCTATGGTGCAAGAAGCT   1260
       P  P  L  T  K  K  I  D  D  T  I  F  Q  N  P  M  V  Q  E  A

1261  ATACGAATGGGATTTAGCTTCAAGGACCTTGAGGTCCTGATTGCAGATCTTGTGAGTGCTCAGAAA   1320
       I  R  M  G  F  S  F  K  D  L  K  K  T  M  E  E  K  I  Q  T

1321  TCCGGGAGCAGCTATCTACTCACTTGAGGTCCTGATTGCAGATCTTGTGAGTGCTCAGAAA   1380
       S  G  S  S  Y  L  S  L  E  V  L  I  A  D  L  V  S  A  Q  K

1381  GATAATACGGAGGATGAGTCAAGTCAAACTTCATTGCAGAAAGACATTAGTACTGAAGAG   1440
       D  N  T  E  D  E  S  S  Q  T  S  L  Q  K  D  I  S  T  E  E
```

Fig. 4 (page 4 of 6)

MOUSE xiap

```
1441 CAGCTAAGGCGCCTACAAGAGGAGAAGCTTTCCAAAATCTGTATGGATAGAAATATTGCT
     ------------------------------+------------------------------ 1500
      Q   L   R   R   L   Q   E   E   K   L   S   K   I   C   M   D   R   N   I   A

1501 ATCGTTTTTTTTCCTTGTGGACATCTGGCCACTTGTAAACAGTGTGCAGAAGCAGTTGAC
     ------------------------------+------------------------------ 1560
      I   V   F   F   P   C   G   H   L   A   T   C   K   Q   C   A   E   A   V   D

1561 AAATGTCCCATGTGCTACACCGTCATTACGTTCAACCAAAAAATTTTTATGTCTTAGTGG
     ------------------------------+------------------------------ 1620
      K   C   P   M   C   Y   T   V   I   T   F   N   Q   K   I   F   M   S   *

1621 GGCACCACATGTTATGTTCTTCTTGCTCTAATTGAATGTGTAATGGGAGCGAACTTTAAG
     ------------------------------+------------------------------ 1680

1681 TAATCCTGCATTTGCATTCCATTAGCATCCTGCTGTTTCCAAATGGAGACCAATGCTAAC
     ------------------------------+------------------------------ 1740

1741 AGCACTGTTTCCGTCTAAACATTCAATTTCTGGATCTTTCGAGTTATCAGCTGTATCATT
     ------------------------------+------------------------------ 1800
```

Fig. 4 (page 5 of 6)

MOUSE xiap

```
1801 TAGCCAGTGTTTTACTCGATTGAAACCTTAGACAGAGAAGCATTTTATAGCTTTTCACAT 1860
     ------+---------+---------+---------+---------+---------+

1861 GTATATTGGTAGTAGTACACACTGACTTGATTTCTATATGTAAGTGAATTCATCACCTGCATGTT 1920
     ------+---------+---------+---------+---------+---------+

1921 TCATGCCTTTTGCATAAGCTTAACAAATGGAGTGTTCTGTATAAGCATGGAGATGTGATG 1980
     ------+---------+---------+---------+---------+---------+

1981 GAATCTGCCCAATGACTTTAATTGGCTTATTGTAAACACGGAAAGAACTGCCCCACGCTG 2040
     ------+---------+---------+---------+---------+---------+

2041 CTGGGAGGATAAAGATTGTTTTAGATGCTCACTTCTGTGTTTTAGGATTCTGCCCATTTA 2100
     ------+---------+---------+---------+---------+---------+
```

Fig. 4 (page 6 of 6)

M-hiap-1

```
SEQ ID NO:39
          1 GAATTCCGGGAGACCTACACCCCGGAGATCAGAGGTCATTGCTGGCGTTCAGAGCCTAG     60
         61 GAAGTGGGCTGCGGGTATCAGCCTAGCAGTAAAAACCGACCAGAAGCCATGCACAAAACTAC  120
        121 ATCCCCAGAGAAAGACTTGTCCCCTCCCCTGTCATCTCACCATGAACATGGTTCAA       180
SEQ ID NO:40
                                                         M  N  M  V  Q
        181 GACAGCGCCTTTCTAGCCAAGCTGATGAAGAGTGCTGACACCTTTGAGTTGAAGTATGAC   240
             D  S  A  F  L  A  K  L  M  K  S  A  D  T  F  E  L  K  Y  D
        241 TTTTCCTGTGAGCTGTACCGATTGTCCACGTATTCAGCTTTTCCCAGGGGAGTTCCTGTG   300
             F  S  C  E  L  Y  R  L  S  T  Y  S  A  F  D  R  G  V  P  V
        301 TCAGAAAGGAGTCTGGCTCGTGCTGGCTTTTACTACACTGGTGCCAATGACAAGGTCAAG   360
             S  E  R  S  L  A  R  A  G  F  Y  Y  T  G  A  N  D  K  V  K
        361 TGCTTCCGCTGTGGCCTGATGCTAGACAACTGGAAACAAGGGGACAGTCCCATGGAGAAG   420
             C  F  C  C  G  L  M  L  D  N  W  K  Q  G  D  S  P  M  E  K
```

Fig. 5 (page 1 of 6)

M-hiap-1

```
     CACAGAAAGTTGTACCCCAGCTGCAACTTTGTACAGACTTTGAATCCAGCCAACAGTCTG
421  ------+---------+---------+---------+---------+---------+  480
      H  R  K  L  Y  P  S  C  N  F  V  Q  T  L  N  P  A  N  S  L

GAAGCTAGTCCTCGGCCTTCTCTTCCTTCCACGGCGATGAGCACCATGCCTTTGAGCTTT
481  ------+---------+---------+---------+---------+---------+  540
      E  A  S  P  R  P  S  L  P  S  T  A  M  S  T  M  P  L  S  F

GCAAGTTCTGAGAATACTGGCTATTTCAGTGGCTCTTACTGAGCTTTCCCTCAGACCCT
541  ------+---------+---------+---------+---------+---------+  600
      A  S  S  E  N  T  G  Y  F  S  G  S  Y  S  S  F  P  S  D  P

GTGAACTTCCGAGCAAATCAAGATTGTCCTGCTTTGAGCACAAGTCCCTACCACTTTGCA
601  ------+---------+---------+---------+---------+---------+  660
      V  N  F  R  A  N  Q  D  C  P  A  L  S  T  S  P  Y  H  F  A

ATGAACACAGAGAAGGCCAGATTACTCACCTATGAAACATGGCCATTGTCTTTTCTGTCA
661  ------+---------+---------+---------+---------+---------+  720
      M  N  T  E  K  A  R  L  L  T  Y  E  T  W  P  L  S  F  L  S

CCAGCAAAGCTGGCCAAAGCAGGCTTCTACTACATAGGACCTGGAGATAGAGTGGCCTGC
721  ------+---------+---------+---------+---------+---------+  780
      P  A  K  L  A  K  A  G  F  Y  Y  I  G  P  G  D  R  V  A  C
```

Fig. 5 (page 2 of 6)

M-hiap-1

```
       TTTGCGTGCGATGGGAAACTGAGCAACTGGGAACGTAAGGATGATGCTATGTCAGAGCAC
 781   ----+----+----+----+----+----+----+----+----+----+----+----+  840
       F  A  C  D  G  K  L  S  N  W  E  R  K  D  D  A  M  S  E  H

CAGAGGCATTCCCCAGCTGTCCGTTCTTALLkGACTTGGGTCAGTCTGCTTCGAGATAC
 841   ----+----+----+----+----+----+----+----+----+----+----+----+  900
       Q  R  H  F  P  S  C  P  F  L  K  D  L  G  Q  S  A  S  R  Y

ACTGTCTCTAACCTGAGCATGCAGACACACGCAGCCCGTATTAGAACATTCTCTAACTGG
 901   ----+----+----+----+----+----+----+----+----+----+----+----+  960
       T  V  S  N  L  S  M  Q  T  H  A  A  R  I  R  T  F  S  N  W

CCTTCTAGTGCACTAGTTCATTCCCAGGAACTTGCAAGTGCGGGCTTTTATTATACAGGA
 961   ----+----+----+----+----+----+----+----+----+----+----+----+ 1020
       P  S  S  A  L  V  H  S  Q  E  L  A  S  A  G  F  Y  Y  T  G

CACAGTGATGATGTCAAGTGTTTATGCTGTGATGGTGGGCTGAGGTGCTGGGAATCTGGA
1021   ----+----+----+----+----+----+----+----+----+----+----+----+ 1080
       H  S  D  D  V  K  C  L  C  C  D  G  G  L  R  C  W  E  S  G

GATGACCCCTGGGTGGAACATGCCAAGTGGTTCCAAGGTGTGAGTACTTGCTCAGAATC
1081   ----+----+----+----+----+----+----+----+----+----+----+----+ 1140
       D  D  P  W  V  E  H  A  K  W  F  P  R  C  E  Y  L  L  R  I

AAAGGCCAAGAATTTGTCAGCCAAGTTCAAGCTGGCTATCCTCATCTACTTGAGCAGCTA
1141   ----+----+----+----+----+----+----+----+----+----+----+----+ 1200
       K  G  Q  E  F  V  S  Q  V  Q  A  G  Y  P  H  L  L  E  Q  L
```

Fig. 5 (page 3 of 6)

M-hiap-1

```
1201 TTATCTACGTCAGACTCCCCAGAAGATGAGAATGCAGACGCAGCAATCGTGCATTTGGC 1260
      L  S  T  S  D  S  P  E  D  E  N  A  D  A  A  I  V  H  F  G

1261 CCTGGAGAAAGTTCGGAAGATGTCGTCATGATGAGCACGCCCTGTGGTTAAAGCAGCCTTG 1320
      P  G  E  S  S  E  D  V  V  M  M  S  T  P  V  V  K  A  A  L

1321 GAAATGGGCTTCAGTAGGAGCCTGGTGAGACAGACAGGTTCAGTGGCAGATCCTGGCCACT 1380
      E  M  G  E  S  R  S  L  V  R  Q  T  V  Q  W  Q  I  L  A  T

1381 GGTGAGAACTACAGGACCGTCAGTGACCTCGTTATAGGCTTACTCGATGCAGAAGACGAG 1440
      G  E  N  Y  R  T  V  S  D  L  V  I  G  L  L  D  A  E  D  E

1441 ATGAGAGAGGAGCAGATGGAGCAGGCGGCCGAGGAGGAGTCAGATGATCTAGCACTA 1500
      M  R  E  E  Q  M  E  Q  A  A  E  E  E  E  S  D  D  L  A  L

1501 ATCCGGAAGAACAAAATGGTGCTTTTCCAACATTTGACGTGTGTGACACCAATGCTGTAT 1560
      I  R  K  N  K  M  V  L  F  Q  H  L  T  C  V  T  P  M  L  Y
```

Fig. 5 (page 4 of 6)

M-hiap-1

```
      TGCCTCCTAAGTGCAAGGGCCATCACTGAACAGGAGTGCAATGCTGTGAAACAGAAACCA
1561  ------------+---------+---------+---------+---------+---------+  1620
       C  L  L  S  A  R  A  I  T  E  Q  E  C  N  A  V  K  Q  K  P

CACACCTTACAAGCAAGCACACTGATTGATACTGTGTTAGCAAAAGGAAACACTGCAGCA
1621  ------------+---------+---------+---------+---------+---------+  1680
       H  T  L  Q  A  S  T  L  I  D  T  V  L  A  K  G  N  T  A  A

ACCTCATTCAGAAACTCCCCTTCGGGAAATTGACCCTGCGTTATACAGAGATATATTTGTG
1681  ------------+---------+---------+---------+---------+---------+  1740
       T  S  F  R  N  S  L  R  E  I  D  P  A  L  Y  R  D  I  F  V

CAACAGGACATTAGGAGTCTTCCCACAGATGACATTGCAGCTCTACCAATGGAAGAACAG
1741  ------------+---------+---------+---------+---------+---------+  1800
       Q  Q  D  I  R  S  L  P  T  D  D  I  A  A  L  P  M  E  E  Q

TTGCGGCCCCTCCCGGAGGACAGAAATGTGTAAAGTGTGTATGGACCGAGAGGTATCCATC
1801  ------------+---------+---------+---------+---------+---------+  1860
       L  R  P  L  P  E  D  R  M  C  K  V  C  M  D  R  E  V  S  I

GTGTTCATTCCCTGTGCCCATCTGGTCGTGTGCAAAGACTGCGCTCCCTCTCTGAGGAAG
1861  ------------+---------+---------+---------+---------+---------+  1920
       V  F  I  P  C  G  H  L  V  V  C  K  D  C  A  P  S  L  R  K
```

Fig. 5 (page 5 of 6)

M-hiap-1

```
1921 TGTCCCATCTGTAGAGGGACCATCAAGGGCACAGTGCGCACATTTCTCTCCTGAACAAGA 1980
      C  P  I  C  R  G  T  I  K  G  T  V  R  T  F  L  S  *
1981 CTAATGGTCCATGGCTGCAACTTCAGCCAGGAGGAAGTTCACTGTCACTCCCAGTTCCAT 2040
2041 TCGGAACTTGAGGCCAGCCTGGATAGCACGAGACACCGCCAAACkCACAAATATAAACAT 2100
2101 GAAAAACTTTTGTCTGAAGTCAAGAATGAATGAATTACTTATATAATAATTTTAATTGGT 2160
2161 TTCCTTAAAGTGCTATTTGTTCCCAACTCAGAAAATTGTTTTCTGTAAACATATTTACA 2220
2221 TACTACCTGCATCTAAAGTATTCATATATTCATATATTCAGATGTCATGAGAGAGGGTTT 2280
2281 TGTTCTTGTTCCTGAAAGCTGGTTTATCATCTGATCAGCATATACTGCGCAACGGGCAG 2340
2341 GGCTAGAATCCATGAACCAAGCTGCAAAGATCTCACGCTAAATAAGGCGGAAAGATTGG 2400
2401 AGAAACGAAAGGAAATTCTTTCCTGTCCAATGTATACTCTTCAGACTAATGACCTCTTCC 2460
2461 TATCAAGCCTTCTA 2474
```

Fig. 5 (page 6 of 6)

M-hiap-2

```
SEQ ID NO:41      CTGTGGTGGAGATCTATTGTCCAAGTGGTGAGAAACTTCATCTGGAAGTTTAAGCGGTCA
             1    ------+---------+---------+---------+---------+---------+    60
                  GAAATACTATTACTACTCATGGACAkRACTGTCTCCCAGAGACTCGCCCAAGGTACCTTA

61    ------+---------+---------+---------+---------+---------+   120
                  CACCCRAAAACTTAAACGTATAATGGAGAAGAGCACAATCTTGTCAAATTGGACAAAGGA

SEQ ID NO:42  
           121    ------+---------+---------+---------+---------+---------+   180
                          M   E   K   S   T   I   L   S   N   W   T   K   E

GAGCGAAGAAAAATGAAGTTTGACTTTTCGTGTGAACTCTACCGAATGTCTACATATTC
           181    ------+---------+---------+---------+---------+---------+   240
                    S   E   E   K   M   K   F   D   F   S   C   E   L   Y   R   M   S   T   Y   S

AGCTTTTCCCAGGGGAGTTCCTGTCTCAGAGAGAGTCTGGCTCGTGCTGGCTTTTATTA
           241    ------+---------+---------+---------+---------+---------+   300
                    A   F   P   R   G   V   P   V   S   E   R   S   L   A   R   A   G   F   Y   Y

TACAGGTGTGAATGACAAAGTCAAGTGCTTCTGCTGTGGCCTGATGTTGGATAACTGGAA
           301    ------+---------+---------+---------+---------+---------+   360
                    T   G   V   N   D   K   V   K   C   F   C   C   G   L   M   L   D   N   W   K

ACAAGGGGACAGTCCTGTTGAAAAGCACAGACAGTTCTATCCCAGCTGCAGCTTTGTACA
           361    ------+---------+---------+---------+---------+---------+   420
                    Q   G   D   S   P   V   E   K   H   R   Q   F   Y   P   S   C   S   F   V   Q
```

Fig. 6 (page 1 of 6)

M-hiap-2

```
     GACTCTGCTTTCAGCCAGTCTGCAGTCTCCATCTAAGAATATGTCTCCTGTGAAAAGTAG
421  ------+---------+---------+---------+---------+---------+   480
      T  L  S  A  S  L  Q  S  P  S  K  N  M  S  P  V  K  S  R  -

ATTTGCACACATTCGTCACCTCTGGAACGAGGTGGCATTCACTCCAACCTGTGCTCTAGCCC
481  ------+---------+---------+---------+---------+---------+   540
      F  A  H  S  S  P  L  E  R  G  G  I  H  S  N  L  C  S  S  P  -

TCTTAATTCTAGAGCAGTGGAAGACTTCTCATCAAGGATGGATCCCCTGCAGCTATGCCAT
541  ------+---------+---------+---------+---------+---------+   600
      L  N  S  R  A  V  E  D  F  S  S  R  M  D  P  C  S  Y  A  M  -

GAGTACAGAAGAGGCCAGATTTCTTACTTACAGTATGTGGCCTTTAAGTTTTCTGTCACC
601  ------+---------+---------+---------+---------+---------+   660
      S  T  E  E  A  R  F  L  T  Y  S  M  W  P  L  S  F  L  S  P  -

AGCAGAGCTGGCCAGAGCTGGCTTCTATTACATAGGGCCTGGAGACAGGGTGGCCTGTTT
661  ------+---------+---------+---------+---------+---------+   720
      A  E  L  A  R  A  G  F  Y  Y  I  G  P  G  D  R  V  A  C  F  -

TGCCTGTGGGTGGGAAACTGAGCAACTGGGAACCAAAGGATTATGCTATGTCAGAGCACCG
721  ------+---------+---------+---------+---------+---------+   780
      A  C  G  G  K  L  S  N  W  E  P  K  D  Y  A  M  S  E  H  R  -
```

Fig. 6 (page 2 of 6)

M-hiap-2

```
       CAGACATTTCCCCACTGTCCATTTCTGGAAATACTTCAGAAACACAGAGGTTTAGTAT
 781   ------+---------+---------+---------+---------+---------+  840
       R  H  F  P  H  C  P  F  L  E  N  T  S  E  T  Q  R  F  S  I

ATCAAATCTAAGTATGCAGACACACTCTGCTCTGATTGAGGACATTTCTGTACTGGCCACC
 841   ------+---------+---------+---------+---------+---------+  900
       S  N  L  S  M  Q  T  H  S  A  R  L  R  T  F  L  Y  W  P  P

TAGTGTTCCTGTTCAGCCCGAGCAGCTTGCAAGTGCTGGATTCTATTACGTGGATCGCRA
 901   ------+---------+---------+---------+---------+---------+  960
       S  V  P  V  Q  P  E  Q  L  A  S  A  G  F  Y  Y  V  D  R  N

TGATGATGTCAAGTGCCTTTGTTGTGATGGTGGCTTGAGATGTTGGGAACCTGGAGATGA
 961   ------+---------+---------+---------+---------+---------+ 1020
       D  D  V  K  C  L  C  C  D  G  G  L  R  C  W  E  P  G  D  D

CCCCTGGATAGAACACGCCAAATGGTTTCCAAGGTGTGAGTTCTTGATACGGATGAAGGG
1021   ------+---------+---------+---------+---------+---------+ 1080
       P  W  I  E  H  A  K  W  F  P  R  C  E  F  L  I  R  M  K  G

TCAGGAGTTTGTTGATGAGATTCAAGCTAGATATCCTCATCTTCTTGAGCAGCTGTTGTC
1081   ------+---------+---------+---------+---------+---------+ 1140
       Q  E  F  V  D  E  I  Q  A  R  Y  P  H  L  L  E  Q  L  L  S
```

Fig. 6 (page 3 of 6)

M-hiap-2

```
      CACTTCAGACACCCCAGGAGAAGAAATGCTGACCCTACAGAGACAGTGGTGCATTTGG
1141  ------+---------+---------+---------+---------+---------+  1200
      T  S  D  T  P  G  E  E  N  A  D  P  T  E  T  V  V  H  F  G

CCCTGGAGAAAGTTCGAAAGATGTCGTCATGATGAGCACGCCTGTGGTTAAAGCAGCCTT
1201  ------+---------+---------+---------+---------+---------+  1260
      P  G  E  S  S  K  D  V  V  M  M  S  T  P  V  V  K  A  A  L

GGAAATGGGCTTCAGTAGGAGCCTGGTGAGACAGACGGTTCAGCGGCAGATCCTGGCCAC
1261  ------+---------+---------+---------+---------+---------+  1320
      E  M  G  F  S  R  S  L  V  R  Q  T  V  Q  R  Q  I  L  A  T

TGGTGAGAACTACAGGACCGTCAATGATATTGTCTCAGTACTTTTGAATGCTGAAGATGA
1321  ------+---------+---------+---------+---------+---------+  1380
      G  E  N  Y  R  T  V  N  D  I  V  S  V  L  L  N  A  E  D  E

GAGAAGAGAAGAGGAGAAAGACAGACTGAAGAGATGGCATCAGGTGACTTATCACT
1381  ------+---------+---------+---------+---------+---------+  1440
      R  R  E  E  K  E  R  Q  T  E  E  M  A  S  G  D  L  S  L

GATTCGGAAGAATAGAATGGCCCTCTTTCAACAGTTGACACATGTCCTTCCTATCCTGA
1441  ------+---------+---------+---------+---------+---------+  1500
      I  R  K  N  R  M  A  L  E  Q  Q  L  T  H  V  L  P  I  L  D
```

Fig. 6 (page 4 of 6)

M-hiap-2

```
      TAATCTTCTTGAGGCCAGTGTAATTACAAAACAGGAACATGATATTATTAGACAGAAAAC
1501  ------+---------+---------+---------+---------+---------+ 1560
       N  L  E  A  S  V  I  T  K  Q  E  H  D  I  R  Q  K  T

ACAGATACCCTTACAAGCAAGAGAGCTTATTGACACCGTTTAGTCAAGGGAAATGCTGC
1561  ------+---------+---------+---------+---------+---------+ 1620
       Q  I  P  L  Q  A  R  E  L  I  D  T  V  L  V  K  G  N  A  A

AGCCAACATCTTCAAAAACTCTCTGAAGGGAATTGACTCCACGTTATATGAAAACTTATT
1621  ------+---------+---------+---------+---------+---------+ 1680
       A  N  I  F  K  N  S  L  K  G  I  D  S  T  L  Y  E  N  L  F

TGTGGAAAAGAATATGAAGTATATTCCAACAGAAGACGTTTCAGGCTTGTCATTGGAAGA
1681  ------+---------+---------+---------+---------+---------+ 1740
       V  E  K  N  M  K  Y  I  P  T  E  D  V  S  G  L  S  L  E  E

GCAGTTGCGGAGATTACAAGAAGAACGAACTTGCAAAGTGTGTATGGACAGAGAGGTTTC
1741  ------+---------+---------+---------+---------+---------+ 1800
       Q  L  R  R  L  Q  E  E  R  T  C  K  V  C  M  D  R  E  V  S

TATTGTGTTCATTCCGTGTGGTCATCTAGTAGTCTGCCAGGAATGTGCCCCTTCTCTAAG
1801  ------+---------+---------+---------+---------+---------+ 1860
       I  V  F  I  P  C  G  H  L  V  V  C  Q  E  C  A  P  S  L  R
```

Fig. 6 (page 5 of 6)

M-hiap-2

```
      GAAGTGCCCCATCTGCAGGGGACAATCAAGGGACTGTGCGCACATTTCTCTCATGAGT
1861  ------+---------+---------+---------+---------+---------+ 1920
       K  C  P  I  C  R  G  T  I  K  G  T  V  R  T  F  L  S  *

GAAGAATGGTCTGAAAAGTATTGTGTGGACACATCAGAAGCTGTCAGAACAAAGAATGAACTAC
1921  ------+---------+---------+---------+---------+---------+ 1980

TGATTTCAGCTCTTCAGCAGGACACATTCTACTCTCTTTCAAGATTAGTAATCTTGCTTTAT
1981  ------+---------+---------+---------+---------+---------+ 2040

GAAGGGTAGCATTGTATATTTAAGCTTAGTCTGTTGCAAGGAAGGTCTATGCTGTTGAG
2041  ------+---------+---------+---------+---------+---------+ 2100

CTACAGGACTGTGTCTGTTCCAGAGCAGGAGTTGGGATGCTTGCTGTGTATGTCCTTCAGGA
2101  ------+---------+---------+---------+---------+---------+ 2160

CTTCTTGGGATTTGGGAATTTGGGGAAAGCTTTGAATCCAGTGATGTGGAGCTCAGAAA
2161  ------+---------+---------+---------+---------+---------+ 2220

TCCTGGAACCAGTGACTCTGGTACTCAGTAGATAGGGTACCCTGTACTTCTTGGTGCTTT
2221  ------+---------+---------+---------+---------+---------+ 2280

TCCAGTCTGGGAAATAAGGAGGAATCTGCTGCTGGTAAAAATTGCTGGATGTGAGAAAT
2281  ------+---------+---------+---------+---------+---------+ 2340

AGATGAAAGTGTTTCGGGTGGGGGCCGTGCATCAGTGTAGTGTGTGCAGGGATGTATGCAG
2341  ------+---------+---------+---------+---------+---------+ 2400

GCCAAACACTGTGTAG
2401  ------+-------- 2416
```

Fig. 6 (page 6 of 6)

Alignment of BIR (Baculoviral IAP Repeats) Domains

Baculovirus
  Cp_iap    Cydia pomonella
  Op_iap    Orgyia pseudotsugata

Human
  xiap       IAP on X chromosome
  hiap1, hiap2  two different human IAP genes Mouse
  m-xiap    mouse homologue of human xiap gene Insect
  diap      Drosophilia IAP gene, not clearly a homologue of xiap or hiap note on consensus: The consensus line represents amino acids or very similar amino acids which are present in 14 of the 19 BIR sequences at each position. Capitalized residues are those that are in the consensus sequence.

```
                                         1                                                                           68
SEQ ID NO:11  Op_iap-1      kaaRlgTYtn WPvqf.leps rMAasGFYYl GrgDeVrCaf CkveitnWvr gDdpetdHkr waPqCpFV
SEQ ID NO:14  Cp_iap-1      eevRLnTFek WPvsf.lspe tMAknGFYYl GrsDeVrCaf CkveimrWke gEdpaadHkk waPqCpFV
SEQ ID NO:15  diap-2        eanRLvTFkd WPnpn.itpq aLAkAGFYYl nrlDhVkCvw CngviakWek nDnafeeHkr ffPqCprV
SEQ ID NO:16  m-xiap-1      efnRLkTFan FPsssspvsas tLArAGFLYt GegDtVqCFs ChaaidrWqy gDsavgrHrr isPnCrFI
SEQ ID NO:17  xiap-1        efnRLkTFan FPsgspvsas tLArAGFLYt GegDtVrCFs ChaavdrWqy gDsavgrHrk vsPnCrFI
SEQ ID NO:18  hiap1-1       elyRMsTYst FPagvpvser sLArAGFYYt GvnDkVkCFc CglmldnWkr gDsptekHkk lyPsCrFV
SEQ ID NO:19  hiap2-1       elyRMsTYst FPagvpvser sLArAGFYYt GvnDkVkCFc CglmldnWkl gDspiqkHkq lyPsCsFI
SEQ ID NO:20  m-xiap-2      eeaRLksFqn WPdyahltpr eLAsAGLLYt GadDqVqCFc CggklknWep cDrawseHrr hfPnCfFv
SEQ ID NO:21  xiap-2        eeaRLksFqn WPdyahltpr eLAsAGLLYt GigDqVqCFc CggklsnWep cDrawseHrr hfPnCfFv
SEQ ID NO:22  hiap1-2       enaRLlTFqt WP.llflspt dLArAGFYYi GpgDrVaCFa CggklsnWep kDnamseHlr hfPkCpFI
SEQ ID NO:23  hiap2-2       eeaRFlTYhm WP.llflsps eLArAGFYYi GpgDrVaCFa CggklsnWep kDdamseHrr hfPnCpFl
SEQ ID NO:24  m-xiap-3      yeaRivTFgt Wiysv..nke qLArAGFYal GegDkVkCFh CggglfdWkp sEdpwdqHak cyPgCkYl
SEQ ID NO:25  xiap-3        yeaRifTFgt Wiysv..nke qLArAGFYal GegDkVkCFh CggglfdWkp sEdpweqHak wyPgCkYl
SEQ ID NO:26  hiap1-3       haaRFkTFfn WPssvlvmpe qLAsAGFYYv GnsDdVkCFc CdgglrcWes gDdpwvqHak wFPrCeYl
SEQ ID NO:27  hiap2-3       haaRMrTFmy WPssvpvqpe qLAsAGFYYv GrnDdVkCFg CdgglrcWes gDdpwveHak wFPrCeFl
SEQ ID NO:28  Op_iap-2      eaaRLrTFae WPrglkqrpe eLAeAGFFYt GqgDktrCFc CdgglkdWep dDapwqqHar wydrCeYV
SEQ ID NO:29  Cp_iap-2      eaaRvksFhn WPrcmkqrpe qMAdAGFFYt GygDntkCFY CdgglkdWep eDvpweqHvr wFdrCaYV
SEQ ID NO:30  diap-3        vdaRLrTFtd WPisniqpas aLAqAGLYYq kigDqVrCFh CniglrsWqk eDepwfeHak wsPkCqFV
SEQ ID NO:31  diap-1        esvRLaTFge WPlnapvsae dLvanGFF.. -LA-AGFYY- Gtwmeaecdf ChvridrWey gDlvaerHrr ssPiCsmV
SEQ ID NO:2   Consensus     ---RL-TF-- WP-------- -LA-AGFYY- G---D-V-CF- C-------- -D-----H-- --P-C-FV
```

Fig. 7

```
                                                                    1                                                     50
cp-iap    ..........  ..........  ..........  ..........  ..........    SEQ ID NO:12
diap      ..........  ..........  ..........  ..........  mtelgMeiEs    SEQ ID NO:13
m-xiap    ..mtfnsfe   gtrtfvladt  .........   nkdeEfveEF  vRLaTfgewP    SEQ ID NO:10
xiap      ..mtfnsfe   gsktcvpadi  .........   nkeeEfveEF  lnaPVSaedL    SEQ ID NO:4
hiap1     mnivensifl  snlmksantf  elkyDLscEL  nRLkTFanFP  sssPVSastL    SEQ ID NO:6
hiap2     ..medstil   sdwtns.nkq  kmkyDFscEL  nRLkTFanFP  sgsPVSastL    SEQ ID NO:8
consensus --------    ----------  ---F-----   -RL-TF--FP  yRMsTYstFP    SEQ ID NO:44
                                              -E-         agvPVSersL
                                                          agvPVSersL
                                                          --PVS----L BIR 1
                                                                    51                                                    100
cp-iap    .vanGFFaTGk  .wleaeChfCh  .vriDrWeyGD  qvaerHrrss  PiCsmVla..
diap      ARAGFLYTGe   gDtVqCFsCh   aaiDrWqYGD   SavgrHrris  PnCrFIngFy
m-xiap    ARAGFLYTGe   gDtVrCFsCh   aavDrWqYGD   SavgrHrkvs  PnCrFIngFy
xiap      ARAGFYYTGv   nDkVkCFcCg   lmlDnWkrGD   SptekHkkly  PsCrFVqsLn
hiap1     ARAGFYYTGv   nDkVkCFcCg   lmlDnWklGD   SpiqkHkqly  PsCsFIqnLV
hiap2     ARAGF-YTG-   -D-V-CF-C-   ---D-W--GD   S-----H---  P-C-FI---
consensus 101                                                   150
cp-iap    ..........  ..........  ..........  ..........  .P nhcgnvprsq
diap      .feng aaqStnpgiq   ngqyksenCv  gnrnpfapdR
m-xiap    .lens atqStnsgiq   ngqykvenyl  gsrdhfaldR
xiap      svnnleatsq ptfpssvths  .thSlipgte   nsgyfrgsys  nspsnpvnsR
hiap1     s.aslgstsk nt..spmrns  fahSlsptle   hsslfsgsYs  slppnplnsR
hiap2     --------   ----------  ---S------   -------Y-   --------R
consensus
```

Fig. 8 (page 1 of 5)

```
                                                                    200
cp-iap      ............     ...........     .........mSD  lrl........  ..EEvRLnTF  ekWPv.sfLs
diap        esDnegnsvv       dspescscpD      lll........              EanRLvTF     kdWPn.pnit
m-xiap      ppEthadyll       rtgqvvDiSD      tiyprnp.aM    csEEARLksF  qnWPdyahLt
xiap        psEthadyll       rtgqvvDiSD      tiyprnp.aM    ycEEARLksF  qnWPdyahLt
hiap1       ang........      ........EfSa    lmrssypcpM    nnEnARLlTF  qtWP.ltfls
hiap2       avE........      .......DiSs     srtnpysyaM    stEEARFlTY  hmwP.ltfLs
consensus   --E-------       --------        ---------M    --EEARL-TF  --WP----L-

BIR 2                                    250
cp-iap      PetMAknGFY       YlGrsDeVrC      afCkveimrW    kegEdpaaDH  kkwaPqCPFV
diap        PqaLakAGFY       YlnrlDhvkC      vwCnGviakW    EknDnAfeEH  kRfFPqCPrV
m-xiap      PrELAsAGLY       YtGaddDqVqC     FcCGGKLknW    EPcDrAwSEH  rRHFPncFFV
xiap        PrELAsAGLY       YtGigDqVqC      FcCGGKLknW    EPcDrAwSEH  rRHFPncFFV
hiap1       PtDLArAGFY       YiGpgDrVaC      FaCGGKLsnW    EPkDnAmSEH  lRHFPkCPFI
hiap2       PsELArAGFY       YiGpgDrVaC      FaCGGKLsnW    EPkDdAmSEH  rRHFPnCPFl
consensus   P-ELA-AGFY       Y-G---D-V-C     F-CGGKL-NW    EP-D-A-SEH  -RHFP-CPFV BIR 3                                    300
cp-iap      kgidvcgsiv       ttnniqnttt      hdtiigPahP    kyAheaARvk  sFhnWPrcmk
diap        qmgplie.fa       tgknldelgi      qpttl.PlrP    kyAcvdARlr  TftdWPiSnI
m-xiap      lgrnvnvrse       s.gvssdrnF      pnStnsPrnP    aMAeyeARiv  TFgtWiyS..
xiap        lgrnlnirse       sdavssdrnF      pnStnlPrnP    sMAdyeARif  TFgtWiyS..
hiap1       ..........       enqlqdtsrY      tvS.....Nl    sMqthaARfk  TFfnWPsSvl
hiap2       ..........       ensl.etlrF      siS.....Nl    sMqthaARmr  TFmyWPsSvp
consensus   ----------       ----F-------    ---S----NP    -MA----AR--  TF---WP-S--
```

Fig. 8 (page 2 of 5)

BIR 3

|          | 301 |  |  |  |  | 350 |
|----------|-----|--|--|--|--|-----|
| cp-iap   | qrpEQMAdAG | FFYtGyGDnt | KCFyCdGGLk | dWepeDvPWe | QHvrWFdrCa |
| diap     | qpasaLAqAG | LYYqkiGdqv | rCFhCniGLr | sWqkeDEPWf | eHAKWsPkCq |
| m-xiap   | VnkEQLArAG | FYalGeGDkV | KCFhCgGGLt | dWkpsEDPWd | QHAKcYPgCk |
| xiap     | VnkEQLArAG | FYalGeGDkV | KCFhCgGGLt | dWkpsEDPWd | QHAKWYPgCk |
| hiap1    | VnpEQLAsAG | FYYvGnsDdV | KCFcCdGGLr | cWesgDDPWv | QHAKWFPrCe |
| hiap2    | VqpEQLAsAG | FYYvGRsDdV | KCFgCdGGLr | cWesgDDPWv | eHAKWFPrCe |
| consensus| V--EQLA-AG | FYY-G-GD-V | KCF-C-GGL- | -W---DDPW- | QHAKWFP-C- |

|          | 351 |  |  |  |  | 400 |
|----------|-----|--|--|--|--|-----|
| cp-iap   | YvqlvKGrDY | VqkVit..... | ........... | ...e....... | ........... |
| diap     | FvllaKGpaY | VseVlattaa | nassqpaTap | aptlq...... | ........... |
| m-xiap   | YLldeKGQEY | InnIhlthp. | LeEsLgrTae | kt......... | ....Ppltk |
| xiap     | YLleqKGQEY | InnIhlths. | LeEcLvrTte | kt......... | ....Psltr |
| hiap1    | YLirikGQEY | IrqVqasyph | LlEqLlsTsD | spgdenaess | iihlePgedh |
| hiap2    | FLirmKGQEF | VdeIqgryph | LlEqLlsTsD | ttgeenadpp | iihfgPgess |
| consensus| YL--KGQEY | ---------- | L-E-L--T-- | ---------- | -------P--- |

|          | 401 |  |  |  |  | 450 |
|----------|-----|--|--|--|--|-----|
| cp-iap   | ..acVLpge. | ........... | dggvVrnaiq | rKlissGcaF | stldeLlhDi |
| diap     | ..adVLmdea | pakeAltLGi | sfkdlKktme | eKIqtsGssY | lslevLIaDL |
| m-xiap   | kiDdtifqnP | mVqeAirMGF | sfkdIKkime | eKIqisGsnY | kslevLVaDL |
| xiap     | riDdtifqnP | mVqeAirMGF | srslVKqtvq | rKIlatGenY | rlvndLVlDL |
| hiap1    | seDaIMmntP | vInaAveMGF | nrdlVKqtvl | sKIlttGenY | ktvndiVsaL |
| hiap2    | seDaVMmntP | vVksAleMGF | ---------- | ---------- | ---------- |
| consensus| --D-V----P | -V--A--MGF | ----VK---- | -KI---G--Y | ----LV-DL |

Fig. 8 (page 3 of 5)

```
               451                                           500
cp-iap         ..........  ..........  ..........  ..........  ....
diap           .fddagagaal Evreppe...  ..........  ..........  ....
m-xiap         vsAqkDnteD E.........  ..........  ..........  ....
xiap           vnAqkDsmqD E.........  ..........  ..........  ....
hiap1          lnAedEireE Ererateeke sndlilirkn rmalfqhltc vipildslit
hiap2          lnAedEkreE Ekekqaeema sddlslirkn rmalfqqltc vlpildnlik
consensus      --A------- E--------- ---------- ---------- ----------

501                                           550
cp-iap         ..........  ..........  .nttvstaa pvsepipe.. ..........
diap           ..........  ..psapfie pcqattskaa svpipvadsi pakpqaaeav
m-xiap         ..........  ....ssQtsL Q.........  ..........  ..........
xiap           ..........  ....ssQtsL Q.........  ..........  ..........
hiap1          agiineqehd vikqktQtsL Qarelidtil vkgniaatvf rnslqeaeav
hiap2          anvinkqehd iikqktQipL Qarelidtiw vkgnaaanif knclkeidst
consensus      ---------- ------Q--L Q--------- ---------- ----------
```

```
                                                            Ring Zinc Finger
           551                                         600
cp-iap     ..tki.....  ..........  ..........  .Ekepq  veDskLCKIC  yveEcIvCFV
diap       sniskitdei  qkmsvstpng  ..........  nlslEEenRq  LkDarLCKVC  LDeEVgVVFl
m-xiap     ..........  ..........  .......k    diStEEQLRR  LqEEkLsKIC  MDrnIaIVFf
xiap       ..........  ..........  .......k    eiStEEQLRR  LqEEkLCKIC  MDrnIaIVFV
hiap1      lyehlfvqqd  ikyiptedvs  ..........  dlpvEEQLRR  LpEErtCKVC  MDkEVsIVFI
hiap2      lyknlfvdkn  mkyiptedvs  ..........  glSlEEQLRR  LqEErtCKVC  MDkEVsVVFI
consensus  ----------  ----------  ----------  --S-EEQLRR  L-EE-LCK-C  MD-EV--VF- 601                                         635
cp-iap     PCGHvVaCak  CAlSVdKCPM  CRkIVtsvlk  vYFS.
diap       PCGHLatCnq  CApSVanCPM  CRadIkgfvr  tFLS*
m-xiap     PCGHLatCkq  CAeaVdKCPM  CytVItfnqk  iFMS*
xiap       PCGHLVtCkg  CAeaVdKCPM  CytVItfkqk  iFMS*
hiap1      PCGHLVvCkd  CApSlrKCPi  CRstIkgtvr  tFLS*
hiap2      PCGHLVvCge  CApSlrKCPi  CRgIIkgtvr  tFLS.
consensus  PCGHLV-C--  CA-SV-KCPM  CR---I----  -FLS-
```

Alignment of RZF (Ring Zinc Finger) Domains

Baculovirus
 Cp_iap    Cydia pomonella
 Op_iap    Orgyia pseudotsugata
Human
 xiap          IAP on X chromosome
 hiap1, hiap2  two different human IAP genes
Mouse
 m-xiap    mouse homologue of human xiap gene
Insect
 diap      Drosophila IAP gene, not clearly a homologue of xiap or hiap note on consensus: The consensus line represents amino acids or very similar amino acids which are present in 6 of the 7 RZF sequences at each position. Capitalized residues are those that are in the consensus sequence.

```
                           1                                              46
SEQ ID NO:32  hiap2      EqlrrlqEer  tCKVCMdkev  sVvFlPCGHl  vvCgeCApel  rkCPiC
SEQ ID NO:33  hiap1      EqltrlpEer  tCKVCMdkev  sIvFlPCGHl  w CkdCApsl  rkCPiC
SEQ ID NO:34  m-xiap     EqltrlqEek  lsKICMdrni  aIvFfPCGHl  atCkqCAeav  dkCPmC
SEQ ID NO:35  xiap       EqltrlqEek  lCKICMdrni  aIvFvPCGHl  vtCkqCAeav  dkCPmC
SEQ ID NO:36  diap       EenrglkDar  lCKVCLdeev  gVvFlPCGHl  atCnqCApev  anCPmC
SEQ ID NO:37  Cp_iap     EkepgveDsk  lCKICyveec  iVcFvPCGHv  vaCakCAlsv  dkCPmC
SEQ ID NO:38  Op_iap     aveaevaDdr  lCKICIgack  tVcFvPCGHv  vaCgkCAagv  tTCPvC
SEQ ID NO:1   consensus  E-----E--   -CKICM----  -V-F-PCGH-  --C--CA---  --CP-C
```

Fig. 9

MAMMALIAN IAP GENE FAMILY, PRIMERS, PROBES, AND DETECTION METHODS

This application is a continuation-in-part of U.S. application Ser. No. 08/511,485 filed Aug. 4, 1995, U.S. Pat. No. 5,919,912.

BACKGROUND OF THE INVENTION

There are two general ways by which cells die. An easily recognized pathway is necrosis, a process of cell death usually resulting from severe and sudden injury. In necrosis, changes in cellular homeostasis occur with loss of membrane integrity. Dysregulation of osmotic pressure results and, as a consequence, the cells swell and finally rupture. The cellular contents are then spilled into the surrounding tissue space and, usually, an inflammation response ensues. A second form of cell death is apoptosis. This cell "suicide" pathway or programmed cell death often occurs so rapidly that in some biological systems the apoptotic process is difficult to ascertain. Indeed, it has been only in the past few years that the involvement of apoptosis in a wide spectrum of biological processes has become recognized. Apoptosis is a fundamental physiological pathway of cell death, highly conserved throughout evolution, and playing a major role in development, viral pathogenesis, cancer, autoimmune diseases and neurodegenerative disorders.

Inappropriate increases in apoptosis may cause or contribute to a variety of diseases, including AIDS, neurodegenerative diseases (e.g. Alzheimer's Disease, Parkinson's Disease, Amyotrophic Lateral Sclerosis (ALS), retinitis pigmentosa and other diseases of the retina, myelodysplastic syndrome (e.g., aplastic anemia), toxin-induced liver disease (e.g., alcoholism) and ischemic injury (e.g., myocardial infarction, stroke, and reperfusion injury). In addition, disruption of normally occurring apoptosis has been implicated in the development of some cancers (e.g. follicular lymphoma, p53 carcinomas, and hormone dependent tumors), autoimmune disorders (e.g., lupus erythematosis and multiple sclerosis) and viral infections (e.g., herpes virus, poxvirus, and adenovirus infections).

Mature $CD4^+$ T-lymphocytes in patients with HIV-1 have been observed to respond to stimulation with mitogens or super-antigens by undergoing increased apoptosis. The great majority of these cells are not infected and similar inappropriate antigen-induced apoptosis could be very important in the destruction of this vital part of the immune system early in HIV infection.

Baculoviruses encode inhibitors of apoptosis proteins (IAPs). These proteins inhibit the apoptosis which otherwise occurs when insect cells are infected by the virus. Baculovirus IAP proteins work in a manner which is thought to be independent of other viral proteins. The baculovirus IAP genes include sequences encoding a ring zinc finger-like motif which is presumed to be involved in the direct binding of DNA.

SUMMARY OF THE INVENTION

In general, the invention features substantially pure DNA (for example, genomic DNA, cDNA, or synthetic DNA) encoding a mammalian IAP polypeptide as defined below. In related aspects, the invention also features a vector, a cell (e.g., a mammalian, yeast or bacterial cell), and a transgenic animal or embryo thereof which includes such a substantially pure DNA encoding an IAP polypeptide.

In preferred embodiments, an IAP gene is the xiap (including human xiap and its murine homolog, m-xiap), hiap1 (including human hiap1 and m-hiap1), or the hiap2 gene (including human hiap2 and m-hiap2). In most preferred embodiments the IAP gene is a human IAP gene. In other various preferred embodiments, the cell is a transformed cell. In related aspects, the invention features a transgenic animal containing a transgene which encodes an IAP polypeptide that is expressed in or delivered to tissue normally susceptible to apoptosis.

In yet another aspect, the invention features DNA encoding fragments of IAP polypeptides including the BIR domains and the RZF domains provided herein.

In specific embodiments, the invention features DNA sequences substantially identical to the DNA sequences shown in FIGS. 1–6.

In another aspect, the invention also features RNA which is encoded by the DNA described herein. Preferably, the RNA is mRNA. In another embodiment the RNA is antisense RNA.

In another aspect, the invention features a substantially pure polypeptide having a sequence substantially identical to one of the IAP amino acid sequences shown in FIGS. 1–6.

In a second aspect, the invention features a substantially pure DNA which includes a promoter capable of expressing the IAP gene in a cell susceptible to apoptosis. In preferred embodiments, the IAP gene is xiap (including the human or murine xiap), hiap1 (preferably the human or murine hiap1), or hiap2 (preferably the human or murine hiap2). hiap2 may be the full length gene, as shown in FIG. 3, or the truncated variant having the sequence boxed in FIG. 3 deleted.

In preferred embodiments, the promoter is the promoter native to an IAP gene. Additionally, transcriptional and translational regulatory regions are preferably native to an IAP gene.

In another aspect, the invention provides transgenic cell lines and transgenic animals. The transgenic cells of the invention are preferably cells which are susceptible to apoptosis. In preferred embodiments, the transgenic cell is a fibroblast, neuronal cell, a lymphocyte cell, or an insect cell. Most preferably, the neuron is a motor neuron and the lymphocyte is a $CD4^+$ T-cell.

In another aspect, the invention features a method of inhibiting apoptosis which involves producing a transgenic cell having a transgene encoding an IAP polypeptide wherein the transgene is integrated into the genome of the cell and is positioned for expression in the cell and wherein the IAP transgene is expressed in the cell at a level sufficient to inhibit apoptosis.

In a related aspect, the invention features a transgenic animal, preferably a mammal, more preferably a rodent, and most preferably a mouse, having either increased copies of IAP genes inserted into the genome or a knockout of an IAP gene in the genome. The transgenic animals may express an increased amount of IAP polypeptide or may express a decreased amount of an IAP polypeptide, respectively. In related embodiments, the invention provides a method of utilizing the IAP nucleic acid to engineer a knockout mutation in an IAP gene and a method of making an animal with increased expression by insertion of IAP gene into the genome.

In another aspect, the invention features a method of detecting an IAP in a cell involving: (a) contacting the IAP gene or a portion thereof greater than 9 nucleic acids, preferably greater than 18 nucleic acids in length with a preparation of genomic DNA from the cell under hybridization conditions providing detection of DNA sequences having about 50% or greater nucleotide sequence identity to the amino acid encoding DNA sequences of hiap1, hiap2, or xiap IAP polypeptides.

In another aspect, the invention features a method of producing an IAP polypeptide which involves: (a) providing a cell transformed with DNA encoding an IAP polypeptide positioned for expression in the cell; (b) culturing the cell under conditions for expressing the DNA; and (c) isolating the IAP polypeptide. In preferred embodiments the IAP polypeptide is expressed by DNA which has a constitutive or inducible promotor. In our embodiment, the promotor is a heterologous promotor.

In another aspect, the invention features substantially pure mammalian IAP polypeptide. Preferably, the polypeptide includes a greater than 50 amino acid sequence substantially identical to a greater than 50 amino acid sequence shown in any one of FIGS. 1–4. Most preferably, the polypeptide is the human or murine XIAP, HIAP1, or HIAP2 polypeptide. Fragments including BIR domains and RZF-domains provided herein are also a part of the invention.

In another aspect, the invention features a recombinant mammalian polypeptide capable of modulating apoptosis wherein the polypeptide includes at least a ring zinc finger domain and a BIR domain as defined herein. In preferred embodiments, the invention features a substantially pure polypeptide and an oligonucleotide encoding said polypeptide, the polypeptide including a ring zinc finger (RZF) having the sequence:

Glu Xaa1 Xaa1 Xaa1 Xaa1 Xaa1 Xaa1 Xaa2 Xaa1 Xaa1 Xaa1 Cys Lys Xaa3 Cys Met Xaa1 Xaa1 Xaa1 Xaa1 Xaa1 Xaa3 Xaa1 Phe Xaa1 Pro Cys Gly His Xaa1 Xaa1 Xaa1 Cys Xaa1 Xaa1 Cys Ala Xaa1 Xaa1 Xaa1 Xaa1 Xaa1 Cys Pro Xaa1 Cys, wherein Xaa1 is any amino acid, Xaa2 is Glu or Asp, Xaa3 is Val or Ile (SEQ ID NO:1); and at least one BIR domain having the sequence: Xaa1 Xaa1 Xaa1 Arg Leu Xaa1 Thr Phe Xaa1 Xaa1 Trp Pro Xaa2 Xaa1 Xaa1 Xaa2 Xaa2 Xaa1 Xaa1 Xaa1 Xaa1 Leu Ala Xaa1 Ala Gly Phe Tyr Tyr Xaa1 Gly Xaa1 Xaa1 Asp Xaa1 Val Xaa1 Cys Phe Xaa1 Cys Xaa1 Xaa1 Xaa1 Xaa1 Xaa1 Xaa1 Trp Xaa1 Xaa1 Xaa1 Asp Xaa1 Xaa1 Xaa1 Xaa1 Xaa1 His Xaa1 Xaa1 Xaa1 Xaa1 Pro Xaa1 Cys Xaa1 Phe Val, wherein Xaa1 may be any amino acid and Xaa2 may be any amino acid or may be absent (SEQ ID NO:2).

In various preferred embodiments the protein has at least two or, more preferably at least three BIR domains, the RZF domain has one of the IAP sequences shown in FIG. 6, and the BIR domains are comprised of BIR domains shown in FIG. 5. In other preferred embodiments the BIR domains are at the amino terminal end of the protein relative to the RZF domain, which is at or near the carboxy terminus of the polypeptide.

In another aspect, the invention features an IAP gene isolated according to the method involving: (a) providing a sample of DNA; (b) providing a pair of oligonucleotides having sequence homology to a conserved region of an IAP gene; (c) combining the pair of oligonucleotides with the cell DNA sample under conditions suitable for polymerase chain reaction-mediated DNA amplification; and (d) isolating the amplified IAP gene or fragment thereof.

In preferred embodiments, the amplification is carried out using a reverse-transcription polymerase chain reaction, for example, the RACE method.

In another aspect, the invention features an IAP gene isolated according to the method involving: (a) providing a preparation of DNA; (b) providing a detectably-labelled DNA sequence having homology to a conserved region of an IAP gene; (c) contacting the preparation of DNA with the detectably-labelled DNA sequence under hybridization conditions providing detection of genes having 50% or greater nucleotide sequence identity; and (d) identifying an IAP gene by its association with the detectable label.

In another aspect, the invention features an IAP gene isolated according to the method involving: (a) providing a cell sample; (b) introducing by transformation into the cell sample a candidate IAP gene; (c) expressing the candidate IAP gene within the cell sample; and (d) determining whether the cell sample exhibits an altered apoptotic response, whereby a response identifies an IAP gene.

In another aspect, the invention features a method of identifying an IAP gene in a cell, involving: (a) providing a preparation of cellular DNA (for example, from the human genome or a cDNA library (such as a cDNA library isolated from a cell type which undergoes apoptosis); (b) providing a detectably-labelled DNA sequence (for example, prepared by the methods of the invention) having homology to a conserved region of an IAP gene; (c) contacting the preparation of cellular DNA with the detectably-labelled DNA sequence under hybridization conditions providing detection of genes having 50% nucleotide or greater sequence identity; and (d) identifying an IAP gene by its association with the detectable label.

In another aspect, the invention features a method of isolating an IAP gene from a recombinant library, involving: (a) providing a recombinant library; (b) contacting the library with a detectably-labelled gene fragment produced according to the PCR method of the invention under hybridization conditions providing detection of genes having 50% or greater nucleotide sequence identity; and (c) isolating an IAP gene by its association with the detectable label.

In another aspect, the invention features a method of identifying an IAP gene involving: (a) providing a cell tissue sample; (b) introducing by transformation into the cell sample a candidate IAP gene; (c) expressing the candidate IAP gene within the cell sample; and (d) determining whether the cell sample exhibits inhibition of apoptosis, whereby a change in (i.e. modulation of) apoptosis identifies an IAP gene.

Preferably, the cell sample is a cell type which may be assayed for apoptosis (e.g., lymphocytes, T-cells and B-cells, neuronal cells, baculovirus infected insect cells and fibroblast cells); the candidate IAP gene is obtained from a cDNA expression library; and the apoptosis response is the inhibition of apoptosis.

In another aspect, the invention features a method of inhibiting apoptosis in a mammal wherein the method includes: (a) providing DNA encoding at least one IAP polypeptide to a cell which is susceptible to apoptosis; wherein the DNA is integrated into the genome of the cell and is positioned for expression in the cell; and the IAP gene is under the control of regulatory sequences suitable for controlled expression of the gene(s); wherein the IAP transgene is expressed at a level sufficient to inhibit apoptosis relative to a cell lacking the IAP transgene. It will be appreciated that IAP polypeptides also may be administered directly to inhibit any undesirable apoptosis.

In a related aspect, the invention features a method of inhibiting apoptosis wherein the method involves: (a) producing a cell having integrated in the genome a transgene containing the IAP gene under the control of a promoter providing constitutive expression of the IAP gene.

In yet another related aspect, the invention features a method of inhibiting apoptosis wherein the method involves: (a) producing a cell having integrated in the genome a transgene containing the IAP gene under the control of a promoter providing controllable expression of the IAP gene; and (b) regulating the environment of the cell so that the IAP transgene is controllably expressed in the cell. In preferred embodiments, the IAP gene is expressed using a tissue-specific or cell type-specific promoter, or by a promoter that is activated by the introduction of an external signal or agent, such as a chemical signal or agent. In preferred embodiments the cell is a lymphocyte or B-cell, a neuronal cell, or a fibroblast. In other embodiments the cell is a cell in an HIV infected human, or a mammal with a neurodegenerative disease, ischemia, toxin induced liver disease, or a myelodysplastic syndrome.

In a related aspect, the invention provides a method of inhibiting apoptosis in a mammal by providing an apoptosis-inhibiting amount of IAP polypeptide.

In another aspect, the invention features a purified antibody which binds specifically to an IAP family protein. Such an antibody may be used in any standard immunodetection method for the identification of an IAP polypeptide. Preferably, the antibody binds specifically to xiap, hiap1 or hiap2. In various embodiments the antibody may react with other IAP polypeptides or may be specific for one or a few IAP polypeptides. The antibody may be a monoclonal polyclonal antibody. Preferably, the antibody reacts specifically with only one of the IAP polypeptides, for example, reacts with murine and human xiap, but not with hiap1 or hiap2 from mammalian species.

In another aspect, the invention features a method of identifying a compound which modulates apoptosis. The method includes (a) providing a cell expressing an IAP polypeptide; and (b) contracting the cell with a candidate compound, and monitoring the expression of an IAP gene. An alteration in the level of expression of the IAP gene indicates the presence of a compound which modulates apoptosis. The compound may be an inhibitor or an enhancer of apoptosis. In various preferred embodiments, the cell is a fibroblast, a neuronal cell, a lymphocyte (T-cell or B-cell), or an insect cell; the polypeptide expression being monitored is XIAP, HIAP1, or HIAP2 (e.g., human or murine).

In a related aspect, the invention features methods of detecting compounds which modulate apoptosis using the interaction trap technology and IAP polypeptides or fragments thereof as a component of the bait. In preferred embodiments, the compound being tested as a modulator of apoptosis is also a polypeptide.

In another aspect, the invention features a method for diagnosing a cell proliferation disease, or an increased liklihood of such a disease, using an IAP nucleic acid probe or antibody. Preferably, the disease is a cancer. Most preferably, the disease is selected from the group consisting of promyelocytic leukemia, a Hela-type carcinoma, chronic myelogenous leukemia (preferably using xiap or hiap2 related probes), lymphoblastic leukemia (preferably using a xiap related probe), Burkitt's lymphoma (preferably using an hiap1 related probe), colorectal adenocarcinoma, lung carcinoma, and melanoma (preferably using a xiap probe). Preferably, a diagnosis is indicated by a 2-fold increase in expression or activity, more preferably, at least a 10-fold increase in expression or activity.

By "IAP gene" is meant a gene encoding a polypeptide having at least one BIR domain and a ring zinc finger domain which is capable of modulating (inhibiting or enhancing) apoptosis in a cell or tissue when provided by other intracellular or extracellular delivery methods. In preferred embodiments the IAP gene is a gene having about 50% or greater nucleotide sequence identity to at least one of the IAP amino acid encoding sequences of FIGS. 1–4 or portions thereof. Preferably, the region of sequence over which identity is measured is a region encoding at least one BIR domain and a ring zinc finger domain. Mammalian IAP genes include nucleotide sequences isolated from any mammalian source. Preferably, the mammal is a human.

By an "IAP gene" is also meant any member of the family of apoptosis inhibitory genes characterized by their ability to modulate apoptosis and having at least 20%, preferably 30%, and most preferably 50% amino acid sequence identity to at least one of the conserved regions of one of the IAP members described herein (i.e., either the BIR or ring zinc finger domains from the human or murine xiap, hiap1 and hiap2). Representative members of the IAP gene family include, without limitation, the human and murine xiap, hiap1, and hiap2 genes. By "IAP protein" is meant a polypeptide encoded by an IAP gene.

By "BIR domain" is meant a domain having the amino acid sequence of the consensus sequence: Xaa1 Xaa1 Xaa1 Arg Leu Xaa1 Thr Phe Xaa1 Xaa1 Trp Pro Xaa2 Xaa1 Xaa1 Xaa2 Xaa2 Xaa1 Xaa1 Xaa1 Xaa1 Leu Ala Xaa1 Ala Gly Phe Tyr Tyr Xaa1 Gly Xaa1 Xaa1 Asp Xaa1 Val Xaa1 Cys Phe Xaa1 Cys Xaa1 Xaa1 Xaa1 Xaa1 Xaa1 Xaa1 Trp Xaa1 Xaa1 Xaa1 Asp Xaa1 Xaa1 Xaa1 Xaa1 Xaa1 His Xaa1 Xaa1 Xaa1 Xaa1 Pro Xaa1 Cys Xaa1 Phe Val, wherein Xaa1 is any amino acid and Xaa2 is any amino acid or is absent (SEQ ID NO:2). Preferably, the sequence is substantially identical to one of the BIR domain sequences provided for xiap, hiap1, hiap2 herein.

By "ring zinc finger" or "RZF" is meant a domain having the amino acid sequence of the consensus sequence: Glu Xaa1 Xaa1 Xaa1 Xaa1 Xaa1 Xaa1 Xaa2 Xaa1 Xaa1 Xaa1 Cys Lys Xaa3 Cys Met Xaa1 Xaa1 Xaa1 Xaa1 Xaa1 Xaa3 Xaa1 Phe Xaa1 Pro Cys Gly His Xaa1 Xaa1 Xaa1 Cys Xaa1 Xaa1 Cys Ala Xaa1 Xaa1 Xaa1 Xaa1 Xaa1 Cys Pro Xaa1 Cys, wherein Xaa1 is any amino acid, Xaa2 is Glu or Asp, and Xaa3 is Val or Ile (SEQ ID NO:1). Preferably, the sequence is substantially identical to the RZF domains provided herein for the human or murine xiap, hiap1, or hiap2.

By "modulating apoptosis" or "altering apoptosis" is meant increasing or decreasing the number of cells which undergo apoptosis in a given cell population. Preferably, the cell population is selected from a group including T-cells, neuronal cells, fibroblasts, or any other cell line known to undergo apoptosis in a laboratory setting (e.g., the baculovirus infected insect cells). It will be appreciated that the degree of modulation provided by an IAP or modulating compound in a given assay will vary, but that one skilled in the art can determine the statistically significant change in the level of apoptosis which identifies an IAP or a compound which modulates an IAP.

By "inhibiting apoptosis" is meant any decrease in the number of cells which undergo apoptosis relative to an untreated control. Preferably, the decrease is at least 25%, more preferably the decrease is 50%, and most preferably the decrease is at least one-fold.

By "polypeptide" is meant any chain of amino acids, regardless of length or post-translational modification (e.g., glycosylation or phosphorylation).

By "substantially identical" is meant a polypeptide or nucleic acid exhibiting at least 50%, preferably 85%, more preferably 90%, and most preferably 95% homology to a reference amino acid or nucleic acid sequence. For polypeptides, the length of comparison sequences will generally be at least 16 amino acids, preferably at least 20 amino acids, more preferably at least 25 amino acids, and most preferably 35 amino acids. For nucleic acids, the length of comparison sequences will generally be at least 50 nucleotides, preferably at least 60 nucleotides, more preferably at least 75 nucleotides, and most preferably 110 nucleotides.

Sequence identity is typically measured using sequence analysis software (e.g., Sequence Analysis Software Package of the Genetics Computer Group, University of Wisconsin Biotechnology Center, 1710 University Avenue, Madison, Wis. 53705). Such software matches similar sequences by assigning degrees of homology to various substitutions, deletions, and other modifications. Conservative substitutions typically include substitutions within the following groups: glycine, alanine, valine, isoleucine, leucine; aspartic acid, glutamic acid, asparagine, glutamine; serine, threonine; lysine, arginine; and phenylalanine, tyrosine.

By a "substantially pure polypeptide" is meant an IAP polypeptide which has been separated from components which naturally accompany it. Typically, the polypeptide is substantially pure when it is at least 60%, by weight, free from the proteins and naturally-occurring organic molecules with which it is naturally associated. Preferably, the preparation is at least 75%, more preferably at least 90%, and most preferably at least 99%, by weight, IAP polypeptide. A substantially pure IAP polypeptide may be obtained, for example, by extraction from a natural source (e.g., a fibroblast, neuronal cell, or lymphocyte cell); by expression of a recombinant nucleic acid encoding an IAP polypeptide; or by chemically synthesizing the protein. Purity can be measured by any appropriate method, e.g., those described in column chromatography, polyacrylamide gel electrophoresis, or by HPLC analysis.

A protein is substantially free of naturally associated components when it is separated from those contaminants which accompany it in its natural state. Thus, a protein which is chemically synthesized or produced in a cellular system different from the cell from which it naturally originates will be substantially free from its naturally associated components. Accordingly, substantially pure polypeptides include those derived from eukaryotic organisms but synthesized in E. coli or other prokaryotes.

By "substantially pure DNA" is meant DNA that is free of the genes which, in the naturally-occurring genome of the organism from which the DNA of the invention is derived, flank the gene. The term therefore includes, for example, a recombinant DNA which is incorporated into a vector; into an autonomously replicating plasmid or virus; or into the genomic DNA of a prokaryote or eukaryote; or which exists as a separate molecule (e.g., a cDNA or a genomic or cDNA fragment produced by PCR or restriction endonuclease digestion) independent of other sequences. It also includes a recombinant DNA which is part of a hybrid gene encoding additional polypeptide sequence.

By "transformed cell" is meant a cell into which (or into an ancestor of which) has been introduced, by means of recombinant DNA techniques, a DNA molecule encoding (as used herein) an IAP polypeptide.

By "transgene" is meant any piece of DNA which is inserted by artifice into a cell, and becomes part of the genome of the organism which develops from that cell. Such a transgene may include a gene which is partly or entirely heterologous (i.e., foreign) to the transgenic organism, or may represent a gene homologous to an endogenous gene of the organism.

By "transgenic" is meant any cell which includes a DNA sequence which is inserted by artifice into a cell and becomes part of the genome of the organism which develops from that cell. As used herein, the transgenic organisms are generally transgenic mammalian (e.g., rodents such as rats or mice) and the DNA (transgene) is inserted by artifice into the nuclear genome.

By "transformation" is meant any method for introducing foreign molecules into a cell. Lipofection, calcium phosphate precipitation, retroviral deliver, electroporation and biolistic transformation are just a few of the teachings which may be used. For example, Biolistic transformation is a method for introducing foreign molecules into a cell using velocity driven microprojectiles such as tungsten or gold particles. Such velocity-driven methods originate from pressure bursts which include, but are not limited to, helium-driven, air-driven, and gunpowder-driven techniques. Biolistic transformation may be applied to the transformation or transfection of a wide variety of cell types and intact tissues including, without limitation, intracellular organelles (e.g., and mitochondria and chloroplasts), bacteria, yeast, fungi, algae, animal tissue, and cultured cells.

By "positioned for expression" is meant that the DNA molecule is positioned adjacent to a DNA sequence which directs transcription and translation of the sequence (i.e., facilitates the production of, e.g., an IAP polypeptide, a recombinant protein or a RNA molecule).

By "reporter gene" is meant a gene whose expression may be assayed; such genes include, without limitation, β-glucuronidase (GUS), luciferase, chloramphenicol transacetylase (CAT), and β-galactosidase.

By "promoter" is meant minimal sequence sufficient to direct transcription. Also included in the invention are those promoter elements which are sufficient to render promoter-dependent gene expression controllable for cell-type specific, tissue-specific or inducible by external signals or agents; such elements may be located in the 5' or 3' regions of the native gene.

By "operably linked" is meant that a gene and a regulatory sequence(s) are connected in such a way as to permit gene expression when the appropriate molecules (e.g., transcriptional activator proteins) are bound to the regulatory sequence(s).

By "conserved region" is meant any stretch of six or more contiguous amino acids exhibiting at least 30%, preferably 50%, and most preferably 70% amino acid sequence identity between two or more of the IAP family members, (e.g., between human HIAP1, HIAP2, and XIAP). Examples of preferred conserved regions are shown (as boxed or designated sequences) in FIGS. 5–7 and Tables 1 and 2, and include, without limitation, BIR domains and ring zinc finger domains.

By "detectably-labelled" is meant any means for marking and identifying the presence of a molecule, e.g., an oligonucleotide probe or primer, a gene or fragment thereof, or a cDNA molecule. Methods for detectably-labelling a molecule are well known in the art and include, without limitation, radioactive labelling (e.g., with an isotope such as $^{32}P$ or $^{35}S$) and nonradioactive labelling (e.g., chemiluminescent labelling, e.g., fluorescein labelling).

By "purified antibody" is meant antibody which is at least 60%, by weight, free from proteins and naturally-occurring organic molecules with which it is naturally associated.

Preferably, the preparation is at least 75%, more preferably 90%, and most preferably at least 99%, by weight, antibody, e.g., an IAP specific antibody. A purified antibody may be obtained, for example, by affinity chromatography using recombinantly-produced protein or conserved motif peptides and standard techniques.

By "specifically binds" is meant an antibody which recognizes and binds a protein but which does not substantially recognize and bind other molecules in a sample, e.g., a biological sample, which naturally includes protein.

Other features and advantages of the invention will be apparent from the following description of the preferred embodiments thereof, and from the claims.

DETAILED DESCRIPTION

The drawings will first be described.

DRAWINGS

FIG. 1 is the human xiap cDNA sequence and the XIAP polypeptide sequence (SEQ ID NOS:3, 4).

FIG. 2 is the human hiap1 cDNA sequence and the HIAP1 polypeptide sequence (SEQ ID NOS:5, 6).

FIG. 3 is the human hiap2 cDNA sequence and the HIAP2 polypeptide sequence (SEQ ID NOS:7, 8). The sequence absent in the hiap2-G variant is boxed.

FIG. 4 is the murine xiap cDNA sequence and encoded murine XIAP polypeptide sequence (SEQ ID NOS:9, 10).

FIG. 5 is the murine hiap1 cDNA sequence and the encoded murine HIAP1 polypeptide sequence (SEQ ID NOS:39, 40).

FIG. 6 is the murine hiap2 cDNA sequence and the encoded murine HIAP2 polypeptide SEQ ID NOS:41, 42).

FIG. 7 shows the alignment of the BIR domains of IAP proteins (SEQ ID NOS: 11 and 14–31).

FIG. 8 is the alignment of human IAP polypeptides with diap, cp-iap, and the consensus sequence (SEQ ID NOS:4, 6, 8, 10, 12, and 13).

FIG. 9 shows the alignment of the Ring Zinc Finger domains of IAP proteins (SEQ ID NOS: 32–38).

Figure 10A:
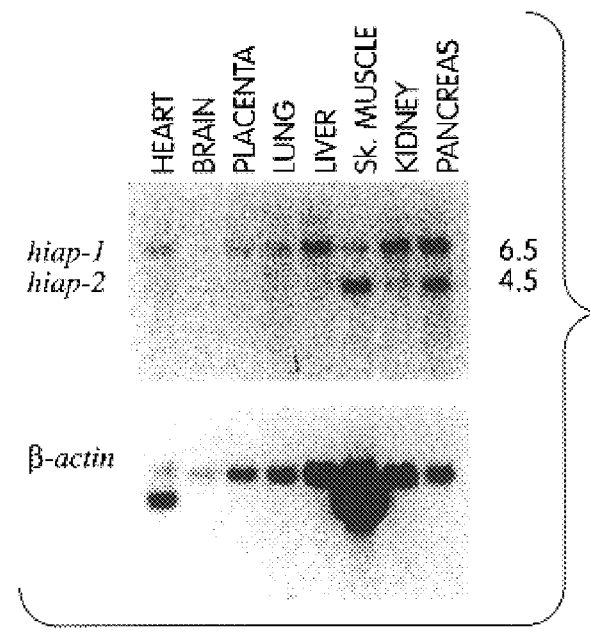
Figure 10B:
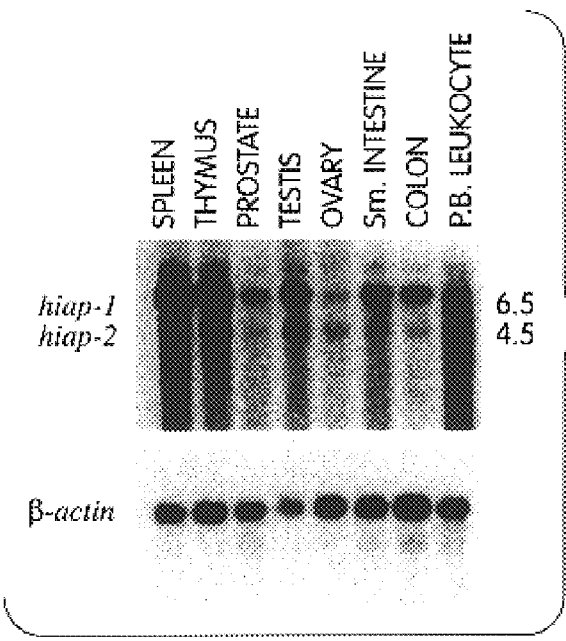
Figure 10C:

FIGS. 10A–C are a series of Northern blots showing human hiap1 and hiap2 mRNA expression in human tissues.

Figure 11A:
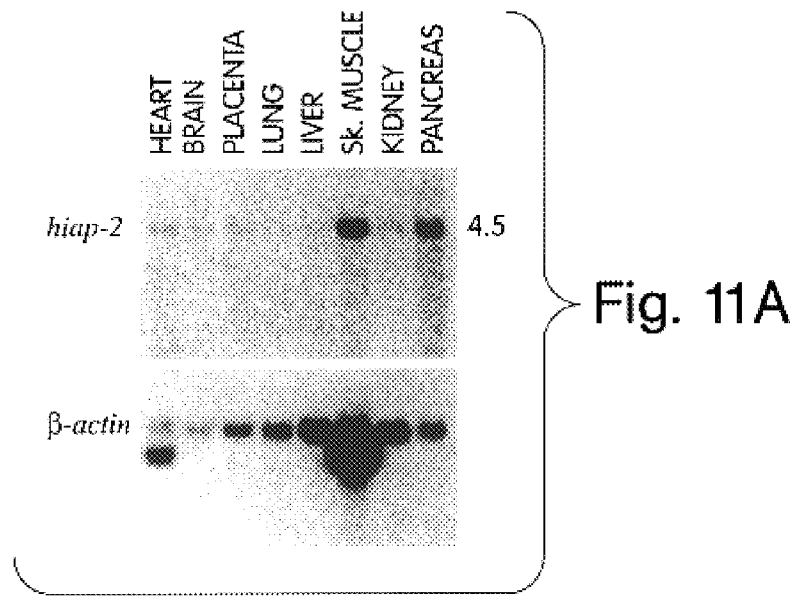
Figure 11B:
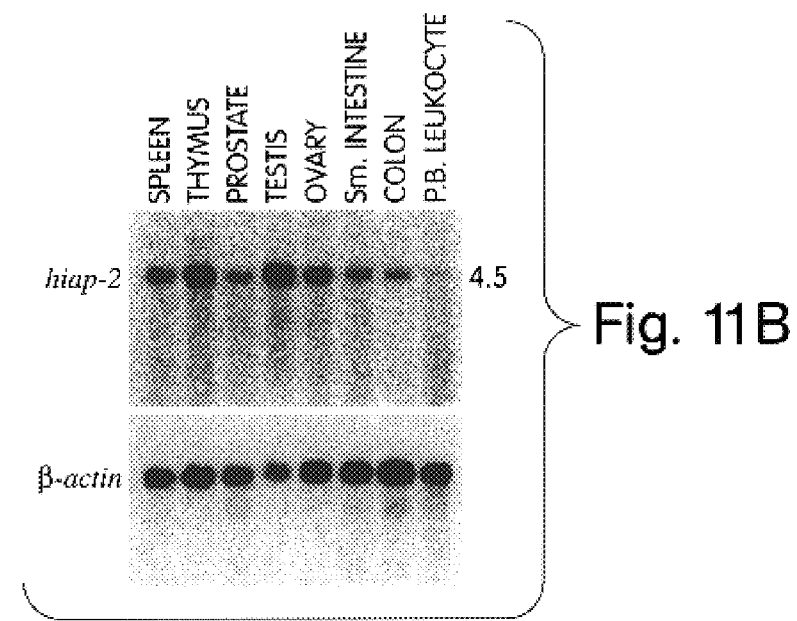
Figure 11C:
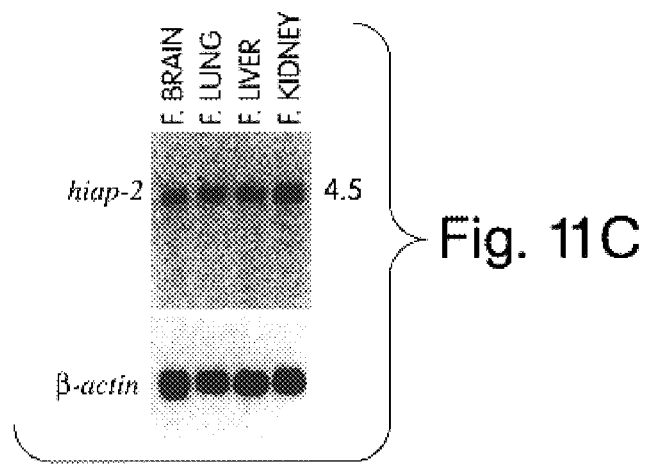

FIGS. 11A–C are a series of Northern blots showing human hiap2 mRNA expression in human tissues.

Figure 12A:
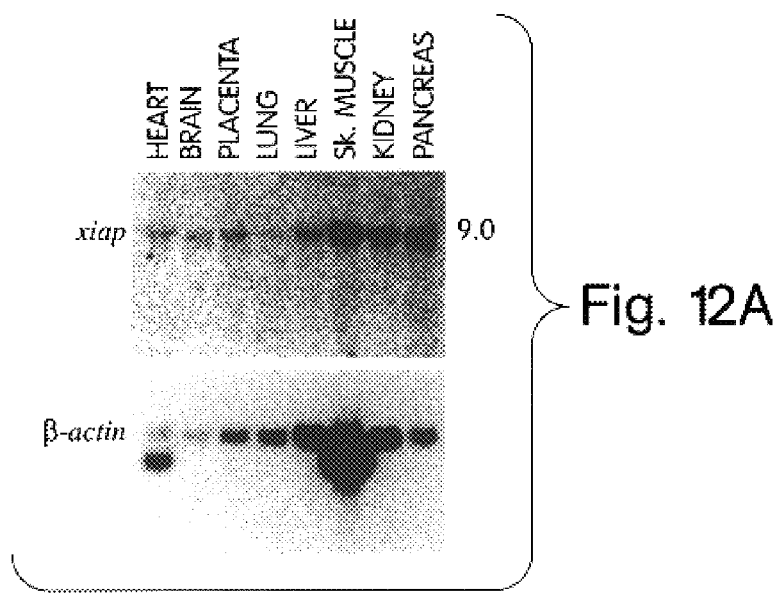
Figure 12B:
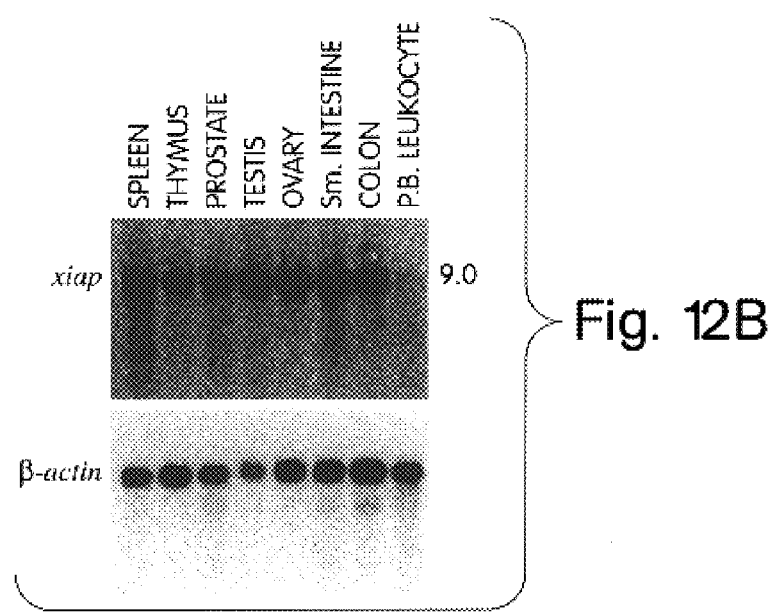
Figure 12C:
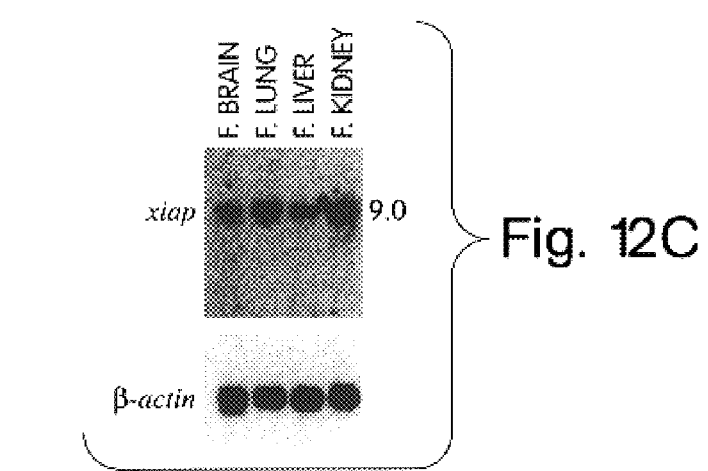

FIGS. 12A–C are a series of Northern blots showing human xiap mRNA expression in human tissues.

Figure 13A:
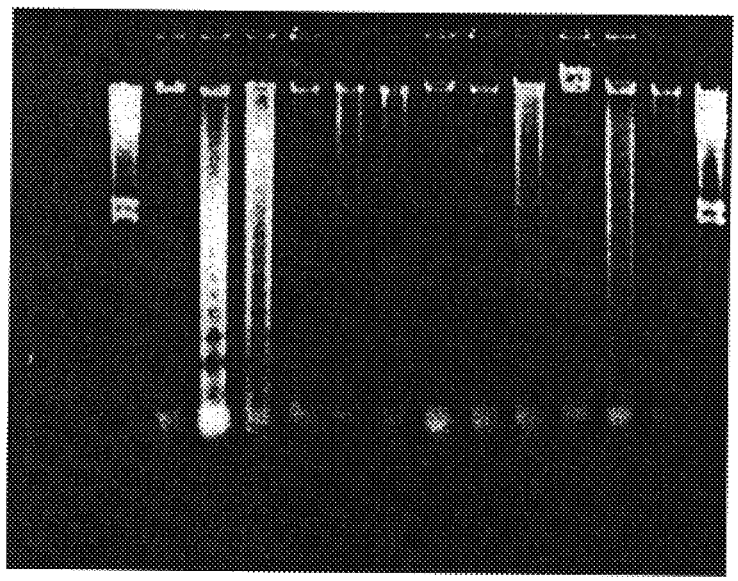
Figure 13B:
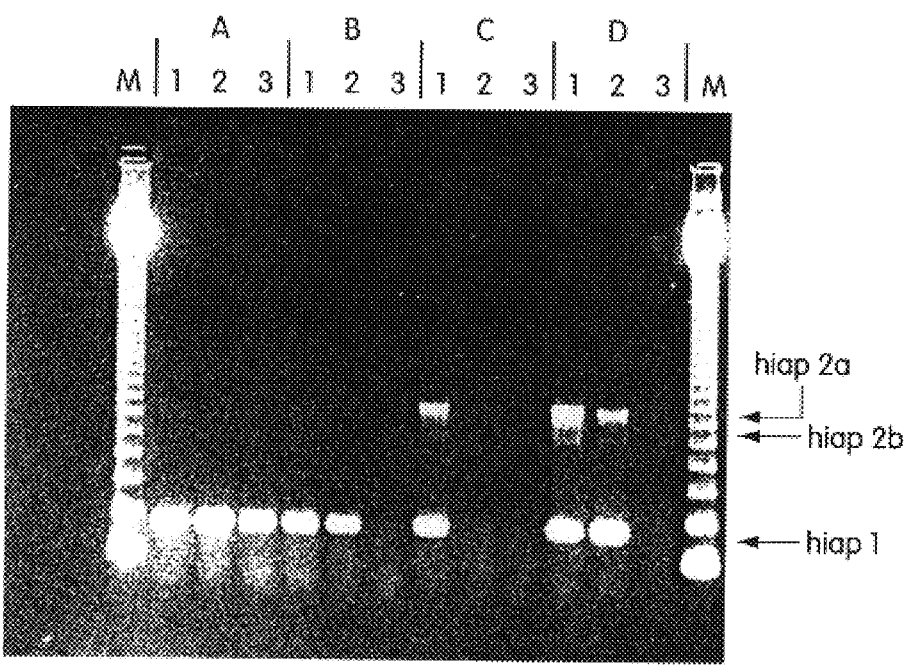

FIGS. 13A and 13B are agarose gels showing apoptic DNA ladders and RT PCR products using hiap1 and hiap2 specific probes in HIV infected T cells.

FIGS. 14A–14D are graphs showing apoptosis suppression by XIAP, HIAP1, HIAP2, bcl-2m, smn and 6-myc.

I. IAP Polypeptides and Genes Encoding IAP Polypeptides

We have discovered a new class of mammalian proteins which modulate apoptosis (IAPs) and the genes which encode these proteins. The IAP proteins are characterized by the presence of a ring zinc finger (RZF) domain (FIG. 9) and at least one BIR domain as defined by the boxed consensus sequences in FIGS. 7 and 8 and by the sequence domains provided in Tables 1 and 2. As examples of the IAP proteins we provide the cDNA sequences and amino acid sequences for these new human and murine apoptosis inhibitors, HIAP1, HIAP2, and XIAP. Additional members of the mammalian IAP family (including homologs from other species and mutant sequences) may be isolated using standard cloning techniques and the conserved amino acid sequences, primers and probes provided herein and known in the art.

This application is related to U.S. Ser. No. 08/511,485, filed Aug. 4, 1995, U.S. Pat. No. 5,919,912. U.S. Ser. No. 08/511,485 is hereby incorporated by reference.

TABLE 1

NUCLEOTIDE POSITION OF CONSERVED DOMAINS*

|  | BIR-1 | BIR-2 | BIR-3 | Ring Zinc Finger |
| --- | --- | --- | --- | --- |
| h-xiap | 109–312 | 520–723 | 826–1023 | 1348–1485 |
| m-xiap | 202–405 | 613–816 | 916–1113 | 1438–1575 |
| h-hiap1 | 273–476 | 693–893 | 951–1154 | 1824–1961 |
| m-hiap1 | 251–453 | 670–870 | 928–1131 | 1795–1932 |
| h-hiap2 | 373–576 | 787–987 | 1042–1245 | 1915–2052 |
| m-hiap2 | 215–418 | 608–808 | 863–1066 | 1763–1876 |

*Positions indicate correspond to those shown in FIGS. 1–4.

TABLE 2

AMINO ACID POSITION OF CONSERVED DOMAINS*

|  | BIR-1 | BIR-2 | BIR-3 | Ring Zinc Finger |
| --- | --- | --- | --- | --- |
| h-Xiap | 26–93 | 163–230 | 265–330 | 439–484 |
| m-Xiap | 26–93 | 163–230 | 264–329 | 438–483 |
| h-Hiap1 | 29–96 | 169–235 | 255–322 | 546–591 |
| m-Hiap1 | 29–96 | 169–235 | 255–322 | 544–589 |
| h-Hiap2 | 46–113 | 184–250 | 269–336 | 560–605 |
| m-Hiap2 | 25–92 | 156–222 | 241–308 | 541–578 |

*Positions indicate correspond to those shown in FIGS. 1–4.

Recognition of this mammalian IAP family has provided emergent patterns of protein structure. Recognition of these patterns has also allowed us assign the function of a modulator of apoptosis to a drosophila gene product of previously unknown function (Genbank Accession Number M96581). The amino acid sequence of this protein, termed diap, is shown in FIG. 8 for comparison.

The IAP proteins may be used to inhibit the apoptosis which occurs as part of disease or disorder processes. For example, IAP polypeptides or nucleic acid encoding IAP polypeptides may be administered for the treatment of or prevention of apoptosis which occurs as a part of AIDS, neurodegenerative diseases, ischemic injury, toxin-induced liver disease and myelodysplastic syndromes. Nucleic acid encoding the IAP polypeptide may also be provided to inhibit apoptosis.

II. Cloning of IAP Genes

A. XIAP

Our search for human genes potentially involved in apoptosis has resulted in the identification of an x-linked sequence tag site (STS) in the GenBank which demonstrated strong homology with the conserved RZF domain of CpIAP and OpIAP, the two baculovirus genes known to inhibit apoptosis (Clem et al., Mol. Cell Biol., 14:5212–5222, (1994); and Birnbaum et al, J. Virol. 68:2521–8, (1994)). Screening a human fetal brain ZapII cDNA library (Stratagene, La Jolla, Calif.) with this STS resulted in the identification and cloning of xiap (for X-linked Inhibitor of apoptosis protein gene). The human gene has a 1.7 kb coding sequence that includes three BIR (baculovirus inhibitor of apoptosis repeat (Crook et al., J. Virol. 67:2168–74, (1993), Clem et al., Science 254:1388–90, (1991); and Birnbaum et al., J. Virol., 68:2521–8, (1994)) domains and a zinc finger. Northern analysis with xiap reveals a greater than 7 kb message expressed in different tissues particularly liver and kidney (FIG. 12). The large size of the transcript reflects large 5' and 3' untranslated regions.

B. HUMAN HIAP1 and HIAP2

The hiap1 and hiap2 genes were cloned by screening a human liver library (Stratagene) with a probe including the whole xiap coding region at low stringency (40° C. wash, 2×ssc, 10% SDS) (FIGS. 2 and 3). hiap1 and hiap2 were also independently detected using a probe derived from a expressed sequence tag (EST) (GenBank Accession No. T96284) which includes a portion of a BIR domain. This EST was originally isolated by the PCR amplification of a cDNA library using the EST-specific primers. The derived probe was then used to screen the human liver cDNA library for full length hiap coding sequences. We have subsequently detected a third DNA which includes the hiap2 sequence which appears to lack one exon, presumably due to alternative mRNA splicing (see boxed region in FIG. 3). FIGS. 8 and 9 show hiap1 and hiap2 expression in human tissues as assayed by Northern Analysis.

C. M-XIAP

Screening of a mouse embryo λgt11 cDNA library (Clonetech, Palo Alto, Calif.) and a mouse FIX II genomic library with a xiap cDNA clones probe has resulted in the identification of 14 positive cDNA and two hybridizing genomic clones. A cDNA contig spanning 8.0 kb was constructed using 12 overlapping mouse clones. DNA sequencing revealed a coding sequence of about 1.7 kb. The mouse gene called m-xiap (for mouse x-linked inhibitor of apoptosis protein gene) shows striking amino acid homology with xiap at and around the initiation methionine, the stop codon, the three BIR domains and the zinc finger domain. As with the human gene, the mouse homologue contains large 5' and 3' UTRs predicted to result in a transcript as large as 7–8 kb.

Sequencing and restriction mapping of m-xiap can be used to further delineate the structure and genomic organization of m-xiap. Southern blot analysis and inverse PCR technique (Groden et al., Cell 66:589–600 (1991) can be employed to map exons and sequence exon-intron boundaries.

Antisera can be raised against a m-xiap fusion protein expressed in *Escherichia coli* using a bacterial expression system. The resulting antisera can be used along with Northern blot analysis to analyze the spatial and temporal expression of m-xiap in the mouse.

D. M-HIAP1 and M-HIAP2

The murine homologs to hiap1 and hiap2 were cloned and sequenced in the same general manner as m-xiap using the human hiap1 and hiap2 sequences as probes. Cloning of m-hiap1 and m-hiap2 provide further demonstrations of the ease with which homologs from different species may be detected and obtained using the techniques provided herein and those generally known to one skilled in the art of molecular biology.

III. Cloning of Additional IAP Genes

Low stringency Southern blot hybridization of human genomic DNA using probes specific for xiap, hiap1 and hiap2 show bands which correspond to the other known human IAP sequences. In addition, these probes detect sequences which do not correspond to known IAP sequences. This result indicates that additional IAP sequences may be readily identified using low stringency hybridization. Examples of murine and human xiap, hiap1, and hiap2 specific primers which may be used to clone additional genes by RT PCR are shown in Table 5. Standard techniques including PCR and hybridization may be used to clone homologs and additional genes.

IV. Characterization of IAP Apoptosis Modulating Activity

The apoptosis inhibiting capability of IAPs can be defined in an in vitro system know to detect alterations in apoptosis. Mammalian expression constructs carrying IAPs and their truncated forms can be introduced into various cell lines such as CHO, HIH 3T3, HL60, Rat-1, or Jurkart cells, for example. In addition, SF21 insect cells may be used in which case the IAP gene is preferentially expressed using an insect heat shock promotor. Apoptosis will then be induced in transfected cells and controls employing standard methodologies (e.g. serum withdrawal and staurosporine). A survival index (ratio of surviving transfected cells to surviving control cells) will indicate the strength of each IAP construct in inhibiting apoptosis. These experiments can confirm the presence of apoptosis inhibiting or enhancing activity and, can help to determine the minimal functional region of an IAP. These methods may also be used in combination with compounds to identify compounds which modulate apoptosis via their effect on IAP expression.

Figure 14A:
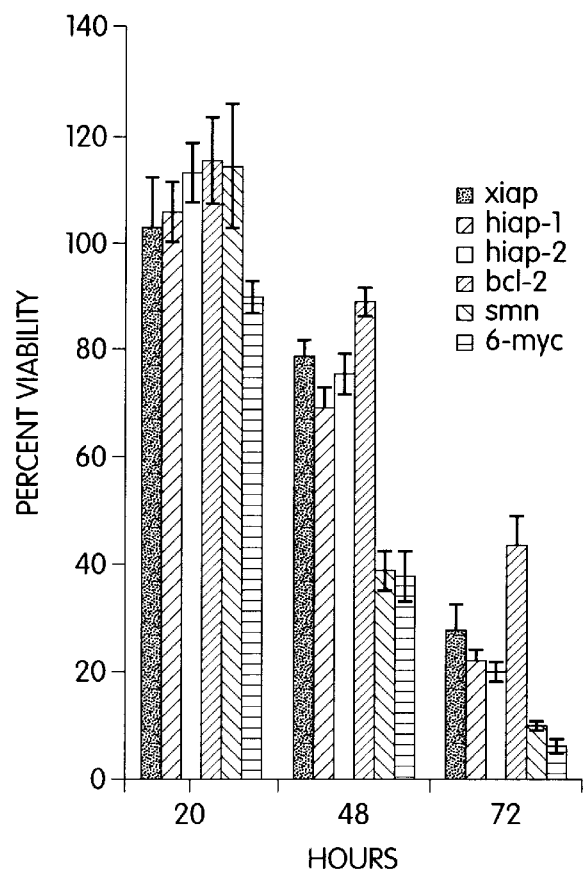
Figure 14B:
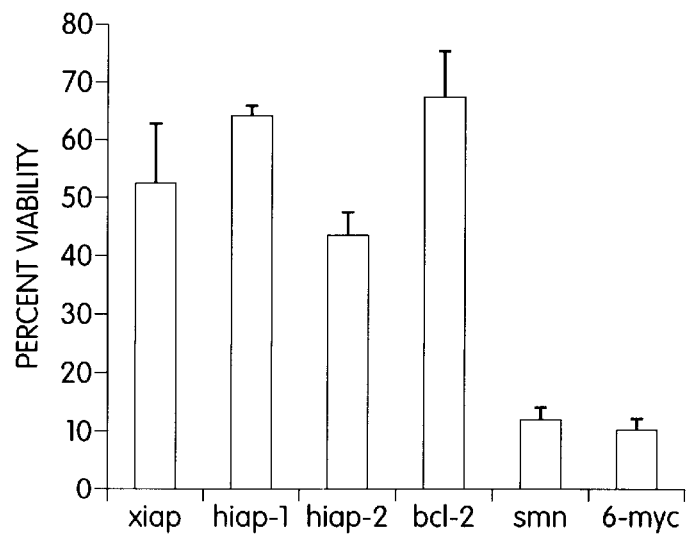
Figure 14C:
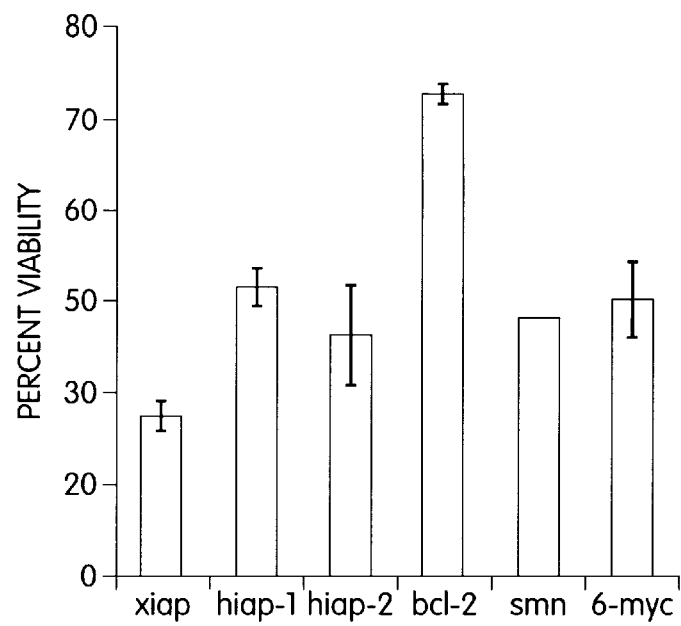
Figure 14D:
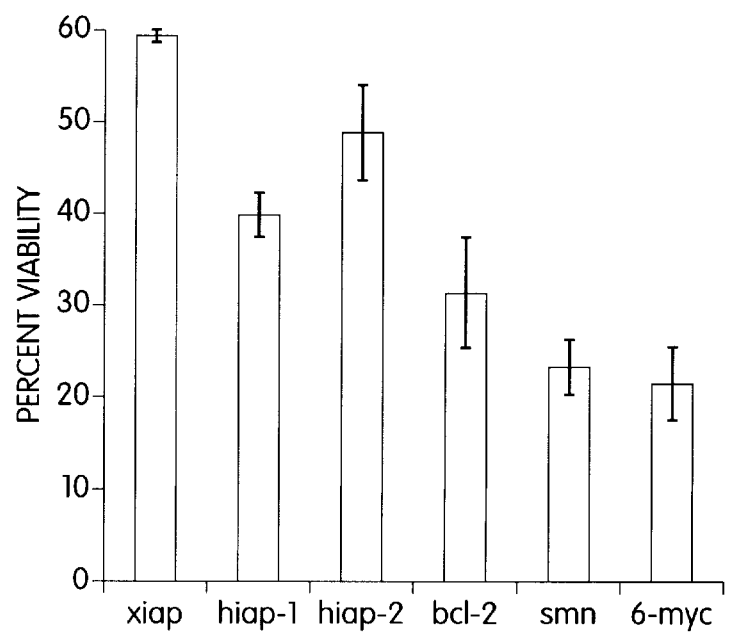

FIGS. 14A–14D show specific examples of apoptosis suppression assays. FIG. 14A shows CHO survival following serum withdrawal. CHO cells were transfected via Lipofectace with 2 µg of each of the following recombinant plasmids; pCDNA3-6myc-hiap-1, pCDNA3-6myc-hiap-2, pCDNA3-6myc-xiap, pCDNA3-6myc, pCDNA3-HA-smn, and pCDNA3-bcl-2. Oligonucleotide primers were synthesized to allow PCR amplification and cloning of the xiap, hiap-1 and hiap-2. Oligonucleotide primers were synthesized to allow PCR amplification and cloning of the xiap, hiap-1, and hiap-2 ORFs in pCDNA3 (Invitrogen). Each construct was modified to incorporate a synthetic myc tag encoding six repeats of the peptide sequence MEQKLISEEDL (SEQ ID NO:43) allowing detection of myc-IAP fusion proteins via monoclonal anti-myc antiserum (Egan, et al., Nature 363:45–51, 1993). Triplicate samples of cell lines in 24 well dishes were washed 5 times with serum free media and maintained in serum free conditions during the course of the experiment. Trypan blue exclusion counting of viable cells utilizing a hemocytometer was performed on samples at time zero, 24 hrs., 48 hrs., and 72 hrs., post serum withdrawal. Survival was calculated as a percentage of initial numbers. Numbers represent the average of three separate experiments performed in triplicate, +/− average deviation. FIG. 14B shows survival of CHO transfected cell lines following exposure to menadione. Cell lines were plated in 24 well dishes, allowed to grow overnight, then exposed for 1.5 hrs. to [20 mM] menadione (Sigma). Triplicate samples were harvested at the time of exposure and at 24 hrs. post exposure and assessed by trypan blue exclusion for survival. Data represents the average of three independent experiments, +/− average deviation. FIG. 14C shows survival of Rat-1 cells following staurosporine exposure. Rat-1 cells were transfected with the plasmids listed in a), with selection in [800 mg/ml] G418 media for two weeks. Cell lines were assessed for resistance to [1 µM]staurosporine induced apoptosis for 5 hrs. Viable cell counts were obtained 24 hrs. post exposure via trypan blue exclusion counting of samples prepared in triplicate. Numbers represent the average of two independent experiments, +/− average deviation. FIG. 14D shows Rat-1 cell lines were tested for resistance to [10 mM] menadione for 1.5 hrs., then counted at 18 hrs. post exposure. Numbers represent the average of three experiments performed in triplicate, +/− average deviation.

Specific examples of apoptosis assays are also provided in the following references:

Lymphocyte: C. J. Li et al., "Induction of apoptosis in uninfected lymphocytes by HIV-1 Tat protein", Science, 268:429–431 (1995); D. Gibellini et al., "Tat-expressing Jurkat cells show an increased resistance to different apoptotic stimuli, including acute human immunodeficiency virus-type 1 (HIV-1) infection", Br. J. Haematol. 89:24–33, (1995); S. J. Martin et al., "HIV-1 infection of human CD4+ T cells in vitro. Differential induction of apoptosis in these cells." J. Immunol. 152:330–42, (1994); C. Terai et al., "Apoptosis as a mechanism of cell death in cultured T lymphoblasts acutely infected with HIV-1", J. Clin Invest., 87:1710–5, (1991); J. Dhein et al., "Autocrine T-cell suicide mediated by APO-1/(Fas/CD95)", Nature 373:438–441, (1995); P. D. Katsikis et al., "Fas antigen stimulation induces marked apoptosis of T lymphocytes in human immunodeficiency virus-infected individuals", J. Exp. Med. 1815:2029–2036, (1995); Michael O. Westendorp et al., Sensitization of T cells to CD95-mediated apoptosis by HIV-1 Tat and gp120", Nature, 375:497, (1995); DeRossi et al., Virology 198:234–44, (1994).

Fibroblasts: H. Vossbeck et al., "Direct transforming activity of TGF-beta on rat fibroblasts", Int. J. Cancer, 61:92–97, (1995); S. Goruppi et al., "Dissection of c-myc domains involved in S phase induction of NIH3T3 fibroblasts", Oncogene, 9:1537–44, (1994); A. Fernandez et al., "Differential sensitivity of normal and Ha-ras-transformed C3H mouse embryo fibroblasts to tumor necrosis factor: induction of bcl-2, c-myc, and manganese superoxide dismutase in resistant cells", Oncogene, 9:2009–17, (1994); E. A. Harrington et al., "c-Myc-induced apoptosis in fibroblasts in inhibited by specific cytokines", EMBO J., 13:3286–3295, (1994); N. Itoh et al., "A novel protein domain required for apoptosis. Mutational analysis of human Fas antigen", J. Biol. Chem., 268:10932–7, (1993).

Neuronal Cells: G. Melino et al., "Tissue transglutaminase and apoptosis: sense and antisense transfection studies with human neuroblastoma cells", Mol. Cell. Biol., 14:6584–6596, (1994); D. M. Rosenbaum et al., "Evidence for hypoxia-induced, programmed cell death of cultured neurons", Ann. Neurol., 36:864–870, (1994); N. Sato et al., "Neuronal differentiation of PC12 cells as a result of prevention of cell death by bcl-2", J. Neurobiol. 25:1227–1234, (1994); G. Ferrari et al., "N-acetylcysteine (D- and L-stereoisomers) prevents apoptotic death of neuronal cells", J. Neurosci., 1516:2857–2866, (1995); A. K. Talley et al., "Tumor necrosis factor alpha-induced apoptosis in human neuronal cells: protection by the antioxidant N-acetylcysteine and the genes bcl-2 and crmA", Mol. Cell Biol., 1585:2359–2366, (1995); A. K. Talley et al., "Tumor Necrosis Factor Alpha-Induced Apoptosis in Human Neuronal Cells: Protection by the Antioxidant N-Acetylcysteine and the Genes bcl-2 and crmA", Mol. and Cell. Biol., 15:2359–2366, (1995); G. Walkinshaw et al., "Induction of apoptosis in catecholaminergic PC12 cells by L-DOPA. Implications for the treatment of Parkinson's disease.", J. Clin. Invest. 95:2458–2464, (1995).

Insect Cells: R. J. Clem et al., "Prevention of apoptosis by a baculovirus gene during infection of insect cells", Science, 254:1388–90, (1991); N. E. Crook et al., "An apoptosis-inhibiting baculovirus gene with a zinc finger-like motif", J. Virol., 67:2168–74, (1993); S. Rabizadeh et al., "Expression of the baculovirus p35 gene inhibits mammalian neural cell death", J. Neurochem., 61:2318–21, (1993); M. J. Birnbaum et al., "An apoptosis-inhibiting gene from a nuclear polyhidrosis virus encoding a polypeptide with Cys/His sequence motifs", J. Virol. 68:2521–8, (1994); R. J. Clem et al., "Control of programmed cell death by the baculovirus genes p35 and iap", Mol. Cell. Biol., 14:5212–5222, (1994).

V. Construction of a Transgenic Animal

Characterization of IAPs can provide information that allows for the development of an IAP knockout animal model, preferably mammal, most preferably a mouse, by homologous recombination. Similarily, an IAP overproducing animal may be produced by means of DNA sequence integration into the genome.

A replacement type targeting vector to create a knockout can be constructed using an isogenic genomic clone from a mouse strain, e.g. 129/Sv (Strategene LaJolla, Calif.). The targeting vector will be introduced into a J1 line of embryonic stem (ES) cells by electroporation to generate ES cell lines that carry a profoundly truncated form of an IAP. To generate chimeric founder mice, the targeted cell lines will be injected into a mouse blastula stage embryo. Heterozygote offspring will be interbred to homozygosity. Knockout mice may be constructed as a means of screening in vivo for therapeutic compounds which modulate apoptosis.

Animals having enhanced IAP expression may also be constructed using standard transgenic technologies.

VI. IAP Protein Expression

IAP genes may be expressed in both prokaryotic and eukaryotic cell types. For those IAP's which increase apoptosis it may be desirable to express the protein under control of an inducible promotor for the purposes of protein production.

In general, IAP proteins according to the invention may be produced by transformation of a suitable host cell with all or part of a IAP-encoding cDNA fragment (e.g., the cDNA described above) in a suitable expression vehicle.

Those skilled in the field of molecular biology will understand that any of a wide variety of expression systems may be used to provide the recombinant protein. The precise host cell used is not critical to the invention. The IAP protein may be produced in a prokaryotic host (e.g., *E. coli*) or in a eukaryotic host (e.g., *Saccharomyces cerevisiae*, insect cells, e.g., Sf21 cells, or mammalian cells, e.g., COS 1, NIH 3T3, or HeLa cells). Such cells are available from a wide range of sources (e.g., the American Type Culture Collection, Rockland, Md.; also, see, e.g., Ausubel et al., *Current Protocols in Molecular Biology*, John Wiley & Sons, New York, 1994). The method of transformation or transfection and the choice of expression vehicle will depend on the host system selected. Transformation and transfection methods are described, e.g., in Ausubel et al., (supra); expression vehicles may be chosen from those provided, e.g., in *Cloning Vectors: A Laboratory Manual* (P. H. Pouwels et al., 1985, Supp. 1987).

One preferred expression system is the baculovirus system (using, for example, the vector pBacPAK9) available from Clontech (Palo Alto, Calif.). If desired, this system may be used in conjunction with other protein expression techniques, for example, the myc tag approach described by Evan et al. (Mol. Cell Biol. 5:3610–3616, 1985).

Alternatively, a IAP protein is produced by a stably-transfected mammalian cell line. A number of vectors suitable for stable transfection of mammalian cells are available to the public, e.g., see Pouwels et al. (supra); methods for constructing such cell lines are also publicly available, e.g., in Ausubel et al. (supra). In one example, cDNA encoding the IAP protein is cloned into an expression vector which includes the dihydrofolate reductase (DHFR) gene. Integration of the plasmid and, therefore, the IAP protein-encoding gene into the host cell chromosome is selected for by inclusion of 0.01–300 μM methotrexate in the cell culture medium (as described in Ausubel et al., supra). This dominant selection can be accomplished in most cell types. Recombinant protein expression can be increased by DHFR-mediated amplification of the transfected gene. Methods for selecting cell lines bearing gene amplifications are described in Ausubel et al. (supra); such methods generally involve extended culture in medium containing gradually increasing levels of methotrexate. DHFR-containing expression vectors commonly used for this purpose include pCVSEII-DHFR and pAdD26SV(A) (described in Ausubel et al., supra). Any of the host cells described above or, preferably, a DHFR-deficient CHO cell line (e.g., CHO DHFR⁻ cells, ATCC Accession No. CRL 9096) are among the host cells preferred for DHFR selection of a stably-transfected cell line or DHFR-mediated gene amplification.

Once the recombinant IAP protein is expressed, it is isolated, e.g., using affinity chromatography. In one example, an anti-IAP protein antibody (e.g., produced as described herein) may be attached to a column and used to isolate the IAP protein. Lysis and fractionation of IAP protein-harboring cells prior to affinity chromatography may be performed by standard methods (see, e.g., Ausubel et al., supra).

Once isolated, the recombinant protein can, if desired, be further purified, e.g., by high performance liquid chromatography (see, e.g., Fisher, *Laboratory Techniques In Biochemistry And Molecular Biology*, eds., Work and Burdon, Elsevier, 1980).

Polypeptides of the invention, particularly short IAP protein fragments, can also be produced by chemical synthesis (e.g., by the methods described in *Solid Phase Peptide Synthesis*, 2nd ed., 1984 The Pierce Chemical Co., Rockford, Ill.).

These general techniques of polypeptide expression and purification can also be used to produce and isolate useful IAP fragments or analogs (described herein).

VI. Anti-IAP Antibodies

To generate IAP-specific antibodies, a IAP coding sequence (i.e., amino acids 180–276) can be expressed as a C-terminal fusion with glutathione S-transferase (GST) (Smith et al., Gene 67:31–40, 1988). The fusion protein can be purified on glutathione-Sepharose beads, eluted with glutathione cleaved with thrombin (at the engineered cleavage site), and purified to the degree necessary for immunization of rabbits. Primary immunizations can be carried out with Freund's complete adjuvant and subsequent immunizations with Freund's incomplete adjuvant. Antibody titres are monitored by Western blot and immunoprecipitation analyses using the thrombin-cleaved IAP protein fragment of the GST-IAP fusion protein. Immune sera are affinity purified using CNBr-Sepharose-coupled IAP protein. Antiserum specificity is determined using a panel of unrelated GST proteins (including GSTp53, Rb, HPV-16 E6, and E6-AP) and GST-trypsin (which was generated by PCR using known sequences).

As an alternate or adjunct immunogen to GST fusion proteins, peptides corresponding to relatively unique hydrophilic regions of IAP may be generated and coupled to keyhole limpet hemocyanin (KLH) through an introduced C-terminal lysine. Antiserum to each of these peptides is similarly affinity purified on peptides conjugated to BSA, and specificity tested in ELISA and Western blots using peptide conjugates, and by Western blot and immunoprecipitation using IAP expressed as a GST fusion protein.

Alternatively, monoclonal antibodies may be prepared using the IAP proteins described above and standard hybridoma technology (see, e.g., Kohler et al., Nature 256:495, 1975; Kohler et al., Eur. J. Immunol. 6:511, 1976; Kohler et al., Eur. J. Immunol. 6:292, 1976; Hammerling et al., In Monoclonal Antibodies and T Cell Hybridomas, Elsevier, N.Y., 1981; Ausubel et al., supra). Once produced, monoclonal antibodies are also tested for specific IAP recognition by Western blot or immunoprecipitation analysis (by the methods described in Ausubel et al., supra). Antibodies which specifically recognize IAP are considered to be useful in the invention; such antibodies may be used, e.g., in an immunoassay to monitor the level of IAP produced by a mammal (for example, to determine the amount or subcellular location of IAP).

Preferably, antibodies of the invention are produced using fragments of the IAP protein which lie outside highly conserved regions and appear likely to be antigenic, by criteria such as those provided by the Peptidestructure program of the Genetics Computer Group Sequence Analysis Package (Program Manual for the GCG Package, Version 7, 1991) using the algorithm of Jameson and Wolf (CABIOS 4:181 1988)). Specifically these regions, which are found between BIR1 and BIR2 of all the IAP proteins, are in hiap1 from amino acid 99 to 170, hiap2 from amino acid 123 to 184, xiap from 116 to 133 and m-xiap from 116 to 133. In one specific example, such fragments are generated by standard techniques of PCR and cloned into the pGEX expression vector (Ausubel et al., supra). Fusion proteins are expressed in *E. coli* and purified using a glutathione agarose affinity matrix as described in Ausubel et al. (supra). To attempt to minimize the potential problems of low affinity or specificity of antisera, two or three such fusions are generated for each protein, and each fusion is injected into at least two rabbits. Antisera are raised by injections in a series, preferably including at least three booster injections.

VII. Identification of Molecules that Modulate IAP Protein Expression

Isolation of the IAP cDNAs also facilitates the identification of molecules which increase or decrease IAP expression. According to one approach, candidate molecules are added at varying concentrations to the culture medium of cells expressing IAP mRNA. IAP expression is then measured, for example, by standard Northern blot analysis (Ausubel et al., supra) using a IAP cDNA (or cDNA fragment) as a hybridization probe (see also Table 5). The level of IAP expression in the presence of the candidate molecule is compared to the level measured for the same cells in the same culture medium but in the absence of the candidate molecule.

If desired, the effect of candidate modulators on expression may, in the alternative, be measured at the level of IAP protein production using the same general approach and standard immunological detection techniques, such as Western blotting or immunoprecipitation with a IAP-specific antibody (for example, the IAP antibody described herein).

Candidate modulators may be purified (or substantially purified) molecules or may be one component of a mixture of compounds (e.g., an extract or supernatant obtained from cells; Ausubel et al., supra). In a mixed compound assay, IAP expression is tested against progressively smaller subsets of the candidate compound pool (e.g., produced by standard purification techniques, e.g., HPLC or FPLC) until a single compound or minimal compound mixture is demonstrated to modulate IAP expression.

Alternatively, or in addition, candidate compounds may be screened for those which modulate IAP apoptosis inhibiting activity. In this approach, the degree of apoptosis in the presence of a candidate compound is compared to the degree of apoptosis in its absence, under equivalent conditions. Again, such a screen may begin with a pool of candidate compounds, from which one or more useful modulator compounds are isolated in a step-wise fashion. Apoptosis activity may be measured by any standard assay, for example, those described herein.

Another method for detecting compounds which modulate IAP polypeptide activity is to screen for compounds which physically interact with a given IAP polypeptide. Such compounds may be detected using adaptations of the interaction trap expression systems known in the art. Such systems detect protein interactions using a transcriptional activation assay and are generally described in Gyuris et al., Cell 75:791–803 (1993), and Field and Song, Nature 340:245–246, (1989), and are commercially available from Clonetech (Palo Alto, Calif.). In addition, PCT Publication WO 95/28497 (hereby incorporated by reference) describe a method for detecting proteins involved in apoptosis by virtue of their interaction with Bcl-2 using such an interaction trap assay. A similar method may be exploited to identify proteins and other compounds which interact with the IAP polypeptides.

Candidate IAP modulators include peptide as well as non-peptide molecules (e.g., peptide or non-peptide molecules found, e.g., in a cell extract, mammalian serum, or growth medium on which mammalian cells have been cultured).

A molecule which promotes an increase in IAP expression or IAP activity is considered particularly useful in the invention; such a molecule may be used, for example, as a therapeutic to increase cellular levels of IAP and thereby exploit the effect of IAP polypeptides for the inhibition of apoptosis.

A molecule which decreases IAP activity (e.g., by decreasing gene expression or polypeptide activity) may be useful for decreasing cell proliferation. Such uses include treatment of neoplasms (see Table 3, below) or other cell proliferative diseases.

Modulators found to be effective at the level of IAP expression or activity may be confirmed as useful in animal models and, if successful, may be used as anti-cancer therapeutics for either the inhibition or the enhancement of apoptosis, as appropriate.

IX. IAP Therapy

Because expression levels of IAP genes correlates with the levels of apoptosis, the IAP gene also finds use in anti-apoptosis gene therapy. In particular, to sustain neuronal cells, lymphocytes (T-cells and B-cells), or cells exposed to ischemic injury, a functional IAP gene may be introduced into cells at the sites predicted to undergo undesirable apoptosis.

Retroviral vectors, adenoviral vectors, adeno-associated viral vectors, or other viral vectors with the appropriate tropism for cells likely to be involved in apoptosis (for example, epithelial cells) may be used as a gene transfer delivery system for a therapeutic IAP gene construct. Numerous vectors useful for this purpose are generally known (Miller, Human Gene Therapy 15–14, 1990; Friedman, Science 244:1275–1281, 1989; Eglitis and Anderson, BioTechniques 6:608–614, 1988; Tolstoshev and Anderson, Current Opinion in Biotechnology 1:55–61, 1990; Sharp, The Lancet 337:1277–1278, 1991; Cornetta et al., Nucleic Acid Research and Molecular Biology 36:311–322, 1987; Anderson, Science 226:401–409, 1984; Moen, Blood Cells 17:407–416, 1991; and Miller and Rosman, Biotechniques 7:980–990, 1989; Le Gal La Salle et al., Science 259:988–990, 1993; and Johnson, Chest 107:77S–83S, 1995). Retroviral vectors are particularly well developed and have been used in clinical settings (Rosenberg et al., N. Engl. J. Med. 323:370, 1990; Anderson et al., U.S. Pat. No. 5,399,346).

Non-viral approaches may also be employed for the introduction of therapeutic DNA into cells otherwise predicted to undergo apoptosis. For example, IAP may be introduced into a neuronal cell or a T-cell by the techniques of lipofection (Felgner et al., Proc. Natl. Acad. Sci. USA 84:7413, 1987; Ono et al., Neuroscience Lett 117:259, 1990; Brigham et al., Am. J. Med. Sci. 298:278, 1989; Staubinger and Papahadjopoulos, Meth. Enz. 101:512, 1983); asialorosonucoid-polylysine conjugation (Wu and Wu, J. Biol. Chem. 263:14621, 1988; Wu et al., J. Biol. Chem. 264:16985, 1989); or, less preferably, microinjection under surgical conditions (Wolff et al., Science 247:1465, 1990).

For any of the above approaches, the therapeutic IAP DNA construct is preferably applied to the site of the predicted apoptosis event (for example, by injection), but may also be applied to tissue in the vicinity of the predicted apoptosis event or even to a blood vessel supplying the cells predicted to undergo apoptosis.

In the gene therapy constructs, IAP cDNA expression is directed from any suitable promoter (e.g., the human cytomegalovirus, simian virus 40, or metallothionein promoters), and its production is regulated by any desired mammalian regulatory element. For example, if desired, enhancers known to direct preferential gene expression in neural cells or T-cells may be used to direct IAP expression. Such enhancers include, without limitation, those enhancers which are characterized as tissue or cell specific in their expression.

Alternatively, if a IAP genomic clone is utilized as a therapeutic construct (for example, following its isolation by hybridization with the IAP cDNA described above), IAP expression is regulated by its cognate regulatory sequences or, if desired, by regulatory sequences derived from a heterologous source, e.g., any of the promoters or regulatory elements described above.

Less preferably, IAP gene therapy is accomplished by direct administration of the IAP mRNA to a cell predicted to undergo apoptosis. This mRNA may be produced and isolated by any standard technique, but is most readily produced by in vitro transcription using a IAP cDNA under the control of a high efficiency promoter (e.g., the T7 promoter). Administration of IAP mRNA to malignant cells is carried out by any of the methods for direct nucleic acid administration described above.

Ideally, the production of IAP protein by any gene therapy approach described above results in a cellular level of IAP that is at least equivalent to the normal, cellular level of IAP in an unaffected individual. Treatment by any IAP-mediated gene therapy approach may be combined with more traditional therapies.

Another therapeutic approach included within the invention involves direct administration of recombinant IAP protein, either to the site of a predicted apoptosis event (for example, by injection) or systemically by any conventional recombinant protein administration technique. The actual dosage of IAP depends on a number of factors, including the size and health of the individual patient, but, generally, between 0.1 mg and 100 mg inclusive are administered per day to an adult in any pharmaceutically-acceptable formulation.

X. Administration of IAP Polypeptides, IAP Genes, or Modulators of IAP Synthesis or Function A IAP protein, gene, or modulator may be administered with a pharmaceutically-acceptable diluent, carrier, or excipient, in unit dosage form. Conventional pharmaceutical practice may be employed to provide suitable formulations or compositions to administer IAP to patients suffering from or presymptomatic for a IAP-associated carcinoma. Any appropriate route of administration may be employed, for example, parenteral, intravenous, subcutaneous, intramuscular, intracranial, intraorbital, ophthalmic, intraventricular, intracapsular, intraspinal, intracisternal, intraperitoneal, intranasal, aerosol, or oral administration. Therapeutic formulations may be in the form of liquid solutions or suspensions; for oral administration, formulations may be in the form of tablets or capsules; and for intranasal formulations, in the form of powders, nasal drops, or aerosols.

Methods well known in the art for making formulations are found in, for example, "Remington's Pharmaceutical Sciences." Formulations for parenteral administration may, for example, contain excipients, sterile water, or saline, polyalkylene glycols such as polyethylene glycol, oils of vegetable origin, or hydrogenated napthalenes. Biocompatible, biodegradable lactide polymer, lactide/glycolide copolymer, or polyoxyethylene-polyoxypropylene copolymers may be used to control the release of the compounds. Other potentially useful parenteral delivery systems for IAP modulatory compounds include ethylene-vinyl acetate copolymer particles, osmotic pumps, implantable infusion systems, and liposomes. Formulations for inhalation may contain excipients, for example, lactose, or may be aqueous solutions containing, for example, polyoxyethylene-9-lauryl ether, glycocholate and deoxycholate, or may be oily solutions for administration in the form of nasal drops, or as a gel.

If desired, treatment with a IAP protein, gene, or modulatory compound may be combined with more traditional therapies for the disease such as surgery, radiation, or chemotherapy for cancers; surgery, steroid therapy, and chemotherapy for autoimmune diseases; antiviral therapies for AIDS; and for example, TPA for ischemic injury.

XI. Detection of a Condition Involving Altered Apoptosis

IAP polypeptides and nucleic acid sequences find diagnostic use in the detection or monitoring of conditions involving aberrant levels of apoptosis. For example, decrease expression of IAP may be correlated with enhanced apoptosis in humans (see XII, below). Accordingly, a decrease or increase in the level of IAP production may provide an indication of a deleterious condition. Levels of IAP expression may be assayed by any standard technique. For example, its expression in a biological sample (e.g., a biopsy) may be monitored by standard Northern blot analysis or may be aided by PCR (see, e.g., Ausubel et al., supra; PCR Technology: Principles and Applications for DNA Amplification, ed., H. A. Ehrlich, Stockton Press, N.Y.; and Yap and McGee, Nucl. Acids. Res. 19:4294, 1991).

Alternatively, a patient sample may be analyzed for one or more mutations in the IAP sequences using a mismatch detection approach. Generally, these techniques involve PCR amplification of nucleic acid from the patient sample, followed by identification of the mutation (i.e., mismatch) by either altered hybridization, aberrant electrophoretic gel migration, binding or cleavage mediated by mismatch binding proteins, or direct nucleic acid sequencing. Any of these techniques may be used to facilitate mutant IAP detection, and each is well known in the art; examples of particular techniques are described, without limitation, in Orita et al., Proc. Natl. Acad. Sci. USA 86:2766–2770, (1989); and Sheffield et al., Proc. Natl. Acad. Sci. USA 86:232–236, (1989).

In yet another approach, immunoassays are used to detect or monitor IAP protein in a biological sample. IAP-specific polyclonal or monoclonal antibodies (produced as described above) may be used in any standard immunoassay format (e.g., ELISA, Western blot, or RIA assay) to measure IAP polypeptide levels; again comparison is to wild-type IAP levels, and a decrease in IAP production is indicative of a condition involving increased apoptosis. Examples of immunoassays are described, e.g., in Ausubel et al., supra. Immunohistochemical techniques may also be utilized for IAP detection. For example, a tissue sample may be obtained from a patient, and a section stained for the presence of IAP using an anti-IAP antibody and any standard detection system (e.g., one which includes a secondary antibody conjugated to horseradish peroxidase). General guidance regarding such techniques can be found in, e.g., Bancroft and Stevens (*Theory and Practice of Histological Techniques*, Churchill Livingstone, 1982) and Ausubel et al. (supra).

In one preferred example, a combined diagnostic method may be employed that begins with an evaluation of IAP protein production (for example, by immunological techniques or the protein truncation test (Hogerrorst, F. B. L., et al., Nature Genetics 10:208–212 (1995) and also includes a nucleic acid-based detection technique designed to identify more subtle IAP mutations (for example, point mutations). As described above, a number of mismatch detection assays are available to those skilled in the art, and any preferred technique may be used (see above). By this approach, mutations in IAP may be detected that either result in loss of IAP expression or loss of IAP biological activity. In a variation of this combined diagnostic method, IAP biological activity is measured as protease activity using any appropriate protease assay system (for example, those described above).

Mismatch detection assays also provide the opportunity to diagnose a IAP-mediated predisposition to diseases of apoptosis. For example, a patient heterozygous for an IAP mutation may show no clinical symptoms and yet possess a higher than normal probability of developing one or more types of neurodegenerative, myelodysplastic or ischemic diseases. Given this diagnosis, a patient may take precautions to minimize their exposure to adverse environmental factors (for example, UV exposure or chemical mutagens) and to carefully monitor their medical condition (for example, through frequent physical examinations). This type of IAP diagnostic approach may also be used to detect IAP mutations in prenatal screens.

The IAP diagnostic assays described above may be carried out using any biological sample (for example, any biopsy sample or bodily fluid or tissue) in which IAP is normally expressed (for example, the inhibition of apoptosis). Identification of a mutant IAP gene may also be assayed using these sources for test samples. Alternatively, a IAP mutation, particularly as part of a diagnosis for predisposition to IAP-associated degenerative disease, may be tested using a DNA sample from any cell, for example, by mismatch detection techniques; preferably, the DNA sample is subjected to PCR amplification prior to analysis.

To demonstrate the utility of IAP gene sequences as diagnostics and prognostics for cancer we probed the Clonetech (La Jolla) Human Cancer Cell Line Multiple Tissue Northern Blot (#7757-1). As Table 3 shows, all cancer lines tested showed increased IAP expression relative to samples from non-cancerous control cell lines. xiap expression was particularly high in HeLa (S-3), chronic myelogenous leukemia (K-562), colorectal adenocarcinoma (SW-480) and melanoma (G-361) lines. hiap1 expression was extremely high in Burkitt's lymphoma and was also elevated in colorectal adenocarcinoma. hiap2 expression was particularly high in chronic myelogenous leukemia (K-562) and colorectal adenocarcinoma (SW-480).

In addition, we note that we have mapped hiap1 and hiap2 to human chromosome 11g23. This is a known hotspot for cancer causing mutations.

TABLE 3

Northern Blot IAP RNA levels in Cancer Cells*

|  | xiap | hiap1 | hiap2 |
| --- | --- | --- | --- |
| Promylocytic Leukemia HL-60 | + | + | + |
| Hela S-3 | + | + | + |
| Chronic Myclogenous Leukemia K-562 | +++ | + | +++ |
| Lymphoblastic Leukemia MDLT-4 | +++ | + | + |
| Burkitt's Lymphoma Raji | + | +(×10) | + |
| Colorectal Adenocarcinoma SW-480 | +++ | +++ | +++ |
| Lung Carcinoma A-549 | + | + | + |
| Melanoma G-361 | +++ | + | + |

*Levels are indicated by a (+) and are the approximate increase in RNA levels relative to Northern blots of RNA from non-cancerous control cell lines. A single plus indicates an estimated increase of at least 1-fold

XII. Treatment of HIV Infected Individuals

We have found that hiap1 and hiap 2 expression is decreased significantly in HIV infected human cells. This decrease precedes apoptosis. The result indicates that administration of HIAP1, HIAP2, genes encoding these proteins, or compounds which upregulate these genes can be used to prevent T-cell attrition in HIV infected patients. The following assay may also be used to screen for compounds which alter hiap1 and hiap2 expression and which also prevent apoptosis.

The experiments were preformed as follows: Cultured mature lymphocyte CD-4+ T-cell lines (H9 labelled "a"; CEM/CM-3 labelled "b"; 6T-CEM labelled "c"; and Jurkat labelled "d" in FIGS. 13A and 13B) were examined for apoptosis (FIG. 13A) and hiap gene expression (FIG. 13B). Control conditions are labelled as lane 1 in FIG. 13A and FIG. 13B. Lane 2 shows the result 24 hours after PHA/PMH (phytohemagglutinin, phorbol ester) mitogen stimulation. Lane 3 shows the result 24 hours after HIV strain $III_B$ infection. The "M" refers to standard DNA markers, the 123 bp ladder (Gibco-BRL) in FIG. 13B, and lambda HindIII ladder (Gibco-BRL) in FIG. A.

In FIG. 13A is a picture of ethidium bromide stained gel showing the presence of DNA ladders (as assayed by the test of Prigent et al., J. of Immun. Methods, 160:139–140, (1993), indicative of apoptosis. The sensitivity and degree of apoptosis of the four T-cell lines varies following mitogen stimulation and HIV infection.

For the experiment examining hiap gene expression, total RNA was prepared from the cultured cells and subject to a reverse transcriptase reaction using oligo-dT priming. The RT cDNA products were PCR amplified using specific primers (as shown in Table 5) for the detection of hiap2a, hiap2b and hiap 1. PCR conditions were routine (94° C. melting for 1 minute, 55° C. annealing for 2 minutes and 72° C. extension for 1.5 minutes for 35 cycles) using a Perkin-Elmer 480 thermocycler. The FIG. 13B shows a picture of the RT-PCR products run on a 1% agarose gel stained with ethidium bromide. Absence of hiap2 transcripts is noted in all four cell lines 24 hours after HIV infection. In three of four cell lines (all except H9), the hiap1 gene is also dramatically down-regulated after HIV infection. PHA/PMA mitogen stimulation also appears to decrease hiap gene expression, particularly for hiap2 and to a lesser extent, for hiap1.

The data from these experiments is summarized in the accompanying Table 5. The β-action gene expression was consistent in all cell lines tested, indicating that a flow in the RT-PCR assay does not account for the decreases in hiap gene expression.

TABLE 4

Oligonucleotide primers for the specific RT-PCR amplification of unique IAP genes.

| IAP Gene | Forward Primer (nucleotide position*) | Reverse Primer (nucleotide position*) | Size of Product (bp) |
| --- | --- | --- | --- |
| h-xiap | p2415 (876–896) | p2449 (1291–1311) | 435 |
| m-xiap | p2566 (458–478) | p2490 (994–1013) | 555 |
| h-hiap1 | p2465 (827–847) | p2464 (1008–1038) | 211 |
| m-hiap1 | p2687 (747–767) | p2684 (1177–1197) | 450 |
| hiap2 | p2595 (1562–1585) | p2578 (2339–2363) | 801[a] 618[b] |
| m-hiap2 | p2693 (1751–1772) | p2734 (2078–2100) | 349 |

*Nucleotide position as determined from FIGS. 1–4 for each IAP gene
[a] PCR product size of hiap2a
[b] PCR product size of hiap2b

TABLE 5

Apoptosis and hiap gene expression in cultured T-cells following mitogen stimulation or HIV infection.

| Cell Line | Condition | Apoptosis | hiap1 | hiap2 |
| --- | --- | --- | --- | --- |
| H9 | not stimulated | − | + | +/− |
|  | PHA/PMA stimulated | +++ | + | +/− |
|  | HIV infected | ++ | + | − |
| CEM/CM-3 | not stimulated | − | + | +/− |
|  | PHA/PMA stimulated | +/− | + | − |
|  | HIV infected | +/− | − | − |
| 6T-CEM | not stimulated | − | + | + |
|  | PHA/PMA stimulated | +/− | − | − |
|  | HIV infected | + | − | − |
| Jurkat | not stimulated | − | + | ++ |
|  | PHA/PMA stimulated | + | + | + |
|  | HIV infected | +/− | − | − |

XIII. Preventive Anti-apoptotic Therapy

In a patient diagnosed to be heterozygous for an IAP mutation or to be susceptible to IAP mutations (even if those mutations do not yet result in alteration or loss of IAP biological activity), or a patent diagnosed as HIV positive, any of the above therapies may be administered before the occurrence of the disease phenotype. For example, the therapies may be provided to a patient who is HIV positive but does not yet show a diminished T-cell count or other signs of full-blown AIDS. In particular, compounds shown to increase IAP expression or IAP biological activity may be administered by any standard dosage and route of administration (see above). Alternatively, gene therapy using an IAP expression construct may be undertaken to reverse or prevent the cell defect prior to the development of the degenerative disease.

The methods of the instant invention may be used to reduce or diagnose the disorders described herein in any mammal, for example, humans, domestic pets, or livestock. Where a non-human mammal is treated or diagnosed, the IAP polypeptide, nucleic acid, or antibody employed is preferably specific for that species.

OTHER EMBODIMENTS

In other embodiments, the invention includes any protein which is substantially identical to a mammalian IAP polypeptides (FIGS. 1–6; SEQ ID NO:1–42); such homologs include other substantially pure naturally-occurring mammalian IAP proteins as well as allelic variants; natural mutants; induced mutants; DNA sequences which encode proteins and also hybridize to the IAP DNA sequences of FIGS. 1–6 (SEQ ID NOS:1–42) under high stringency conditions or, less preferably, under low stringency conditions (e.g., washing at 2× SSC at 40° C. with a probe length of at least 40 nucleotides); and proteins specifically bound by antisera directed to a IAP polypeptide. The term also includes chimeric polypeptides that include a IAP portion.

The invention further includes analogs of any naturally-occurring IAP polypeptide. Analogs can differ from the naturally-occurring IAP protein by amino acid sequence differences, by post-translational modifications, or by both. Analogs of the invention will generally exhibit at least 85%, more preferably 90%, and most preferably 95% or even 99% identity with all or part of a naturally-occurring IAP amino acid sequence. The length of sequence comparison is at least 15 amino acid residues, preferably at least 25 amino acid residues, and more preferably more than 35 amino acid residues. Modifications include in vivo and in vitro chemical derivatization of polypeptides, e.g., acetylation, carboxylation, phosphorylation, or glycosylation; such modifications may occur during polypeptide synthesis or processing or following treatment with isolated modifying enzymes. Analogs can also differ from the naturally-occurring IAP polypeptide by alterations in primary sequence. These include genetic variants, both natural and induced (for example, resulting from random mutagenesis by irradiation or exposure to ethanemethylsulfate or by site-specific mutagenesis as described in Sambrook, Fritsch and Maniatis, *Molecular Cloning: A Laboratory Manual* (2d ed.), CSH Press, 1989, or Ausubel et al., supra). Also included are cyclized peptides, molecules, and analogs which contain residues other than L-amino acids, e.g., D-amino acids or non-naturally occurring or synthetic amino acids, e.g., β or γ amino acids.

In addition to full-length polypeptides, the invention also includes IAP polypeptide fragments. As used herein, the term "fragment," means at least 20 contiguous amino acids, preferably at least 30 contiguous amino acids, more preferably at least 50 contiguous amino acids, and most preferably at least 60 to 80 or more contiguous amino acids. Fragments of IAP polypeptides can be generated by methods known to those skilled in the art or may result from normal protein processing (e.g., removal of amino acids from the nascent polypeptide that are not required for biological activity or removal of amino acids by alternative mRNA splicing or alternative protein processing events).

Preferable fragments or analogs according to the invention are those which facilitate specific detection of a IAP nucleic acid or amino acid sequence in a sample to be diagnosed. Particularly useful IAP fragments for this purpose include, without limitation, the amino acid fragments shown in Table 2.

All publications and patent applications mentioned in this specification are herein incorporated by reference to the same extent as if each independent publication or patent application was specifically and individually indicated to be incorporated by reference.

What is claimed is:

1. A substantially pure nucleic acid having the sequence of FIG. 5 (SEQ ID NO: 39), or degenerate variants thereof, and encoding the amino acid sequence of FIG. 5 (SEQ ID NO: 40).

2. A substantially pure nucleic acid having the sequence of FIG. 6 (SEQ ID NO: 41), or degenerate variants thereof, and encoding the amino acid sequence of FIG. 6 (SEQ ID NO: 42).

3. A substantially pure nucleic acid having the sequence of FIG. 1 (SEQ ID NO: 3), or degenerate variants thereof, and encoding the amino acid sequence of FIG. 1 (SEQ ID NO: 4).

4. A substantially pure nucleic acid having the sequence of FIG. 2 (SEQ ID NO: 5), or degenerate variants thereof, and encoding the amino acid sequence of FIG. 2 (SEQ ID NO: 6).

5. A substantially pure nucleic acid having the sequence of FIG. 3 (SEQ ID NO: 7), or degenerate variants thereof, and encoding the amino acid sequence of FIG. 3 (SEQ ID NO: 8).

6. A substantially pure nucleic acid having the sequence of FIG. 4 (SEQ ID NO: 9), or degenerate variants thereof, and encoding the amino acid sequence of FIG. 4 (SEQ ID NO: 10).

7. A substantially pure nucleic acid encoding a baculovirus inhibitor of apoptosis repeat (BIR) domain, said nucleic acid comprising a sequence selected from the group consisting of SEQ ID NO: 45, SEQ ID NO: 46, SEQ ID NO: 47, SEQ ID NO: 49, SEQ ID NO: 50, SEQ ID NO: 51, SEQ ID NO: 53, SEQ ID NO: 54, SEQ ID NO: 55, SEQ ID NO: 57, SEQ ID NO: 58, SEQ ID NO: 59, SEQ ID NO: 61, SEQ ID NO: 62, SEQ ID NO: 63, SEQ ID NO: 65, SEQ ID NO: 66, and SEQ ID NO: 67.

8. A substantially pure nucleic acid encoding a ring zinc finger (RZF) domain, said nucleic acid comprising a sequence selected from the group consisting of SEQ ID NO: 48, SEQ ID NO: 52, SEQ ID NO: 56, SEQ ID NO: 60, SEQ ID NO: 64, and SEQ ID NO: 68.

9. A method of producing a mammalian inhibitor of apoptosis protein (IAP) polypeptide comprising:

providing a cell transformed with a nucleic acid sequence encoding a mammalian IAP polypeptide positioned for expression in said cell, said polypeptide having the sequence of m-HIAP1 (SEQ ID NO: 39), m-HIAP2 (SEQ ID NO: 41), HIAP1 (SEQ ID NO: 5), HIAP2 (SEQ ID NO: 7), mXIAP (SEQ ID NO: 9), or XIAP (SEQ ID NO: 3);

culturing said transformed cell under conditions for expressing said nucleic acid; and producing said mammalian IAP polypeptide.

10. The method of claim 9, wherein said mammalian inhibitor of apoptosis protein (IAP) polypeptide is murine human inhibitor of apoptosis protein 1 (m-HIAP1) (SEQ ID NO: 39).

11. The method of claim 9, wherein said mammalian inhibitor of apoptosis protein (IAP) polypeptide is murine human inhibitor of apoptosis protein 2 (m-HIAP2) (SEQ ID NO: 41).

12. The method of claim 9, wherein said mammalian inhibitor of apoptosis protein (IAP) polypeptide is human inhibitor of apoptosis protein 1 (HIAP1) (SEQ ID NO: 5).

13. The method of claim 9, wherein said mammalian inhibitor of apoptosis protein (IAP) polypeptide is human inhibitor of apoptosis protein 2 (HIAP2) (SEQ ID NO: 7).

14. The method of claim 9, wherein said mammalian inhibitor of apoptosis protein (IAP) polypeptide is murine X-linked inhibitor of apoptosis protein (m-XIAP) (SEQ ID NO: 9).

15. The method of claim 9, wherein said mammalian inhibitor of apoptosis protein (IAP) polypeptide is human X-linked inhibitor of apoptosis protein (XIAP) (SEQ ID NO: 3).

* * * * *

SEQUENCE LISTING (1) GENERAL INFORMATION:

(iii) NUMBER OF SEQUENCES: 68

(2) INFORMATION FOR SEQ ID NO:1:

(i) SEQUENCE CHARACTERISTICS:
      (A) LENGTH: 46 amino acids
      (B) TYPE: amino acid
      (C) STRANDEDNESS: Not Relevant
      (D) TOPOLOGY: both (ii) MOLECULE TYPE: protein (ix) FEATURE:
      (D) OTHER INFORMATION: Xaa at positons 2, 3, 4, 5,
         6, 7, 9, 10, 11, 17, 18, 19, 20, 21, 23, 25, 30, 31, 32,
         34, 35, 38, 39, 40, 41, 42, and 45 may be any amino acid.
         Xaa at position 8 is Glu or Asp. Xaa at positions 14 &
         22 is Val or Ile.

(xi) SEQUENCE DESCRIPTION: SEQ ID NO:1:

Glu Xaa Xaa Xaa Xaa Xaa Xaa Xaa Xaa Xaa Cys Lys Xaa Cys Met
1               5                   10                  15

Xaa Xaa Xaa Xaa Xaa Xaa Xaa Phe Xaa Pro Cys Gly His Xaa Xaa Xaa
                20                  25                  30

Cys Xaa Xaa Cys Ala Xaa Xaa Xaa Xaa Xaa Cys Pro Xaa Cys
        35                  40                  45

(2) INFORMATION FOR SEQ ID NO:2:

(i) SEQUENCE CHARACTERISTICS:
       (A) LENGTH: 68 amino acids
       (B) TYPE: amino acid
       (C) STRANDEDNESS: Not Relevant
       (D) TOPOLOGY: both (ii) MOLECULE TYPE: protein (ix) FEATURE:
       (D) OTHER INFORMATION: Xaa at positions 1, 2, 3,
           6, 9, 10, 14, 15, 18, 19, 20, 21, 24, 30, 32, 33, 35, 37,
           40, 42, 43, 44, 45, 46, 47, 49, 50, 51, 53, 54, 55, 56,
           57, 59, 60, 61, 62, 64 and 66 may be any amino acid.
           Xaa at positions 13, 16 and 17 may be any amino acid or
           may be absent.

(xi) SEQUENCE DESCRIPTION: SEQ ID NO:2:

Xaa Xaa Xaa Arg Leu Xaa Thr Phe Xaa Xaa Trp Pro Xaa Xaa Xaa Xaa
1               5                   10                  15

Xaa Xaa Xaa Xaa Xaa Leu Ala Xaa Ala Gly Phe Tyr Tyr Xaa Gly Xaa
                20                  25                  30

Xaa Asp Xaa Val Xaa Cys Phe Xaa Cys Xaa Xaa Xaa Xaa Xaa Xaa Trp
        35                  40                  45

Xaa Xaa Xaa Asp Xaa Xaa Xaa Xaa Xaa His Xaa Xaa Xaa Xaa Pro Xaa
    50                  55                  60

Cys Xaa Phe Val
65

(2) INFORMATION FOR SEQ ID NO:3:

(i) SEQUENCE CHARACTERISTICS:
       (A) LENGTH: 2540 base pairs
       (B) TYPE: nucleic acid
       (C) STRANDEDNESS: both
       (D) TOPOLOGY: both (ii) MOLECULE TYPE: DNA (genomic)

(xi) SEQUENCE DESCRIPTION: SEQ ID NO:3:

```
GAAAAGGTGG ACAAGTCCTA TTTTCAAGAG AAGATGACTT TTAACAGTTT TGAAGGATCT      60

AAAACTTGTG TACCTGCAGA CATCAATAAG GAAGAAGAAT TTGTAGAAGA GTTTAATAGA     120

TTAAAAACTT TTGCTAATTT TCCAAGTGGT AGTCCTGTTT CAGCATCAAC ACTGGCACGA     180

GCAGGGTTTC TTTATACTGG TGAAGGAGAT ACCGTGCGGT GCTTTAGTTG TCATGCAGCT     240

GTAGATAGAT GGCAATATGG AGACTCAGCA GTTGGAAGAC ACAGGAAAGT ATCCCCAAAT     300

TGCAGATTTA TCAACGGCTT TTATCTTGAA AATAGTGCCA CGCAGTCTAC AAATTCTGGT     360

ATCCAGAATG GTCAGTACAA AGTTGAAAAC TATCTGGGAA GCAGAGATCA TTTTGCCTTA     420

GACAGGCCAT CTGAGACACA TGCAGACTAT CTTTTGAGAA CTGGGCAGGT TGTAGATATA     480

TCAGACACCA TATACCCGAG GAACCCTGCC ATGTATTGTG AAGAAGCTAG ATTAAAGTCC     540
```

```
TTTCAGAACT GGCCAGACTA TGCTCACCTA ACCCCAAGAG AGTTAGCAAG TGCTGGACTC      600

TACTACACAG GTATTGGTGA CCAAGTGCAG TGCTTTTGTT GTGGTGGAAA ACTGAAAAAT      660

TGGGAACCTT GTGATCGTGC CTGGTCAGAA CACAGGCGAC ACTTTCCTAA TTGCTTCTTT      720

GTTTTGGGCC GGAATCTTAA TATTCGAAGT GAATCTGATG CTGTGAGTTC TGATAGGAAT      780

TTCCCAAATT CAACAAATCT TCCAAGAAAT CCATCCATGG CAGATTATGA AGCACGGATC      840

TTTACTTTTG GACATGGAT ATACTCAGTT AACAAGGAGC AGCTTGCAAG AGCTGGATTT      900

TATGCTTTAG GTGAAGGTGA TAAAGTAAAG TGCTTTCACT GTGGAGGAGG GCTAACTGAT      960

TGGAAGCCCA GTGAAGACCC TTGGGAACAA CATGCTAAAT GGTATCCAGG GTGCAAATAT     1020

CTGTTAGAAC AGAAGGGACA AGAATATATA ACAATATTC ATTTAACTCA TTCACTTGAG     1080

GAGTGTCTGG TAAGAACTAC TGAGAAAACA CCATCACTAA CTAGAAGAAT TGATGATACC     1140

ATCTTCCAAA ATCCTATGGT ACAAGAAGCT ATACGAATGG GGTTCAGTTT CAAGGACATT     1200

AAGAAAATAA TGGAGGAAAA AATTCAGATA TCTGGGAGCA ACTATAAATC ACTTGAGGTT     1260

CTGGTTGCAG ATCTAGTGAA TGCTCAGAAA GACAGTATGC AAGATGAGTC AAGTCAGACT     1320

TCATTACAGA AAGAGATTAG TACTGAAGAG CAGCTAAGGC GCCTGCAAGA GGAGAAGCTT     1380

TGCAAAATCT GTATGGATAG AAATATTGCT ATCGTTTTTG TTCCTTGTGG ACATCTAGTC     1440

ACTTGTAAAC AATGTGCTGA AGCAGTTGAC AAGTGTCCCA TGTGCTACAC AGTCATTACT     1500

TTCAAGCAAA AAATTTTTAT GTCTTAATCT AACTCTATAG TAGGCATGTT ATGTTGTTCT     1560

TATTACCCTG ATTGAATGTG TGATGTGAAC TGACTTTAAG TAATCAGGAT TGAATTCCAT     1620

TAGCATTTGC TACCAAGTAG GAAAAAAAAT GTACATGGCA GTGTTTTAGT TGGCAATATA     1680

ATCTTTGAAT TTCTTGATTT TTCAGGGTAT TAGCTGTATT ATCCATTTTT TTTACTGTTA     1740

TTTAATTGAA ACCATAGACT AAGAATAAGA AGCATCATAC TATAACTGAA CACAATGTGT     1800

ATTCATAGTA TACTGATTTA ATTTCTAAGT GTAAGTGAAT TAATCATCTG GATTTTTTAT     1860

TCTTTTCAGA TAGGCTTAAC AAATGGAGCT TTCTGTATAT AAATGTGGAG ATTAGAGTTA     1920

ATCTCCCCAA TCACATAATT TGTTTTGTGT GAAAAAGGAA TAAATTGTTC CATGCTGGTG     1980

GAAAGATAGA GATTGTTTTT AGAGGTTGGT TGTTGTGTTT TAGGATTCTG TCCATTTTCT     2040

TGTAAAGGGA TAAACACGGA CGTGTGCGAA ATATGTTTGT AAAGTGATTT GCCATTGTTG     2100

AAAGCGTATT TAATGATAGA ATACTATCGA GCCAACATGT ACTGACATGG AAAGATGTCA     2160

GAGATATGTT AAGTGTAAAA TGCAAGTGGC GGGACACTAT GTATAGTCTG AGCCAGATCA     2220

AAGTATGTAT GTTGTTAATA TGCATAGAAC GAGAGATTTG GAAAGATATA CACCAAACTG     2280

TTAAATGTGG TTTCTCTTCG GGGAGGGGGG GATTGGGGGA GGGGCCCCAG AGGGGTTTTA     2340

GAGGGGCCTT TTCACTTTCG ACTTTTTTCA TTTTGTTCTG TTCGGATTTT TTATAAGTAT     2400

GTAGACCCCG AAGGGTTTTA TGGGAACTAA CATCAGTAAC CTAACCCCCG TGACTATCCT     2460

GTGCTCTTCC TAGGGAGCTG TGTTGTTCC CACCCACCAC CCTTCCCTCT GAACAAATGC     2520

CTGAGTGCTG GGGCACTTTN                                                 2540
```

(2) INFORMATION FOR SEQ ID NO:4:

(i) SEQUENCE CHARACTERISTICS:
        (A) LENGTH: 497 amino acids
        (B) TYPE: amino acid
        (C) STRANDEDNESS: unknown
        (D) TOPOLOGY: both (ii) MOLECULE TYPE: protein (xi) SEQUENCE DESCRIPTION: SEQ ID NO:4:

```
Met Thr Phe Asn Ser Phe Glu Gly Ser Lys Thr Cys Val Pro Ala Asp
1               5                   10                  15

Ile Asn Lys Glu Glu Glu Phe Val Glu Phe Asn Arg Leu Lys Thr
            20                  25                  30

Phe Ala Asn Phe Pro Ser Gly Ser Pro Val Ser Ala Ser Thr Leu Ala
            35                  40                  45

Arg Ala Gly Phe Leu Tyr Thr Gly Glu Gly Asp Thr Val Arg Cys Phe
        50                  55                  60

Ser Cys His Ala Ala Val Asp Arg Trp Gln Tyr Gly Asp Ser Ala Val
65                  70                  75                  80

Gly Arg His Arg Lys Val Ser Pro Asn Cys Arg Phe Ile Asn Gly Phe
                85                  90                  95

Tyr Leu Glu Asn Ser Ala Thr Gln Ser Thr Asn Ser Gly Ile Gln Asn
            100                 105                 110

Gly Gln Tyr Lys Val Glu Asn Tyr Leu Gly Ser Arg Asp His Phe Ala
        115                 120                 125

Leu Asp Arg Pro Ser Glu Thr His Ala Asp Tyr Leu Leu Arg Thr Gly
130                 135                 140

Gln Val Val Asp Ile Ser Asp Thr Ile Tyr Pro Arg Asn Pro Ala Met
145                 150                 155                 160

Tyr Cys Glu Glu Ala Arg Leu Lys Ser Phe Gln Asn Trp Pro Asp Tyr
                165                 170                 175

Ala His Leu Thr Pro Arg Glu Leu Ala Ser Ala Gly Leu Tyr Tyr Thr
            180                 185                 190

Gly Ile Gly Asp Gln Val Gln Cys Phe Cys Gly Gly Lys Leu Lys
        195                 200                 205

Asn Trp Glu Pro Cys Asp Arg Ala Trp Ser Glu His Arg Arg His Phe
210                 215                 220

Pro Asn Cys Phe Phe Val Leu Gly Arg Asn Leu Asn Ile Arg Ser Glu
225                 230                 235                 240

Ser Asp Ala Val Ser Ser Asp Arg Asn Phe Pro Asn Ser Thr Asn Leu
                245                 250                 255

Pro Arg Asn Pro Ser Met Ala Asp Tyr Glu Ala Arg Ile Phe Thr Phe
            260                 265                 270

Gly Thr Trp Ile Tyr Ser Val Asn Lys Glu Gln Leu Ala Arg Ala Gly
        275                 280                 285

Phe Tyr Ala Leu Gly Glu Gly Asp Lys Val Lys Cys Phe His Cys Gly
290                 295                 300

Gly Gly Leu Thr Asp Trp Lys Pro Ser Glu Asp Pro Trp Glu Gln His
305                 310                 315                 320

Ala Lys Trp Tyr Pro Gly Cys Lys Tyr Leu Leu Glu Gln Lys Gly Gln
                325                 330                 335

Glu Tyr Ile Asn Asn Ile His Leu Thr His Ser Leu Glu Glu Cys Leu
            340                 345                 350

Val Arg Thr Thr Glu Lys Thr Pro Ser Leu Thr Arg Arg Ile Asp Asp
        355                 360                 365

Thr Ile Phe Gln Asn Pro Met Val Gln Glu Ala Ile Arg Met Gly Phe
370                 375                 380

Ser Phe Lys Asp Ile Lys Lys Ile Met Glu Glu Lys Ile Gln Ile Ser
385                 390                 395                 400

Gly Ser Asn Tyr Lys Ser Leu Glu Val Leu Val Ala Asp Leu Val Asn
                405                 410                 415
```

```
Ala Gln Lys Asp Ser Met Gln Asp Glu Ser Ser Gln Thr Ser Leu Gln
            420                 425                 430

Lys Glu Ile Ser Thr Glu Glu Gln Leu Arg Arg Leu Gln Glu Glu Lys
        435                 440                 445

Leu Cys Lys Ile Cys Met Asp Arg Asn Ile Ala Ile Val Phe Val Pro
        450                 455                 460

Cys Gly His Leu Val Thr Cys Lys Gln Cys Ala Glu Ala Val Asp Lys
465                 470                 475                 480

Cys Pro Met Cys Tyr Thr Val Ile Thr Phe Lys Gln Lys Ile Phe Met
                485                 490                 495

Ser (2) INFORMATION FOR SEQ ID NO:5:

(i) SEQUENCE CHARACTERISTICS:
        (A) LENGTH: 2676 base pairs
        (B) TYPE: nucleic acid
        (C) STRANDEDNESS: both
        (D) TOPOLOGY: both (ii) MOLECULE TYPE: DNA (genomic)

(xi) SEQUENCE DESCRIPTION: SEQ ID NO:5:

TCCTTGAGAT GTATCAGTAT AGGATTTAGG ATCTCCATGT TGGAACTCTA AATGCATAGA      60

AATGGAAATA ATGGAAATTT TTCATTTTGG CTTTTCAGCC TAGTATTAAA ACTGATAAAA    120

GCAAAGCCAT GCACAAAACT ACCTCCCTAG AGAAAGGCTA GTCCCTTTTC TTCCCCATTC    180

ATTTCATTAT GAACATAGTA GAAAACAGCA TATTCTTATC AAATTTGATG AAAAGCGCCA    240

ACACGTTTGA ACTGAAATAC GACTTGTCAT GTGAACTGTA CCGAATGTCT ACGTATTCCA    300

CTTTTCCTGC TGGGGTTCCT GTCTCAGAAA GGAGTCTTGC TCGTGCTGGT TTCTATTACA    360

CTGGTGTGAA TGACAAGGTC AAATGCTTCT GTTGTGGCCT GATGCTGGAT AACTGGAAAA    420

GAGGAGACAG TCCTACTGAA AAGCATAAAA AGTTGTATCC TAGCTGCAGA TTCGTTCAGA    480

GTCTAAATTC CGTTAACAAC TTGGAAGCTA CCTCTCAGCC TACTTTTCCT TCTTCAGTAA    540

CACATTCCAC ACACTCATTA CTTCCGGGTA CAGAAAACAG TGGATATTTC CGTGGCTCTT    600

ATTCAAACTC TCCATCAAAT CCTGTAAACT CCAGAGCAAA TCAAGAATTT TCTGCCTTGA    660

TGAGAAGTTC CTACCCCTGT CCAATGAATA ACGAAAATGC CAGATTACTT ACTTTTCAGA    720

CATGGCCATT GACTTTTCTG TCGCCAACAG ATCTGGCACG AGCAGGCTTT TACTACATAG    780

GACCTGGAGA CAGAGTGGCT TGCTTTGCCT GTGGTGGAAA ATTGAGCAAT TGGGAACCGA    840

AGGATAATGC TATGTCAGAA CACCTGAGAC ATTTTCCCAA ATGCCCATTT ATAGAAAATC    900

AGCTTCAAGA CACTTCAAGA TACACAGTTT CTAATCTGAG CATGCAGACA CATGCAGCCC    960

GCTTTAAAAC ATTCTTTAAC TGGCCCTCTA GTGTTCTAGT TAATCCTGAG CAGCTTGCAA   1020

GTGCGGGTTT TTATTATGTG GGTAACAGTG ATGATGTCAA ATGCTTTTGC TGTGATGGTG   1080

GACTCAGGTG TTGGGAATCT GGAGATGATC CATGGGTTCA ACATGCCAAG TGGTTTCCAA   1140

GGTGTGAGTA CTTGATAAGA ATTAAAGGAC AGGAGTTCAT CCGTCAAGTT CAAGCCAGTT   1200

ACCCTCATCT ACTTGAACAG CTGCTATCCA CATCAGACAC CCAGGAGAT GAAAATGCAG    1260

AGTCATCAAT TATCCATTTG GAACCTGGAG AAGACCATTC AGAAGATGCA ATCATGATGA   1320

ATACTCCTGT GATTAATGCT GCCGTGGAAA TGGGCTTTAG TAGAAGCCTG GTAAAACAGA   1380

CAGTTCGAG AAAAATCCTA GCAACTGGAG AGAATTATAG ACTAGTCAAT GATCTTGTGT    1440
```

```
TAGACTTACT CAATGCAGAA GATGAAATAA GGGAAGAGGA GAGAGAAAGA GCAACTGAGG    1500

AAAAAGAATC AAATGATTTA TTATTAATCC GGAAGAATAG AATGGCACTT TTTCAACATT    1560

TGACTTGTGT AATTCCAATC CTGGATAGTC TACTAACTGC CGGAATTATT AATGAACAAG    1620

AACATGATGT TATTAAACAG AAGACACAGA CGTCTTTACA AGCAAGAGAA CTGATTGATA    1680

CGATTTTAGT AAAAGGAAAT ATTGCAGCCA CTGTATTCAG AAACTCTCTG CAAGAAGCTG    1740

AAGCTGTGTT ATATGAGCAT TTATTTGTGC AACAGGACAT AAAATATATT CCCACAGAAG    1800

ATGTTTCAGA TCTACCAGTG GAAGAACAAT TGCGGAGACT ACCAGAAGAA GAACATGTA     1860

AAGTGTGTAT GGACAAAGAA GTGTCCATAG TGTTTATTCC TTGTGGTCAT CTAGTAGTAT    1920

GCAAAGATTG TGCTCCTTCT TTAAGAAAGT GTCCTATTTG TAGGAGTACA ATCAAGGGTA    1980

CAGTTCGTAC ATTTCTTTCA TGAAGAAGAA CCAAAACATC GTCTAAACTT TAGAATTAAT    2040

TTATTAAATG TATTATAACT TTAACTTTTA TCCTAATTTG GTTTCCTTAA AATTTTTATT    2100

TATTTACAAC TCAAAAAACA TTGTTTTGTG TAACATATTT ATATATGTAT CTAAACCATA    2160

TGAACATATA TTTTTTAGAA ACTAAGAGAA TGATAGGCTT TTGTTCTTAT GAACGAAAAA    2220

GAGGTAGCAC TACAAACACA ATATTCAATC CAAATTTCAG CATTATTGAA ATTGTAAGTG    2280

AAGTAAAACT TAAGATATTT GAGTTAACCT TTAAGAATTT TAAATATTTT GGCATTGTAC    2340

TAATACCGGG AACATGAAGC CAGGTGTGGT GGTATGTACC TGTAGTCCCA GGCTGAGGCA    2400

AGAGAATTAC TTGAGCCCAG GAGTTTGAAT CCATCCTGGG CAGCATACTG AGACCCTGCC    2460

TTTAAAAACN AACAGNACCA AANCCAAACA CCAGGGACAC ATTTCTCTGT CTTTTTTGAT    2520

CAGTGTCCTA TACATCGAAG GTGTGCATAT ATGTTGAATC ACATTTTAGG GACATGGTGT    2580

TTTTATAAAG AATTCTGTGA GNAAAAATTT AATAAAGCAA CCAAATTACT CTTAAAAAAA    2640

AAAAAAAAAA AAAAAACTCG AGGGGCCCGT ACCAAT                               2676

(2) INFORMATION FOR SEQ ID NO:6:

(i) SEQUENCE CHARACTERISTICS:
        (A) LENGTH: 604 amino acids
        (B) TYPE: amino acid
        (C) STRANDEDNESS: Not Relevant
        (D) TOPOLOGY: both (ii) MOLECULE TYPE: protein (xi) SEQUENCE DESCRIPTION: SEQ ID NO:6:

Met Asn Ile Val Glu Asn Ser Ile Phe Leu Ser Asn Leu Met Lys Ser
1               5                   10                  15

Ala Asn Thr Phe Glu Leu Lys Tyr Asp Leu Ser Cys Glu Leu Tyr Arg
            20                  25                  30

Met Ser Thr Tyr Ser Thr Phe Pro Ala Gly Val Pro Val Ser Glu Arg
        35                  40                  45

Ser Leu Ala Arg Ala Gly Phe Tyr Thr Gly Val Asn Asp Lys Val
    50                  55                  60

Lys Cys Phe Cys Cys Gly Leu Met Leu Asp Asn Trp Lys Arg Gly Asp
65                  70                  75                  80

Ser Pro Thr Glu Lys His Lys Lys Leu Tyr Pro Ser Cys Arg Phe Val
                85                  90                  95

Gln Ser Leu Asn Ser Val Asn Asn Leu Glu Ala Thr Ser Gln Pro Thr
            100                 105                 110

Phe Pro Ser Ser Val Thr His Ser Thr His Ser Leu Leu Pro Gly Thr
        115                 120                 125
```

-continued

```
Glu Asn Ser Gly Tyr Phe Arg Gly Ser Tyr Ser Asn Ser Pro Ser Asn
            130                 135                 140

Pro Val Asn Ser Arg Ala Asn Gln Glu Phe Ser Ala Leu Met Arg Ser
145                 150                 155                 160

Ser Tyr Pro Cys Pro Met Asn Asn Glu Asn Ala Arg Leu Leu Thr Phe
                165                 170                 175

Gln Thr Trp Pro Leu Thr Phe Leu Ser Pro Thr Asp Leu Ala Arg Ala
            180                 185                 190

Gly Phe Tyr Tyr Ile Gly Pro Gly Asp Arg Val Ala Cys Phe Ala Cys
                195                 200                 205

Gly Gly Lys Leu Ser Asn Trp Glu Pro Lys Asp Asn Ala Met Ser Glu
210                 215                 220

His Leu Arg His Phe Pro Lys Cys Pro Phe Ile Glu Asn Gln Leu Gln
225                 230                 235                 240

Asp Thr Ser Arg Tyr Thr Val Ser Asn Leu Ser Met Gln Thr His Ala
                245                 250                 255

Ala Arg Phe Lys Thr Phe Phe Asn Trp Pro Ser Ser Val Leu Val Asn
            260                 265                 270

Pro Glu Gln Leu Ala Ser Ala Gly Phe Tyr Tyr Val Gly Asn Ser Asp
            275                 280                 285

Asp Val Lys Cys Phe Cys Cys Asp Gly Gly Leu Arg Cys Trp Glu Ser
290                 295                 300

Gly Asp Asp Pro Trp Val Gln His Ala Lys Trp Phe Pro Arg Cys Glu
305                 310                 315                 320

Tyr Leu Ile Arg Ile Lys Gly Gln Glu Phe Ile Arg Gln Val Gln Ala
                325                 330                 335

Ser Tyr Pro His Leu Leu Glu Gln Leu Leu Ser Thr Ser Asp Ser Pro
            340                 345                 350

Gly Asp Glu Asn Ala Glu Ser Ser Ile Ile His Leu Glu Pro Gly Glu
            355                 360                 365

Asp His Ser Glu Asp Ala Ile Met Met Asn Thr Pro Val Ile Asn Ala
            370                 375                 380

Ala Val Glu Met Gly Phe Ser Arg Ser Leu Val Lys Gln Thr Val Gln
385                 390                 395                 400

Arg Lys Ile Leu Ala Thr Gly Glu Asn Tyr Arg Leu Val Asn Asp Leu
                405                 410                 415

Val Leu Asp Leu Leu Asn Ala Glu Asp Glu Ile Arg Glu Glu Glu Arg
            420                 425                 430

Glu Arg Ala Thr Glu Glu Lys Glu Ser Asn Asp Leu Leu Leu Ile Arg
            435                 440                 445

Lys Asn Arg Met Ala Leu Phe Gln His Leu Thr Cys Val Ile Pro Ile
450                 455                 460

Leu Asp Ser Leu Leu Thr Ala Gly Ile Ile Asn Glu Gln Glu His Asp
465                 470                 475                 480

Val Ile Lys Gln Lys Thr Gln Thr Ser Leu Gln Ala Arg Glu Leu Ile
                485                 490                 495

Asp Thr Ile Leu Val Lys Gly Asn Ile Ala Ala Thr Val Phe Arg Asn
            500                 505                 510

Ser Leu Gln Glu Ala Glu Ala Val Leu Tyr Glu His Leu Phe Val Gln
            515                 520                 525

Gln Asp Ile Lys Tyr Ile Pro Thr Glu Asp Val Ser Asp Leu Pro Val
530                 535                 540

Glu Glu Gln Leu Arg Arg Leu Pro Glu Glu Arg Thr Cys Lys Val Cys
```

```
545                 550                 555                 560
Met Asp Lys Glu Val Ser Ile Val Phe Ile Pro Cys Gly His Leu Val
                565                 570                 575
Val Cys Lys Asp Cys Ala Pro Ser Leu Arg Lys Cys Pro Ile Cys Arg
                580                 585                 590
Ser Thr Ile Lys Gly Thr Val Arg Thr Phe Leu Ser
            595                 600
```

(2) INFORMATION FOR SEQ ID NO:7:

(i) SEQUENCE CHARACTERISTICS:
        (A) LENGTH: 2580 base pairs
        (B) TYPE: nucleic acid
        (C) STRANDEDNESS: both
        (D) TOPOLOGY: both (ii) MOLECULE TYPE: DNA (genomic)

(xi) SEQUENCE DESCRIPTION: SEQ ID NO:7:

```
TTAGGTTACC TGAAAGAGTT ACTACAACCC CAAAGAGTTG TGTTCTAAGT AGTATCTTGG      60

TAATTCAGAG AGATACTCAT CCTACCTGAA TATAAACTGA GATAAATCCA GTAAAGAAAG     120

TGTAGTAAAT TCTACATAAG AGTCTATCAT TGATTTCTTT TTGTGGTGGA AATCTTAGTT     180

CATGTGAAGA AATTTCATGT GAATGTTTTA GCTATCAAAC AGTACTGTCA CCTACTCATG     240

CACAAAACTG CCTCCCAAAG ACTTTTCCCA GGTCCCTCGT ATCAAAACAT AAGAGTATA      300

ATGGAAGATA GCACGATCTT GTCAGATTGG ACAAACAGCA ACAAACAAAA AATGAAGTAT     360

GACTTTTCCT GTGAACTCTA CAGAATGTCT ACATATTCAA CTTTCCCCGC CGGGGTGCCT     420

GTCTCAGAAA GGAGTCTTGC TCGTGCTGGT TTTTATTATA CTGGTGTGAA TGACAAGGTC     480

AAATGCTTCT GTTGTGGCCT GATGCTGGAT AACTGGAAAC TAGGAGACAG TCCTATTCAA     540

AAGCATAAAC AGCTATATCC TAGCTGTAGC TTTATTCAGA ATCTGGTTTC AGCTAGTCTG     600

GGATCCACCT CTAAGAATAC GTCTCCAATG AGAAACAGTT TTGCACATTC ATTATCTCCC     660

ACCTTGGAAC ATAGTAGCTT GTTCAGTGGT TCTTACTCCA GCCTTCCTCC AAACCCTCTT     720

AATTCTAGAG CAGTTGAAGA CATCTCTTCA TCGAGGACTA ACCCCTACAG TTATGCAATG     780

AGTACTGAAG AAGCCAGATT TCTTACCTAC CATATGTGGC CATTAACTTT TTTGTCACCA     840

TCAGAATTGG CAAGAGCTGG TTTTTATTAT ATAGGACCTG GAGATAGGGT AGCCTGCTTT     900

GCCTGTGGTG GGAAGCTCAG TAACTGGGAA CCAAAGGATG ATGCTATGTC AGAACACCGG     960

AGGCATTTTC CCAACTGTCC ATTTTTGGAA AATTCTCTAG AAACTCTGAG GTTTAGCATT    1020

TCAAATCTGA GCATGCAGAC ACATGCAGCT CGAATGAGAA CATTTATGTA CTGGCCATCT    1080

AGTGTTCCAG TTCAGCCTGA GCAGCTTGCA AGTGCTGGTT TTTATTATGT GGGTCGCAAT    1140

GATGATGTCA AATGCTTTGG TTGTGATGGT GGCTTGAGGT GTTGGGAATC TGGAGATGAT    1200

CCATGGGTAG AACATGCCAA GTGGTTTCCA AGGTGTGAGT TCTTGATACG AATGAAAGGC    1260

CAAGAGTTTG TTGATGAGAT TCAAGGTAGA ATCCTCATC TTCTTGAACA GCTGTTGTCA    1320

ACTTCAGATA CCACTGGAGA AGAAAATGCT GACCCACCAA TTATTCATTT TGGACCTGGA    1380

GAAAGTTCTT CAGAAGATGC TGTCATGATG AATACACCTG TGGTTAAATC TGCCTTGGAA    1440

ATGGGCTTTA ATAGAGACCT GGTGAAACAA ACAGTTCTAA GTAAAATCCT GACAACTGGA    1500

GAGAACTATA AACAGTTAA TGATATTGTG TCAGCACTTC TTAATGCTGA AGATGAAAAA     1560

AGAGAAGAGG AGAAGGAAAA ACAAGCTGAA GAAATGGCAT CAGATGATTT GTCATTAATT    1620

CGGAAGAACA GAATGGCTCT CTTTCAACAA TTGACATGTG TGCTTCCTAT CCTGGATAAT    1680
```

```
CTTTTAAAGG CCAATGTAAT TAATAAACAG GAACATGATA TTATTAAACA AAAAACACAG    1740

ATACCTTTAC AAGCGAGAGA ACTGATTGAT ACCATTTGGG TTAAAGGAAA TGCTGCGGCC    1800

AACATCTTCA AAAACTGTCT AAAAGAAATT GACTCTACAT TGTATAAGAA CTTATTTGTG    1860

GATAAGAATA TGAAGTATAT TCCAACAGAA GATGTTTCAG GTCTGTCACT GGAAGAACAA    1920

TTGAGGAGGT TGCAAGAAGA ACGAACTTGT AAAGTGTGTA TGGACAAAGA AGTTTCTGTT    1980

GTATTTATTC CTTGTGGTCA TCTGGTAGTA TGCCAGGAAT GTGCCCCTTC TCTAAGAAAA    2040

TGCCCTATTT GCAGGGGTAT AATCAAGGGT ACTGTTCGTA CATTTCTCTC TTAAAGAAAA    2100

ATAGTCTATA TTTTAACCTG CATAAAAAGG TCTTTAAAAT ATTGTTGAAC ACTTGAAGCC    2160

ATCTAAAGTA AAAAGGGAAT TATGAGTTTT TCAATTAGTA ACATTCATGT TCTAGTCTGC    2220

TTTGGTACTA ATAATCTTGT TTCTGAAAAG ATGGTATCAT ATATTTAATC TTAATCTGTT    2280

TATTTACAAG GGAAGATTTA TGTTTGGTGA ACTATATTAG TATGTATGTG TACCTAAGGG    2340

AGTAGCGTCN CTGCTTGTTA TGCATCATTT CAGGAGTTAC TGGATTTGTT GTTCTTTCAG    2400

AAAGCTTTGA ANACTAAATT ATAGTGTAGA AAAGAACTGG AAACCAGGAA CTCTGGAGTT    2460

CATCAGAGTT ATGGTGCCGA ATTGTCTTTG GTGCTTTTCA CTTGTGTTTT AAAATAAGGA    2520

TTTTTCTCTT ATTTCTCCCC CTAGTTTGTG AGAAACATCT CAATAAAGTG CTTTAAAAAG    2580

(2) INFORMATION FOR SEQ ID NO:8:

(i) SEQUENCE CHARACTERISTICS:
        (A) LENGTH: 618 amino acids
        (B) TYPE: amino acid
        (C) STRANDEDNESS: Not Relevant
        (D) TOPOLOGY: both (ii) MOLECULE TYPE: protein (xi) SEQUENCE DESCRIPTION: SEQ ID NO:8:

Met His Lys Thr Ala Ser Gln Arg Leu Phe Pro Gly Pro Ser Tyr Gln
1               5                   10                  15

Asn Ile Lys Ser Ile Met Glu Asp Ser Thr Ile Leu Ser Asp Trp Thr
            20                  25                  30

Asn Ser Asn Lys Gln Lys Met Lys Tyr Asp Phe Ser Cys Glu Leu Tyr
        35                  40                  45

Arg Met Ser Thr Tyr Ser Thr Phe Pro Ala Gly Val Pro Val Ser Glu
    50                  55                  60

Arg Ser Leu Ala Arg Ala Gly Phe Tyr Tyr Thr Gly Val Asn Asp Lys
65                  70                  75                  80

Val Lys Cys Phe Cys Cys Gly Leu Met Leu Asp Asn Trp Lys Leu Gly
                85                  90                  95

Asp Ser Pro Ile Gln Lys His Lys Gln Leu Tyr Pro Ser Cys Ser Phe
            100                 105                 110

Ile Gln Asn Leu Val Ser Ala Ser Leu Gly Ser Thr Ser Lys Asn Thr
        115                 120                 125

Ser Pro Met Arg Asn Ser Phe Ala His Ser Leu Ser Pro Thr Leu Glu
    130                 135                 140

His Ser Ser Leu Phe Ser Gly Ser Tyr Ser Ser Leu Pro Pro Asn Pro
145                 150                 155                 160

Leu Asn Ser Arg Ala Val Glu Asp Ile Ser Ser Ser Arg Thr Asn Pro
                165                 170                 175

Tyr Ser Tyr Ala Met Ser Thr Glu Glu Ala Arg Phe Leu Thr Tyr His
            180                 185                 190
```

-continued

```
Met Trp Pro Leu Thr Phe Leu Ser Pro Ser Glu Leu Ala Arg Ala Gly
            195                 200                 205

Phe Tyr Tyr Ile Gly Pro Gly Asp Arg Val Ala Cys Phe Ala Cys Gly
            210                 215                 220

Gly Lys Leu Ser Asn Trp Glu Pro Lys Asp Asp Ala Met Ser Glu His
225                 230                 235                 240

Arg Arg His Phe Pro Asn Cys Pro Phe Leu Glu Asn Ser Leu Glu Thr
                245                 250                 255

Leu Arg Phe Ser Ile Ser Asn Leu Ser Met Gln Thr His Ala Ala Arg
            260                 265                 270

Met Arg Thr Phe Met Tyr Trp Pro Ser Ser Val Pro Val Gln Pro Glu
            275                 280                 285

Gln Leu Ala Ser Ala Gly Phe Tyr Tyr Val Gly Arg Asn Asp Asp Val
290                 295                 300

Lys Cys Phe Gly Cys Asp Gly Gly Leu Arg Cys Trp Glu Ser Gly Asp
305                 310                 315                 320

Asp Pro Trp Val Glu His Ala Lys Trp Phe Pro Arg Cys Glu Phe Leu
                325                 330                 335

Ile Arg Met Lys Gly Gln Glu Phe Val Asp Glu Ile Gln Gly Arg Tyr
            340                 345                 350

Pro His Leu Leu Glu Gln Leu Leu Ser Thr Ser Asp Thr Thr Gly Glu
            355                 360                 365

Glu Asn Ala Asp Pro Pro Ile Ile His Phe Gly Pro Gly Glu Ser Ser
            370                 375                 380

Ser Glu Asp Ala Val Met Met Asn Thr Pro Val Val Lys Ser Ala Leu
385                 390                 395                 400

Glu Met Gly Phe Asn Arg Asp Leu Val Lys Gln Thr Val Leu Ser Lys
                405                 410                 415

Ile Leu Thr Thr Gly Glu Asn Tyr Lys Thr Val Asn Asp Ile Val Ser
            420                 425                 430

Ala Leu Leu Asn Ala Glu Asp Glu Lys Arg Glu Glu Lys Glu Lys
            435                 440                 445

Gln Ala Glu Glu Met Ala Ser Asp Asp Leu Ser Leu Ile Arg Lys Asn
450                 455                 460

Arg Met Ala Leu Phe Gln Gln Leu Thr Cys Val Leu Pro Ile Leu Asp
465                 470                 475                 480

Asn Leu Leu Lys Ala Asn Val Ile Asn Lys Gln Glu His Asp Ile Ile
                485                 490                 495

Lys Gln Lys Thr Gln Ile Pro Leu Gln Ala Arg Glu Leu Ile Asp Thr
            500                 505                 510

Ile Trp Val Lys Gly Asn Ala Ala Asn Ile Phe Lys Asn Cys Leu
            515                 520                 525

Lys Glu Ile Asp Ser Thr Leu Tyr Lys Asn Leu Phe Val Asp Lys Asn
            530                 535                 540

Met Lys Tyr Ile Pro Thr Glu Asp Val Ser Gly Leu Ser Leu Glu Glu
545                 550                 555                 560

Gln Leu Arg Arg Leu Gln Glu Glu Arg Thr Cys Lys Val Cys Met Asp
                565                 570                 575

Lys Glu Val Ser Val Val Phe Ile Pro Cys Gly His Leu Val Val Cys
            580                 585                 590

Gln Glu Cys Ala Pro Ser Leu Arg Lys Cys Pro Ile Cys Arg Gly Ile
            595                 600                 605
```

```
Ile Lys Gly Thr Val Arg Thr Phe Leu Ser
    610                 615
```

(2) INFORMATION FOR SEQ ID NO:9:

(i) SEQUENCE CHARACTERISTICS:
        (A) LENGTH: 2100 base pairs
        (B) TYPE: nucleic acid
        (C) STRANDEDNESS: both
        (D) TOPOLOGY: both (ii) MOLECULE TYPE: DNA (genomic)

(xi) SEQUENCE DESCRIPTION: SEQ ID NO:9:

```
GACACTCTGC TGGGCGGCGG GCCGCCCTCC TCCGGGACCT CCCCTCGGGA ACCGTCGCCC      60

GCGGCGCTTA GTTAGGACTG GAGTGCTTGG CGCGAAAAGG TGGACAAGTC CTATTTTCCA     120

GAGAAGATGA CTTTTAACAG TTTTGAAGGA ACTAGAACTT TTGTACTTGC AGACACCAAT     180

AAGGATGAAG AATTTGTAGA AGAGTTTAAT AGATTAAAAA CATTTGCTAA CTTCCCAAGT     240

AGTAGTCCTG TTTCAGCATC AACATTGGCG CGAGCTGGGT TTCTTTATAC CGGTGAAGGA     300

GACACCGTGC AATGTTTCAG TTGTCATGCG GCAATAGATA GATGGCAGTA TGGAGACTCA     360

GCTGTTGGAA GACACAGGAG AATATCCCCA AATTGCAGAT TTATCAATGG TTTTTATTTT     420

GAAAATGGTG CTGCACAGTC TACAAATCCT GGTATCCAAA ATGGCCAGTA CAAATCTGAA     480

AACTGTGTGG GAAATAGAAA TCCTTTTGCC CCTGACAGGC CACCTGAGAC TCATGCTGAT     540

TATCTCTTGA GAACTGGACA GGTTGTAGAT ATTTCAGACA CCATATACCC GAGGAACCCT     600

GCCATGTGTA GTGAAGAAGC CAGATTGAAG TCATTTCAGA ACTGGCCGGA CTATGCTCAT     660

TTAACCCCCA GAGAGTTAGC TAGTGCTGGC CTCTACTACA CAGGGGCTGA TGATCAAGTG     720

CAATGCTTTT GTTGTGGGGG AAAACTGAAA AATTGGGAAC CCTGTGATCG TGCCTGGTCA     780

GAACACAGGA GACACTTTCC CAATTGCTTT TTTGTTTTGG GCCGGAACGT TAATGTTCGA     840

AGTGAATCTG GTGTGAGTTC TGATAGGAAT TTCCCAAATT CAACAAACTC TCCAAGAAAT     900

CCAGCCATGG CAGAATATGA AGCACGGATC GTTACTTTTG GAACATGGAT ATACTCAGTT     960

AACAAGGAGC AGCTTGCAAG AGCTGGATTT TATGCTTTAG GTGAAGGCGA TAAAGTGAAG    1020

TGCTTCCACT GTGGAGGAGG GCTCACGGAT TGGAAGCCAA GTGAAGACCC CTGGGACCAG    1080

CATGCTAAGT GCTACCCAGG GTGCAAATAC CTATTGGATG AGAAGGGGCA AGAATATATA    1140

AATAATATTC ATTTAACCCA TCCACTTGAG GAATCTTTGG GAAGAACTGC TGAAAAAACA    1200

CCACCGCTAA CTAAAAAAAT CGATGATACC ATCTTCCAGA ATCCTATGGT GCAAGAAGCT    1260

ATACGAATGG GATTTAGCTT CAAGGACCTT AAGAAAACAA TGGAAGAAAA AATCCAAACA    1320

TCCGGGAGCA GCTATCTATC ACTTGAGGTC CTGATTGCAG ATCTTGTGAG TGCTCAGAAA    1380

GATAATACGG AGGATGAGTC AAGTCAAACT TCATTGCAGA AAGACATTAG TACTGAAGAG    1440

CAGCTAAGGC GCCTACAAGA GGAGAAGCTT TCCAAAATCT GTATGGATAG AAATATTGCT    1500

ATCGTTTTTT TTCCTTGTGG ACATCTGGCC ACTTGTAAAC AGTGTGCAGA AGCAGTTGAC    1560

AAATGTCCCA TGTGCTACAC CGTCATTACG TTCAACCAAA AAATTTTTAT GTCTTAGTGG    1620

GGCACCACAT GTTATGTTCT TCTTGCTCTA ATTGAATGTG TAATGGGAGC GAACTTTAAG    1680

TAATCCTGCA TTTGCATTCC ATTAGCATCC TGCTGTTTCC AAATGGAGAC CAATGCTAAC    1740

AGCACTGTTT CCGTCTAAAC ATTCAATTTC TGGATCTTTC GAGTTATCAG CTGTATCATT    1800

TAGCCAGTGT TTTACTCGAT TGAAACCTTA GACAGAGAAG CATTTTATAG CTTTTCACAT    1860

GTATATTGGT AGTACACTGA CTTGATTTCT ATATGTAAGT GAATTCATCA CCTGCATGTT    1920
```

```
TCATGCCTTT TGCATAAGCT TAACAAATGG AGTGTTCTGT ATAAGCATGG AGATGTGATG      1980

GAATCTGCCC AATGACTTTA ATTGGCTTAT TGTAAACACG GAAAGAACTG CCCCACGCTG      2040

CTGGGAGGAT AAAGATTGTT TTAGATGCTC ACTTCTGTGT TTTAGGATTC TGCCCATTTA      2100
```

(2) INFORMATION FOR SEQ ID NO:10:

(i) SEQUENCE CHARACTERISTICS:
        (A) LENGTH: 496 amino acids
        (B) TYPE: amino acid
        (C) STRANDEDNESS: Not Relevant
        (D) TOPOLOGY: both (ii) MOLECULE TYPE: protein (xi) SEQUENCE DESCRIPTION: SEQ ID NO:10:

```
Met Thr Phe Asn Ser Phe Glu Gly Thr Arg Thr Phe Val Leu Ala Asp
1               5                   10                  15

Thr Asn Lys Asp Glu Glu Phe Val Glu Glu Phe Asn Arg Leu Lys Thr
            20                  25                  30

Phe Ala Asn Phe Pro Ser Ser Pro Val Ser Ala Ser Thr Leu Ala
        35                  40                  45

Arg Ala Gly Phe Leu Tyr Thr Gly Glu Gly Asp Thr Val Gln Cys Phe
    50                  55                  60

Ser Cys His Ala Ala Ile Asp Arg Trp Gln Tyr Gly Asp Ser Ala Val
65              70                  75                  80

Gly Arg His Arg Arg Ile Ser Pro Asn Cys Arg Phe Ile Asn Gly Phe
                85                  90                  95

Tyr Phe Glu Asn Gly Ala Ala Gln Ser Thr Asn Pro Gly Ile Gln Asn
            100                 105                 110

Gly Gln Tyr Lys Ser Glu Asn Cys Val Gly Asn Arg Asn Pro Phe Ala
        115                 120                 125

Pro Asp Arg Pro Pro Glu Thr His Ala Asp Tyr Leu Leu Arg Thr Gly
    130                 135                 140

Gln Val Val Asp Ile Ser Asp Thr Ile Tyr Pro Arg Asn Pro Ala Met
145                 150                 155                 160

Cys Ser Glu Glu Ala Arg Leu Lys Ser Phe Gln Asn Trp Pro Asp Tyr
                165                 170                 175

Ala His Leu Thr Pro Arg Glu Leu Ala Ser Ala Gly Leu Tyr Tyr Thr
            180                 185                 190

Gly Ala Asp Asp Gln Val Gln Cys Phe Cys Gly Gly Lys Leu Lys
        195                 200                 205

Asn Trp Glu Pro Cys Asp Arg Ala Trp Ser Glu His Arg Arg His Phe
    210                 215                 220

Pro Asn Cys Phe Phe Val Leu Gly Arg Asn Val Asn Val Arg Ser Glu
225                 230                 235                 240

Ser Gly Val Ser Ser Asp Arg Asn Phe Pro Asn Ser Thr Asn Ser Pro
                245                 250                 255

Arg Asn Pro Ala Met Ala Glu Tyr Glu Ala Arg Ile Val Thr Phe Gly
            260                 265                 270

Thr Trp Ile Tyr Ser Val Asn Lys Glu Gln Leu Ala Arg Ala Gly Phe
        275                 280                 285

Tyr Ala Leu Gly Glu Gly Asp Lys Val Lys Cys Phe His Cys Gly Gly
    290                 295                 300

Gly Leu Thr Asp Trp Lys Pro Ser Glu Asp Pro Trp Asp Gln His Ala
305                 310                 315                 320
```

```
Lys Cys Tyr Pro Gly Cys Lys Tyr Leu Leu Asp Glu Lys Gly Gln Glu
                325                 330                 335

Tyr Ile Asn Asn Ile His Leu Thr His Pro Leu Glu Glu Ser Leu Gly
            340                 345                 350

Arg Thr Ala Glu Lys Thr Pro Pro Leu Thr Lys Lys Ile Asp Asp Thr
        355                 360                 365

Ile Phe Gln Asn Pro Met Val Gln Glu Ala Ile Arg Met Gly Phe Ser
    370                 375                 380

Phe Lys Asp Leu Lys Lys Thr Met Glu Glu Lys Ile Gln Thr Ser Gly
385                 390                 395                 400

Ser Ser Tyr Leu Ser Leu Glu Val Leu Ile Ala Asp Leu Val Ser Ala
                405                 410                 415

Gln Lys Asp Asn Thr Glu Asp Glu Ser Ser Gln Thr Ser Leu Gln Lys
                420                 425                 430

Asp Ile Ser Thr Glu Glu Leu Arg Arg Leu Gln Glu Glu Lys Leu
                435                 440                 445

Ser Lys Ile Cys Met Asp Arg Asn Ile Ala Ile Val Phe Phe Pro Cys
    450                 455                 460

Gly His Leu Ala Thr Cys Lys Gln Cys Ala Glu Ala Val Asp Lys Cys
465                 470                 475                 480

Pro Met Cys Tyr Thr Val Ile Thr Phe Asn Gln Lys Ile Phe Met Ser
                485                 490                 495

(2) INFORMATION FOR SEQ ID NO:11:

(i) SEQUENCE CHARACTERISTICS:
        (A) LENGTH: 67 amino acids
        (B) TYPE: amino acid
        (C) STRANDEDNESS: Not Relevant
        (D) TOPOLOGY: both (ii) MOLECULE TYPE: protein (xi) SEQUENCE DESCRIPTION: SEQ ID NO:11:

Lys Ala Ala Arg Leu Gly Thr Tyr Thr Asn Trp Pro Val Gln Phe Leu
1               5                   10                  15

Glu Pro Ser Arg Met Ala Ala Ser Gly Phe Tyr Tyr Leu Gly Arg Gly
                20                  25                  30

Asp Glu Val Arg Cys Ala Phe Cys Lys Val Glu Ile Thr Asn Trp Val
            35                  40                  45

Arg Gly Asp Asp Pro Glu Thr Asp His Lys Arg Trp Ala Pro Gln Cys
        50                  55                  60

Pro Phe Val
65

(2) INFORMATION FOR SEQ ID NO:12:

(i) SEQUENCE CHARACTERISTICS:
        (A) LENGTH: 275 amino acids
        (B) TYPE: amino acid
        (C) STRANDEDNESS: Not Relevant
        (D) TOPOLOGY: both (ii) MOLECULE TYPE: protein (xi) SEQUENCE DESCRIPTION: SEQ ID NO:12:

Met Ser Asp Leu Arg Leu Glu Glu Val Arg Leu Asn Thr Phe Glu Lys
1               5                   10                  15

Trp Pro Val Ser Phe Leu Ser Pro Glu Thr Met Ala Lys Asn Gly Phe
```

```
                    20                  25                  30
Tyr Tyr Leu Gly Arg Ser Asp Glu Val Arg Cys Ala Phe Cys Lys Val
                35                  40                  45
Glu Ile Met Arg Trp Lys Glu Gly Glu Asp Pro Ala Ala Asp His Lys
 50                  55                  60
Lys Trp Ala Pro Gln Cys Pro Phe Val Lys Gly Ile Asp Val Cys Gly
 65                  70                  75                  80
Ser Ile Val Thr Thr Asn Asn Ile Gln Asn Thr Thr His Asp Thr
                85                  90                  95
Ile Ile Gly Pro Ala His Pro Lys Tyr Ala His Glu Ala Ala Arg Val
                100                 105                 110
Lys Ser Phe His Asn Trp Pro Arg Cys Met Lys Gln Arg Pro Glu Gln
                115                 120                 125
Met Ala Asp Ala Gly Phe Phe Tyr Thr Gly Tyr Gly Asp Asn Thr Lys
                130                 135                 140
Cys Phe Tyr Cys Asp Gly Gly Leu Lys Asp Trp Glu Pro Glu Asp Val
 145                 150                 155                 160
Pro Trp Glu Gln His Val Arg Trp Phe Asp Arg Cys Ala Tyr Val Gln
                165                 170                 175
Leu Val Lys Gly Arg Asp Tyr Val Gln Lys Val Ile Thr Glu Ala Cys
                180                 185                 190
Val Leu Pro Gly Glu Asn Thr Thr Val Ser Thr Ala Ala Pro Val Ser
                195                 200                 205
Glu Pro Ile Pro Glu Thr Lys Ile Glu Lys Glu Pro Gln Val Glu Asp
                210                 215                 220
Ser Lys Leu Cys Lys Ile Cys Tyr Val Glu Glu Cys Ile Val Cys Phe
 225                 230                 235                 240
Val Pro Cys Gly His Val Val Ala Cys Ala Lys Cys Ala Leu Ser Val
                245                 250                 255
Asp Lys Cys Pro Met Cys Arg Lys Ile Val Thr Ser Val Leu Lys Val
                260                 265                 270
Tyr Phe Ser
 275

(2) INFORMATION FOR SEQ ID NO:13:

(i) SEQUENCE CHARACTERISTICS:
        (A) LENGTH: 498 amino acids
        (B) TYPE: amino acid
        (C) STRANDEDNESS: Not Relevant
        (D) TOPOLOGY: both (ii) MOLECULE TYPE: protein (xi) SEQUENCE DESCRIPTION: SEQ ID NO:13:

Met Thr Glu Leu Gly Met Glu Leu Glu Ser Val Arg Leu Ala Thr Phe
 1                   5                  10                  15
Gly Glu Trp Pro Leu Asn Ala Pro Val Ser Ala Glu Asp Leu Val Ala
                20                  25                  30
Asn Gly Phe Phe Ala Thr Gly Lys Trp Leu Glu Ala Glu Cys His Phe
                35                  40                  45
Cys His Val Arg Ile Asp Arg Trp Glu Tyr Gly Asp Gln Val Ala Glu
 50                  55                  60
Arg His Arg Arg Ser Ser Pro Ile Cys Ser Met Val Leu Ala Pro Asn
 65                  70                  75                  80
His Cys Gly Asn Val Pro Arg Ser Gln Glu Ser Asp Asn Glu Gly Asn
```

-continued

```
                85                  90                  95
Ser Val Val Asp Ser Pro Glu Ser Cys Ser Cys Pro Asp Leu Leu Leu
                100                 105                 110
Glu Ala Asn Arg Leu Val Thr Phe Lys Asp Trp Pro Asn Pro Asn Ile
                115                 120                 125
Thr Pro Gln Ala Leu Ala Lys Ala Gly Phe Tyr Tyr Leu Asn Arg Leu
            130                 135                 140
Asp His Val Lys Cys Val Trp Cys Asn Gly Val Ile Ala Lys Trp Glu
145                 150                 155                 160
Lys Asn Asp Asn Ala Phe Glu Glu His Lys Arg Phe Phe Pro Gln Cys
                165                 170                 175
Pro Arg Val Gln Met Gly Pro Leu Ile Glu Phe Ala Thr Gly Lys Asn
                180                 185                 190
Leu Asp Glu Leu Gly Ile Gln Pro Thr Thr Leu Pro Leu Arg Pro Lys
                195                 200                 205
Tyr Ala Cys Val Asp Ala Arg Leu Arg Thr Phe Thr Asp Trp Pro Ile
            210                 215                 220
Ser Asn Ile Gln Pro Ala Ser Ala Leu Ala Gln Ala Gly Leu Tyr Tyr
225                 230                 235                 240
Gln Lys Ile Gly Asp Gln Val Arg Cys Phe His Cys Asn Ile Gly Leu
                245                 250                 255
Arg Ser Trp Gln Lys Glu Asp Glu Pro Trp Phe Glu His Ala Lys Trp
                260                 265                 270
Ser Pro Lys Cys Gln Phe Val Leu Leu Ala Lys Gly Pro Ala Tyr Val
                275                 280                 285
Ser Glu Val Leu Ala Thr Thr Ala Ala Asn Ala Ser Ser Gln Pro Ala
            290                 295                 300
Thr Ala Pro Ala Pro Thr Leu Gln Ala Asp Val Leu Met Asp Glu Ala
305                 310                 315                 320
Pro Ala Lys Glu Ala Leu Thr Leu Gly Ile Asp Gly Gly Val Val Arg
                325                 330                 335
Asn Ala Ile Gln Arg Lys Leu Leu Ser Ser Gly Cys Ala Phe Ser Thr
                340                 345                 350
Leu Asp Glu Leu Leu His Asp Ile Phe Asp Asp Ala Gly Ala Gly Ala
            355                 360                 365
Ala Leu Glu Val Arg Glu Pro Pro Glu Pro Ser Ala Pro Phe Ile Glu
370                 375                 380
Pro Cys Gln Ala Thr Thr Ser Lys Ala Ala Ser Val Pro Ile Pro Val
385                 390                 395                 400
Ala Asp Ser Ile Pro Ala Lys Pro Gln Ala Ala Glu Ala Val Ser Asn
                405                 410                 415
Ile Ser Lys Ile Thr Asp Glu Ile Gln Lys Met Ser Val Ser Thr Pro
                420                 425                 430
Asn Gly Asn Leu Ser Leu Glu Glu Asn Arg Gln Leu Lys Asp Ala
            435                 440                 445
Arg Leu Cys Lys Val Cys Leu Asp Glu Glu Val Gly Val Val Phe Leu
450                 455                 460
Pro Cys Gly His Leu Ala Thr Cys Asn Gln Cys Ala Pro Ser Val Ala
465                 470                 475                 480
Asn Cys Pro Met Cys Arg Ala Asp Ile Lys Gly Phe Val Arg Thr Phe
                485                 490                 495
Leu Ser
```

(2) INFORMATION FOR SEQ ID NO:14:

(i) SEQUENCE CHARACTERISTICS:
        (A) LENGTH: 67 amino acids
        (B) TYPE: amino acid
        (C) STRANDEDNESS: Not Relevant
        (D) TOPOLOGY: both (ii) MOLECULE TYPE: protein (xi) SEQUENCE DESCRIPTION: SEQ ID NO:14:

```
Glu Glu Val Arg Leu Asn Thr Phe Glu Lys Trp Pro Val Ser Phe Leu
1               5                   10                  15

Ser Pro Glu Thr Met Ala Lys Asn Gly Phe Tyr Tyr Leu Gly Arg Ser
            20                  25                  30

Asp Glu Val Arg Cys Ala Phe Cys Lys Val Glu Ile Met Arg Trp Lys
        35                  40                  45

Glu Gly Glu Asp Pro Ala Ala Asp His Lys Lys Trp Ala Pro Gln Cys
    50                  55                  60

Pro Phe Val
65
```

(2) INFORMATION FOR SEQ ID NO:15:

(i) SEQUENCE CHARACTERISTICS:
        (A) LENGTH: 67 amino acids
        (B) TYPE: amino acid
        (C) STRANDEDNESS: Not Relevant
        (D) TOPOLOGY: both (ii) MOLECULE TYPE: protein (xi) SEQUENCE DESCRIPTION: SEQ ID NO:15:

```
Glu Ala Asn Arg Leu Val Thr Phe Lys Asp Trp Pro Asn Pro Asn Ile
1               5                   10                  15

Thr Pro Gln Ala Leu Ala Lys Ala Gly Phe Tyr Tyr Leu Asn Arg Leu
            20                  25                  30

Asp His Val Lys Cys Val Trp Cys Asn Gly Val Ile Ala Lys Trp Glu
        35                  40                  45

Lys Asn Asp Asn Ala Phe Glu Glu His Lys Arg Phe Phe Pro Gln Cys
    50                  55                  60

Pro Arg Val
65
```

(2) INFORMATION FOR SEQ ID NO:16:

(i) SEQUENCE CHARACTERISTICS:
        (A) LENGTH: 68 amino acids
        (B) TYPE: amino acid
        (C) STRANDEDNESS: Not Relevant
        (D) TOPOLOGY: both (ii) MOLECULE TYPE: protein (xi) SEQUENCE DESCRIPTION: SEQ ID NO:16:

```
Glu Phe Asn Arg Leu Lys Thr Phe Ala Asn Phe Pro Ser Ser Ser Pro
1               5                   10                  15

Val Ser Ala Ser Thr Leu Ala Arg Ala Gly Phe Leu Tyr Thr Gly Glu
            20                  25                  30

Gly Asp Thr Val Gln Cys Phe Ser Cys His Ala Ala Ile Asp Arg Trp
        35                  40                  45

Gln Tyr Gly Asp Ser Ala Val Gly Arg His Arg Arg Ile Ser Pro Asn
```

```
            50                  55                  60
Cys Arg Phe Ile
 65

(2) INFORMATION FOR SEQ ID NO:17:

(i) SEQUENCE CHARACTERISTICS:
        (A) LENGTH: 68 amino acids
        (B) TYPE: amino acid
        (C) STRANDEDNESS: Not Relevant
        (D) TOPOLOGY: both (ii) MOLECULE TYPE: protein (xi) SEQUENCE DESCRIPTION: SEQ ID NO:17:

Glu Phe Asn Arg Leu Lys Thr Phe Ala Asn Phe Pro Ser Gly Ser Pro
 1               5                  10                  15

Val Ser Ala Ser Thr Leu Ala Arg Ala Gly Phe Leu Tyr Thr Gly Glu
            20                  25                  30

Gly Asp Thr Val Arg Cys Phe Ser Cys His Ala Ala Val Asp Arg Trp
        35                  40                  45

Gln Tyr Gly Asp Ser Ala Val Gly Arg His Arg Lys Val Ser Pro Asn
    50                  55                  60

Cys Arg Phe Ile
 65

(2) INFORMATION FOR SEQ ID NO:18:

(i) SEQUENCE CHARACTERISTICS:
        (A) LENGTH: 68 amino acids
        (B) TYPE: amino acid
        (C) STRANDEDNESS: Not Relevant
        (D) TOPOLOGY: both (ii) MOLECULE TYPE: protein (xi) SEQUENCE DESCRIPTION: SEQ ID NO:18:

Glu Leu Tyr Arg Met Ser Thr Tyr Ser Thr Phe Pro Ala Gly Val Pro
 1               5                  10                  15

Val Ser Glu Arg Ser Leu Ala Arg Ala Gly Phe Tyr Tyr Thr Gly Val
            20                  25                  30

Asn Asp Lys Val Lys Cys Phe Cys Cys Gly Leu Met Leu Asp Asn Trp
        35                  40                  45

Lys Arg Gly Asp Ser Pro Thr Glu Lys His Lys Lys Leu Tyr Pro Ser
    50                  55                  60

Cys Arg Phe Val
 65

(2) INFORMATION FOR SEQ ID NO:19:

(i) SEQUENCE CHARACTERISTICS:
        (A) LENGTH: 68 amino acids
        (B) TYPE: amino acid
        (C) STRANDEDNESS: Not Relevant
        (D) TOPOLOGY: both (ii) MOLECULE TYPE: protein (xi) SEQUENCE DESCRIPTION: SEQ ID NO:19:

Glu Leu Tyr Arg Met Ser Thr Tyr Ser Thr Phe Pro Ala Gly Val Pro
 1               5                  10                  15

Val Ser Glu Arg Ser Leu Ala Arg Ala Gly Phe Tyr Tyr Thr Gly Val
            20                  25                  30
```

Asn Asp Lys Val Lys Cys Phe Cys Cys Gly Leu Met Leu Asp Asn Trp
            35                  40                  45

Lys Leu Gly Asp Ser Pro Ile Gln Lys His Lys Gln Leu Tyr Pro Ser
            50                  55                  60

Cys Ser Phe Ile
65

(2) INFORMATION FOR SEQ ID NO:20:

(i) SEQUENCE CHARACTERISTICS:
         (A) LENGTH: 68 amino acids
         (B) TYPE: amino acid
         (C) STRANDEDNESS: Not Relevant
         (D) TOPOLOGY: both (ii) MOLECULE TYPE: protein (xi) SEQUENCE DESCRIPTION: SEQ ID NO:20:

Glu Glu Ala Arg Leu Lys Ser Phe Gln Asn Trp Pro Asp Tyr Ala His
1               5                   10                  15

Leu Thr Pro Arg Glu Leu Ala Ser Ala Gly Leu Tyr Tyr Thr Gly Ala
            20                  25                  30

Asp Asp Gln Val Gln Cys Phe Cys Cys Gly Gly Lys Leu Lys Asn Trp
            35                  40                  45

Glu Pro Cys Asp Arg Ala Trp Ser Glu His Arg Arg His Phe Pro Asn
            50                  55                  60

Cys Phe Phe Val
65

(2) INFORMATION FOR SEQ ID NO:21:

(i) SEQUENCE CHARACTERISTICS:
         (A) LENGTH: 68 amino acids
         (B) TYPE: amino acid
         (C) STRANDEDNESS: Not Relevant
         (D) TOPOLOGY: both (ii) MOLECULE TYPE: protein (xi) SEQUENCE DESCRIPTION: SEQ ID NO:21:

Glu Glu Ala Arg Leu Lys Ser Phe Gln Asn Trp Pro Asp Tyr Ala His
1               5                   10                  15

Leu Thr Pro Arg Glu Leu Ala Ser Ala Gly Leu Tyr Tyr Thr Gly Ile
            20                  25                  30

Gly Asp Gln Val Gln Cys Phe Cys Cys Gly Gly Lys Leu Lys Asn Trp
            35                  40                  45

Glu Pro Cys Asp Arg Ala Trp Ser Glu His Arg Arg His Phe Pro Asn
            50                  55                  60

Cys Phe Phe Val
65

(2) INFORMATION FOR SEQ ID NO:22:

(i) SEQUENCE CHARACTERISTICS:
         (A) LENGTH: 67 amino acids
         (B) TYPE: amino acid
         (C) STRANDEDNESS: Not Relevant
         (D) TOPOLOGY: both (ii) MOLECULE TYPE: protein (xi) SEQUENCE DESCRIPTION: SEQ ID NO:22:

-continued

```
Glu Asn Ala Arg Leu Leu Thr Phe Gln Thr Trp Pro Leu Thr Phe Leu
1               5                   10                  15

Ser Pro Thr Asp Leu Ala Arg Ala Gly Phe Tyr Tyr Ile Gly Pro Gly
            20                  25                  30

Asp Arg Val Ala Cys Phe Ala Cys Gly Gly Lys Leu Ser Asn Trp Glu
            35                  40                  45

Pro Lys Asp Asn Ala Met Ser Glu His Leu Arg His Phe Pro Lys Cys
        50                  55                  60

Pro Phe Ile
65
```

(2) INFORMATION FOR SEQ ID NO:23:

(i) SEQUENCE CHARACTERISTICS:
        (A) LENGTH: 67 amino acids
        (B) TYPE: amino acid
        (C) STRANDEDNESS: Not Relevant
        (D) TOPOLOGY: both (ii) MOLECULE TYPE: protein (xi) SEQUENCE DESCRIPTION: SEQ ID NO:23:

```
Glu Glu Ala Arg Phe Leu Thr Tyr His Met Trp Pro Leu Thr Phe Leu
1               5                   10                  15

Ser Pro Ser Glu Leu Ala Arg Ala Gly Phe Tyr Tyr Ile Gly Pro Gly
            20                  25                  30

Asp Arg Val Ala Cys Phe Ala Cys Gly Gly Lys Leu Ser Asn Trp Glu
            35                  40                  45

Pro Lys Asp Asp Ala Met Ser Glu His Arg Arg His Phe Pro Asn Cys
        50                  55                  60

Pro Phe Leu
65
```

(2) INFORMATION FOR SEQ ID NO:24:

(i) SEQUENCE CHARACTERISTICS:
        (A) LENGTH: 66 amino acids
        (B) TYPE: amino acid
        (C) STRANDEDNESS: Not Relevant
        (D) TOPOLOGY: both (ii) MOLECULE TYPE: protein (xi) SEQUENCE DESCRIPTION: SEQ ID NO:24:

```
Tyr Glu Ala Arg Ile Val Thr Phe Gly Thr Trp Ile Tyr Ser Val Asn
1               5                   10                  15

Lys Glu Gln Leu Ala Arg Ala Gly Phe Tyr Ala Leu Gly Glu Gly Asp
            20                  25                  30

Lys Val Lys Cys Phe His Cys Gly Gly Gly Leu Thr Asp Trp Lys Pro
            35                  40                  45

Ser Glu Asp Pro Trp Asp Gln His Ala Lys Cys Tyr Pro Gly Cys Lys
        50                  55                  60

Tyr Leu
65
```

(2) INFORMATION FOR SEQ ID NO:25:

(i) SEQUENCE CHARACTERISTICS:
        (A) LENGTH: 66 amino acids
        (B) TYPE: amino acid
        (C) STRANDEDNESS: Not Relevant
        (D) TOPOLOGY: both (ii) MOLECULE TYPE: protein (xi) SEQUENCE DESCRIPTION: SEQ ID NO:25:

```
Tyr Glu Ala Arg Ile Phe Thr Phe Gly Thr Trp Ile Tyr Ser Val Asn
1               5                   10                  15

Lys Glu Gln Leu Ala Arg Ala Gly Phe Tyr Ala Leu Gly Glu Gly Asp
                20                  25                  30

Lys Val Lys Cys Phe His Cys Gly Gly Gly Leu Thr Asp Trp Lys Pro
                35                  40                  45

Ser Glu Asp Pro Trp Glu Gln His Ala Lys Trp Tyr Pro Gly Cys Lys
                50                  55                  60

Tyr Leu
65
```

(2) INFORMATION FOR SEQ ID NO:26:

(i) SEQUENCE CHARACTERISTICS:
        (A) LENGTH: 68 amino acids
        (B) TYPE: amino acid
        (C) STRANDEDNESS: Not Relevant
        (D) TOPOLOGY: both (ii) MOLECULE TYPE: protein (xi) SEQUENCE DESCRIPTION: SEQ ID NO:26:

```
His Ala Ala Arg Phe Lys Thr Phe Phe Asn Trp Pro Ser Ser Val Leu
1               5                   10                  15

Val Asn Pro Glu Gln Leu Ala Ser Ala Gly Phe Tyr Tyr Val Gly Asn
                20                  25                  30

Ser Asp Asp Val Lys Cys Phe Cys Cys Asp Gly Gly Leu Arg Cys Trp
                35                  40                  45

Glu Ser Gly Asp Asp Pro Trp Val Gln His Ala Lys Trp Phe Pro Arg
                50                  55                  60

Cys Glu Tyr Leu
65
```

(2) INFORMATION FOR SEQ ID NO:27:

(i) SEQUENCE CHARACTERISTICS:
        (A) LENGTH: 68 amino acids
        (B) TYPE: amino acid
        (C) STRANDEDNESS: Not Relevant
        (D) TOPOLOGY: both (ii) MOLECULE TYPE: protein (xi) SEQUENCE DESCRIPTION: SEQ ID NO:27:

```
His Ala Ala Arg Met Arg Thr Phe Met Tyr Trp Pro Ser Ser Val Pro
1               5                   10                  15

Val Gln Pro Glu Gln Leu Ala Ser Ala Gly Phe Tyr Tyr Val Gly Arg
                20                  25                  30

Asn Asp Asp Val Lys Cys Phe Gly Cys Asp Gly Gly Leu Arg Cys Trp
                35                  40                  45

Glu Ser Gly Asp Asp Pro Trp Val Glu His Ala Lys Trp Phe Pro Arg
                50                  55                  60

Cys Glu Phe Leu
65
```

(2) INFORMATION FOR SEQ ID NO:28:

(i) SEQUENCE CHARACTERISTICS:
            (A) LENGTH: 68 amino acids
            (B) TYPE: amino acid
            (C) STRANDEDNESS: Not Relevant
            (D) TOPOLOGY: both (ii) MOLECULE TYPE: protein (xi) SEQUENCE DESCRIPTION: SEQ ID NO:28:

Glu Ala Ala Arg Leu Arg Thr Phe Ala Glu Trp Pro Arg Gly Leu Lys
1               5                   10                  15

Gln Arg Pro Glu Glu Leu Ala Glu Ala Gly Phe Phe Tyr Thr Gly Gln
            20                  25                  30

Gly Asp Lys Thr Arg Cys Phe Cys Cys Asp Gly Gly Leu Lys Asp Trp
        35                  40                  45

Glu Pro Asp Asp Ala Pro Trp Gln Gln His Ala Arg Trp Tyr Asp Arg
    50                  55                  60

Cys Glu Tyr Val
65

(2) INFORMATION FOR SEQ ID NO:29:

(i) SEQUENCE CHARACTERISTICS:
            (A) LENGTH: 68 amino acids
            (B) TYPE: amino acid
            (C) STRANDEDNESS: Not Relevant
            (D) TOPOLOGY: both (ii) MOLECULE TYPE: protein (xi) SEQUENCE DESCRIPTION: SEQ ID NO:29:

Glu Ala Ala Arg Val Lys Ser Phe His Asn Trp Pro Arg Cys Met Lys
1               5                   10                  15

Gln Arg Pro Glu Gln Met Ala Asp Ala Gly Phe Phe Tyr Thr Gly Tyr
            20                  25                  30

Gly Asp Asn Thr Lys Cys Phe Tyr Cys Asp Gly Gly Leu Lys Asp Trp
        35                  40                  45

Glu Pro Glu Asp Val Pro Trp Glu Gln His Val Arg Trp Phe Asp Arg
    50                  55                  60

Cys Ala Tyr Val
65

(2) INFORMATION FOR SEQ ID NO:30:

(i) SEQUENCE CHARACTERISTICS:
            (A) LENGTH: 68 amino acids
            (B) TYPE: amino acid
            (C) STRANDEDNESS: Not Relevant
            (D) TOPOLOGY: both (ii) MOLECULE TYPE: protein (xi) SEQUENCE DESCRIPTION: SEQ ID NO:30:

Val Asp Ala Arg Leu Arg Thr Phe Thr Asp Trp Pro Ile Ser Asn Ile
1               5                   10                  15

Gln Pro Ala Ser Ala Leu Ala Gln Ala Gly Leu Tyr Tyr Gln Lys Ile
            20                  25                  30

Gly Asp Gln Val Arg Cys Phe His Cys Asn Ile Gly Leu Arg Ser Trp
        35                  40                  45

Gln Lys Glu Asp Glu Pro Trp Phe Glu His Ala Lys Trp Ser Pro Lys
    50                  55                  60

Cys Gln Phe Val (2) INFORMATION FOR SEQ ID NO:31:

(i) SEQUENCE CHARACTERISTICS:
        (A) LENGTH: 66 amino acids
        (B) TYPE: amino acid
        (C) STRANDEDNESS: Not Relevant
        (D) TOPOLOGY: both (ii) MOLECULE TYPE: protein (xi) SEQUENCE DESCRIPTION: SEQ ID NO:31:

Glu Ser Val Arg Leu Ala Thr Phe Gly Glu Trp Pro Leu Asn Ala Pro
1               5                   10                  15

Val Ser Ala Glu Asp Leu Val Ala Asn Gly Phe Phe Gly Thr Trp Met
            20                  25                  30

Glu Ala Glu Cys Asp Phe Cys His Val Arg Ile Asp Arg Trp Glu Tyr
        35                  40                  45

Gly Asp Leu Val Ala Glu Arg His Arg Ser Ser Pro Ile Cys Ser
    50                  55                  60

Met Val
65

(2) INFORMATION FOR SEQ ID NO:32:

(i) SEQUENCE CHARACTERISTICS:
        (A) LENGTH: 46 amino acids
        (B) TYPE: amino acid
        (C) STRANDEDNESS: Not Relevant
        (D) TOPOLOGY: both (ii) MOLECULE TYPE: protein (xi) SEQUENCE DESCRIPTION: SEQ ID NO:32:

Glu Gln Leu Arg Arg Leu Gln Glu Glu Arg Thr Cys Lys Val Cys Met
1               5                   10                  15

Asp Lys Glu Val Ser Val Val Phe Ile Pro Cys Gly His Leu Val Val
            20                  25                  30

Cys Gln Glu Cys Ala Pro Ser Leu Arg Lys Cys Pro Ile Cys
        35                  40                  45

(2) INFORMATION FOR SEQ ID NO:33:

(i) SEQUENCE CHARACTERISTICS:
        (A) LENGTH: 46 amino acids
        (B) TYPE: amino acid
        (C) STRANDEDNESS: Not Relevant
        (D) TOPOLOGY: both (ii) MOLECULE TYPE: protein (xi) SEQUENCE DESCRIPTION: SEQ ID NO:33:

Glu Gln Leu Arg Arg Leu Pro Glu Glu Arg Thr Cys Lys Val Cys Met
1               5                   10                  15

Asp Lys Glu Val Ser Ile Val Phe Ile Pro Cys Gly His Leu Val Val
            20                  25                  30

Cys Lys Asp Cys Ala Pro Ser Leu Arg Lys Cys Pro Ile Cys
        35                  40                  45

(2) INFORMATION FOR SEQ ID NO:34:

(i) SEQUENCE CHARACTERISTICS:
        (A) LENGTH: 46 amino acids (B) TYPE: amino acid
            (C) STRANDEDNESS: Not Relevant
            (D) TOPOLOGY: both (ii) MOLECULE TYPE: protein (xi) SEQUENCE DESCRIPTION: SEQ ID NO:34:

Glu Gln Leu Arg Arg Leu Gln Glu Glu Lys Leu Ser Lys Ile Cys Met
1               5                   10                  15

Asp Arg Asn Ile Ala Ile Val Phe Phe Pro Cys Gly His Leu Ala Thr
            20                  25                  30

Cys Lys Gln Cys Ala Glu Ala Val Asp Lys Cys Pro Met Cys
            35                  40                  45

(2) INFORMATION FOR SEQ ID NO:35:

(i) SEQUENCE CHARACTERISTICS:
            (A) LENGTH: 46 amino acids
            (B) TYPE: amino acid
            (C) STRANDEDNESS: Not Relevant
            (D) TOPOLOGY: both (ii) MOLECULE TYPE: protein (xi) SEQUENCE DESCRIPTION: SEQ ID NO:35:

Glu Gln Leu Arg Arg Leu Gln Glu Glu Lys Leu Cys Lys Ile Cys Met
1               5                   10                  15

Asp Arg Asn Ile Ala Ile Val Phe Val Pro Cys Gly His Leu Val Thr
            20                  25                  30

Cys Lys Gln Cys Ala Glu Ala Val Asp Lys Cys Pro Met Cys
            35                  40                  45

(2) INFORMATION FOR SEQ ID NO:36:

(i) SEQUENCE CHARACTERISTICS:
            (A) LENGTH: 46 amino acids
            (B) TYPE: amino acid
            (C) STRANDEDNESS: Not Relevant
            (D) TOPOLOGY: both (ii) MOLECULE TYPE: protein (xi) SEQUENCE DESCRIPTION: SEQ ID NO:36:

Glu Glu Asn Arg Gln Leu Lys Asp Ala Arg Leu Cys Lys Val Cys Leu
1               5                   10                  15

Asp Glu Glu Val Gly Val Val Phe Leu Pro Cys Gly His Leu Ala Thr
            20                  25                  30

Cys Asn Gln Cys Ala Pro Ser Val Ala Asn Cys Pro Met Cys
            35                  40                  45

(2) INFORMATION FOR SEQ ID NO:37:

(i) SEQUENCE CHARACTERISTICS:
            (A) LENGTH: 46 amino acids
            (B) TYPE: amino acid
            (C) STRANDEDNESS: Not Relevant
            (D) TOPOLOGY: both (ii) MOLECULE TYPE: protein (xi) SEQUENCE DESCRIPTION: SEQ ID NO:37:

Glu Lys Glu Pro Gln Val Glu Asp Ser Lys Leu Cys Lys Ile Cys Tyr
1               5                   10                  15

Val Glu Glu Cys Ile Val Cys Phe Val Pro Cys Gly His Val Val Ala
            20                  25                  30

```
          Cys Ala Lys Cys Ala Leu Ser Val Asp Lys Cys Pro Met Cys
                   35                  40                  45

(2) INFORMATION FOR SEQ ID NO:38:

(i) SEQUENCE CHARACTERISTICS:
        (A) LENGTH: 46 amino acids
        (B) TYPE: amino acid
        (C) STRANDEDNESS: Not Relevant
        (D) TOPOLOGY: both (ii) MOLECULE TYPE: protein (xi) SEQUENCE DESCRIPTION: SEQ ID NO:38:

Ala Val Glu Ala Glu Val Ala Asp Asp Arg Leu Cys Lys Ile Cys Leu
  1               5                  10                  15

Gly Ala Glu Lys Thr Val Cys Phe Val Pro Cys Gly His Val Val Ala
                 20                  25                  30

Cys Gly Lys Cys Ala Ala Gly Val Thr Thr Cys Pro Val Cys
                 35                  40                  45

(2) INFORMATION FOR SEQ ID NO:39:

(i) SEQUENCE CHARACTERISTICS:
        (A) LENGTH: 2474 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:39:

GAATTCCGGG AGACCTACAC CCCCGGAGAT CAGAGGTCAT TGCTGGCGTT CAGAGCCTAG      60

GAAGTGGGCT GCGGTATCAG CCTAGCAGTA AAACCGACCA GAAGCCATGC ACAAAACTAC    120

ATCCCCAGAG AAAGACTTGT CCCTTCCCCT CCCTGTCATC TCACCATGAA CATGGTTCAA    180

GACAGCGCCT TTCTAGCCAA GCTGATGAAG AGTGCTGACA CCTTTGAGTT GAAGTATGAC    240

TTTTCCTGTG AGCTGTACCG ATTGTCCACG TATTCAGCTT TTCCCAGGGG AGTTCCTGTG    300

TCAGAAAGGA GTCTGGCTCG TGCTGGCTTT TACTACACTG GTGCCAATGA CAAGGTCAAG    360

TGCTTCTGCT GTGGCCTGAT GCTAGACAAC TGGAAACAAG GGACAGTCC CATGGAGAAG     420

CACAGAAAGT TGTACCCCAG CTGCAACTTT GTACAGACTT TGAATCCAGC CAACAGTCTG    480

GAAGCTAGTC CTCGGCCTTC TCTTCCTTCC ACGGCGATGA GCACCATGCC TTTGAGCTTT    540

GCAAGTTCTG AGAATACTGG CTATTTCAGT GGCTCTTACT CGAGCTTTCC CTCAGACCCT    600

GTGAACTTCC GAGCAAATCA AGATTGTCCT GCTTTGAGCA CAAGTCCCTA CCACTTTGCA    660

ATGAACACAG AGAAGGCCAG ATTACTCACC TATGAAACAT GGCCATTGTC TTTTCTGTCA    720

CCAGCAAAGC TGGCCAAAGC AGGCTTCTAC TACATAGGAC CTGGAGATAG AGTGGCCTGC    780

TTTGCGTGCG ATGGGAAACT GAGCAACTGG GAACGTAAGG ATGATGCTAT GTCAGAGCAC    840

CAGAGGCATT TCCCCAGCTG TCCGTTCTTA AAAGACTTGG GTCAGTCTGC TTCGAGATAC    900

ACTGTCTCTA ACCTGAGCAT GCAGACACAC GCAGCCCGTA TTAGAACATT CTCTAACTGG    960

CCTTCTAGTG CACTAGTTCA TTCCCAGGAA CTTGCAAGTG CGGGCTTTTA TTATACAGGA   1020

CACAGTGATG ATGTCAAGTG TTTATGCTGT GATGGTGGGC TGAGGTGCTG GGAATCTGGA   1080

GATGACCCCT GGGTGGAACA TGCCAAGTGG TTTCCAAGGT GTGAGTACTT GCTCAGAATC   1140

AAAGGCCAAG AATTTGTCAG CCAAGTTCAA GCTGGCTATC CTCATCTACT TGAGCAGCTA   1200
```

-continued

```
TTATCTACGT CAGACTCCCC AGAAGATGAG AATGCAGACG CAGCAATCGT GCATTTTGGC    1260

CCTGGAGAAA GTTCGGAAGA TGTCGTCATG ATGAGCACGC CTGTGGTTAA AGCAGCCTTG    1320

GAAATGGGCT TCAGTAGGAG CCTGGTGAGA CAGACGGTTC AGTGGCAGAT CCTGGCCACT    1380

GGTGAGAACT ACAGGACCGT CAGTGACCTC GTTATAGGCT TACTCGATGC AGAAGACGAG    1440

ATGAGAGAGG AGCAGATGGA GCAGGCGGCC GAGGAGGAGG AGTCAGATGA TCTAGCACTA    1500

ATCCGGAAGA ACAAAATGGT GCTTTTCCAA CATTTGACGT GTGTGACACC AATGCTGTAT    1560

TGCCTCCTAA GTGCAAGGGC CATCACTGAA CAGGAGTGCA ATGCTGTGAA ACAGAAACCA    1620

CACACCTTAC AAGCAAGCAC ACTGATTGAT ACTGTGTTAG CAAAAGGAAA CACTGCAGCA    1680

ACCTCATTCA GAAACTCCCT TCGGGAAATT GACCCTGCGT TATACAGAGA TATATTTGTG    1740

CAACAGGACA TTAGGAGTCT TCCCACAGAT GACATTGCAG CTCTACCAAT GGAAGAACAG    1800

TTGCGGCCCC TCCCGGAGGA CAGAATGTGT AAAGTGTGTA TGGACCGAGA GGTATCCATC    1860

GTGTTCATTC CCTGTGGCCA TCTGGTCGTG TGCAAAGACT GCGCTCCCTC TCTGAGGAAG    1920

TGTCCCATCT GTAGAGGGAC CATCAAGGGC ACAGTGCGCA CATTTCTCTC CTGAACAAGA    1980

CTAATGGTCC ATGGCTGCAA CTTCAGCCAG GAGGAAGTTC ACTGTCACTC CCAGTTCCAT    2040

TCGGAACTTG AGGCCAGCCT GGATAGCACG AGACACCGCC AAACACACAA ATATAAACAT    2100

GAAAAACTTT TGTCTGAAGT CAAGAATGAA TGAATTACTT ATATAATAAT TTTAATTGGT    2160

TTCCTTAAAA GTGCTATTTG TTCCCAACTC AGAAAATTGT TTTCTGTAAA CATATTTACA    2220

TACTACCTGC ATCTAAAGTA TTCATATATT CATATATTCA GATGTCATGA GAGAGGGTTT    2280

TGTTCTTGTT CCTGAAAAGC TGGTTTATCA TCTGATCAGC ATATACTGCG CAACGGGCAG    2340

GGCTAGAATC CATGAACCAA GCTGCAAAGA TCTCACGCTA ATAAGGCGG AAAGATTTGG     2400

AGAAACGAAA GGAATTCTT TCCTGTCCAA TGTATACTCT TCAGACTAAT GACCTCTTCC     2460

TATCAAGCCT TCTA                                                      2474
```

(2) INFORMATION FOR SEQ ID NO:40:

(i) SEQUENCE CHARACTERISTICS:
        (A) LENGTH: 602 amino acids
        (B) TYPE: amino acid
        (C) STRANDEDNESS: Not Relevant
        (D) TOPOLOGY: linear (ii) MOLECULE TYPE: protein (xi) SEQUENCE DESCRIPTION: SEQ ID NO:40:

```
Met Asn Met Val Gln Asp Ser Ala Phe Leu Ala Lys Leu Met Lys Ser
1               5                   10                  15

Ala Asp Thr Phe Glu Leu Lys Tyr Asp Phe Ser Cys Glu Leu Tyr Arg
            20                  25                  30

Leu Ser Thr Tyr Ser Ala Phe Pro Arg Gly Val Pro Val Ser Glu Arg
        35                  40                  45

Ser Leu Ala Arg Ala Gly Phe Tyr Tyr Thr Gly Ala Asn Asp Lys Val
    50                  55                  60

Lys Cys Phe Cys Cys Gly Leu Met Leu Asp Asn Trp Lys Gln Gly Asp
65                  70                  75                  80

Ser Pro Met Glu Lys His Arg Lys Leu Tyr Pro Ser Cys Asn Phe Val
                85                  90                  95

Gln Thr Leu Asn Pro Ala Asn Ser Leu Glu Ala Ser Pro Arg Pro Ser
            100                 105                 110

Leu Pro Ser Thr Ala Met Ser Thr Met Pro Leu Ser Phe Ala Ser Ser
```

```
            115                 120                 125
Glu Asn Thr Gly Tyr Phe Ser Gly Ser Tyr Ser Ser Phe Pro Ser Asp
            130                 135                 140
Pro Val Asn Phe Arg Ala Asn Gln Asp Cys Pro Ala Leu Ser Thr Ser
145                 150                 155                 160
Pro Tyr His Phe Ala Met Asn Thr Glu Lys Ala Arg Leu Leu Thr Tyr
                165                 170                 175
Glu Thr Trp Pro Leu Ser Phe Leu Ser Pro Ala Lys Leu Ala Lys Ala
            180                 185                 190
Gly Phe Tyr Tyr Ile Gly Pro Gly Asp Arg Val Ala Cys Phe Ala Cys
            195                 200                 205
Asp Gly Lys Leu Ser Asn Trp Glu Arg Lys Asp Asp Ala Met Ser Glu
            210                 215                 220
His Gln Arg His Phe Pro Ser Cys Pro Phe Leu Lys Asp Leu Gly Gln
225                 230                 235                 240
Ser Ala Ser Arg Tyr Thr Val Ser Asn Leu Ser Met Gln Thr His Ala
                245                 250                 255
Ala Arg Ile Arg Thr Phe Ser Asn Trp Pro Ser Ser Ala Leu Val His
                260                 265                 270
Ser Gln Glu Leu Ala Ser Ala Gly Phe Tyr Tyr Thr Gly His Ser Asp
            275                 280                 285
Asp Val Lys Cys Leu Cys Cys Asp Gly Gly Leu Arg Cys Trp Glu Ser
            290                 295                 300
Gly Asp Asp Pro Trp Val Glu His Ala Lys Trp Phe Pro Arg Cys Glu
305                 310                 315                 320
Tyr Leu Leu Arg Ile Lys Gly Gln Glu Phe Val Ser Gln Val Gln Ala
                325                 330                 335
Gly Tyr Pro His Leu Leu Glu Gln Leu Leu Ser Thr Ser Asp Ser Pro
                340                 345                 350
Glu Asp Glu Asn Ala Asp Ala Ala Ile Val His Phe Gly Pro Gly Glu
            355                 360                 365
Ser Ser Glu Asp Val Val Met Met Ser Thr Pro Val Val Lys Ala Ala
370                 375                 380
Leu Glu Met Gly Phe Ser Arg Ser Leu Val Arg Gln Thr Val Gln Trp
385                 390                 395                 400
Gln Ile Leu Ala Thr Gly Glu Asn Tyr Arg Thr Val Ser Asp Leu Val
                405                 410                 415
Ile Gly Leu Leu Asp Ala Glu Asp Glu Met Arg Glu Gln Met Glu
            420                 425                 430
Gln Ala Ala Glu Glu Glu Ser Asp Asp Leu Ala Leu Ile Arg Lys
            435                 440                 445
Asn Lys Met Val Leu Phe Gln His Leu Thr Cys Val Thr Pro Met Leu
450                 455                 460
Tyr Cys Leu Leu Ser Ala Arg Ala Ile Thr Glu Gln Glu Cys Asn Ala
465                 470                 475                 480
Val Lys Gln Lys Pro His Thr Leu Gln Ala Ser Thr Leu Ile Asp Thr
                485                 490                 495
Val Leu Ala Lys Gly Asn Thr Ala Thr Ser Phe Arg Asn Ser Leu
            500                 505                 510
Arg Glu Ile Asp Pro Ala Leu Tyr Arg Asp Ile Phe Val Gln Gln Asp
            515                 520                 525
Ile Arg Ser Leu Pro Thr Asp Ile Ala Ala Leu Pro Met Glu Glu
530                 535                 540
```

```
Gln Leu Arg Pro Leu Pro Glu Asp Arg Met Cys Lys Val Cys Met Asp
545                 550                 555                 560

Arg Glu Val Ser Ile Val Phe Ile Pro Cys Gly His Leu Val Cys
                565                 570                 575

Lys Asp Cys Ala Pro Ser Leu Arg Lys Cys Pro Ile Cys Arg Gly Thr
            580                 585                 590

Ile Lys Gly Thr Val Arg Thr Phe Leu Ser
595                 600
```

(2) INFORMATION FOR SEQ ID NO:41:

(i) SEQUENCE CHARACTERISTICS:
        (A) LENGTH: 2416 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:41:

```
CTGTGGTGGA GATCTATTGT CCAAGTGGTG AGAAACTTCA TCTGGAAGTT TAAGCGGTCA      60

GAAATACTAT TACTACTCAT GGACAAAACT GTCTCCCAGA GACTCGCCCA AGGTACCTTA     120

CACCCAAAAA CTTAAACGTA AATGGAGAA GAGCACAATC TTGTCAAATT GGACAAAGGA     180

GAGCGAAGAA AAAATGAAGT TTGACTTTTC GTGTGAACTC TACCGAATGT CTACATATTC     240

AGCTTTTCCC AGGGGAGTTC CTGTCTCAGA GAGGAGTCTG GCTCGTGCTG GCTTTTATTA     300

TACAGGTGTG AATGACAAAG TCAAGTGCTT CTGCTGTGGC CTGATGTTGG ATAACTGGAA     360

ACAAGGGGAC AGTCCTGTTG AAAAGCACAG ACAGTTCTAT CCCAGCTGCA GCTTTGTACA     420

GACTCTGCTT TCAGCCAGTC TGCAGTCTCC ATCTAAGAAT ATGTCTCCTG TGAAAAGTAG     480

ATTTGCACAT TCGTCACCTC TGGAACGAGG TGGCATTCAC TCCAACCTGT GCTCTAGCCC     540

TCTTAATTCT AGAGCAGTGG AAGACTTCTC ATCAAGGATG GATCCCTGCA GCTATGCCAT     600

GAGTACAGAA GAGGCCAGAT TCTTACTTA CAGTATGTGG CCTTTAAGTT TTCTGTCACC     660

AGCAGAGCTG GCCAGAGCTG GCTTCTATTA CATAGGGCCT GGAGACAGGG TGGCCTGTTT     720

TGCCTGTGGT GGGAAACTGA GCAACTGGGA ACCAAAGGAT TATGCTATGT CAGAGCACCG     780

CAGACATTTT CCCCACTGTC CATTTCTGGA AAATACTTCA GAAACACAGA GGTTTAGTAT     840

ATCAAATCTA AGTATGCAGA CACACTCTGC TCGATTGAGG ACATTTCTGT ACTGGCCACC     900

TAGTGTTCCT GTTCAGCCCG AGCAGCTTGC AAGTGCTGGA TTCTATTACG TGGATCGCAA     960

TGATGATGTC AAGTGCCTTT GTTGTGATGG TGGCTTGAGA TGTTGGGAAC CTGGAGATGA    1020

CCCCTGGATA GAACACGCCA AATGGTTTCC AAGGTGTGAG TTCTTGATAC GGATGAAGGG    1080

TCAGGAGTTT GTTGATGAGA TTCAAGCTAG ATATCCTCAT CTTCTTGAGC AGCTGTTGTC    1140

CACTTCAGAC ACCCCAGGAG AAGAAAATGC TGACCCTACA GAGACAGTGG TGCATTTTGG    1200

CCCTGGAGAA AGTTCGAAAG ATGTCGTCAT GATGAGCACG CCTGTGGTTA AGCAGCCTTT    1260

GGAAATGGGC TTCAGTAGGA GCCTGGTGAG ACAGACGGTT CAGCGGCAGA TCCTGGCCAC    1320

TGGTGAGAAC TACAGGACCG TCAATGATAT TGTCTCAGTA CTTTTGAATG CTGAAGATGA    1380

GAGAAGAGAA GAGGAGAAGG AAAGACAGAC TGAAGAGATG GCATCAGGTG ACTTATCACT    1440

GATTCGGAAG AATAGAATGG CCCTCTTTCA ACAGTTGACA CATGTCCTTC CTATCCTGGA    1500

TAATCTTCTT GAGGCCAGTG TAATTACAAA ACAGGAACAT GATATTATTA GACAGAAAAC    1560

ACAGATACCC TTACAAGCAA GAGAGCTTAT TGACACCGTT TTAGTCAAGG GAAATGCTGC    1620
```

```
AGCCAACATC TTCAAAAACT CTCTGAAGGG AATTGACTCC ACGTTATATG AAAACTTATT    1680

TGTGGAAAAG AATATGAAGT ATATTCCAAC AGAAGACGTT TCAGGCTTGT CATTGGAAGA    1740

GCAGTTGCGG AGATTACAAG AAGAACGAAC TTGCAAAGTG TGTATGGACA GAGAGGTTTC    1800

TATTGTGTTC ATTCCGTGTG GTCATCTAGT AGTCTGCCAG GAATGTGCCC CTTCTCTAAG    1860

GAAGTGCCCC ATCTGCAGGG GGACAATCAA GGGGACTGTG CGCACATTTC TCTCATGAGT    1920

GAAGAATGGT CTGAAAGTAT TGTTGGACAT CAGAAGCTGT CAGAACAAAG AATGAACTAC    1980

TGATTTCAGC TCTTCAGCAG GACATTCTAC TCTCTTTCAA GATTAGTAAT CTTGCTTTAT    2040

GAAGGGTAGC ATTGTATATT TAAGCTTAGT CTGTTGCAAG GGAAGGTCTA TGCTGTTGAG    2100

CTACAGGACT GTGTCTGTTC CAGAGCAGGA GTTGGGATGC TTGCTGTATG TCCTTCAGGA    2160

CTTCTTGGGA TTTGGGAATT TGGGGAAAGC TTTGGAATCC AGTGATGTGG AGCTCAGAAA    2220

TCCTGGAACC AGTGACTCTG GTACTCAGTA GATAGGGTAC CCTGTACTTC TTGGTGCTTT    2280

TCCAGTCTGG GAAATAAGGA GGAATCTGCT GCTGGTAAAA ATTTGCTGGA TGTGAGAAAT    2340

AGATGAAAGT GTTTCGGGTG GGGGCGTGCA TCAGTGTAGT GTGTGCAGGG ATGTATGCAG    2400

GCCAAACACT GTGTAG                                                   2416

(2) INFORMATION FOR SEQ ID NO:42:

(i) SEQUENCE CHARACTERISTICS:
        (A) LENGTH: 591 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:42:

Met Glu Lys Ser Thr Ile Leu Ser Asn Trp Thr Lys Glu Ser Glu Glu
1               5                   10                  15

Lys Met Lys Phe Asp Phe Ser Cys Glu Leu Tyr Arg Met Ser Thr Tyr
            20                  25                  30

Ser Ala Phe Pro Arg Gly Val Pro Val Ser Glu Arg Ser Leu Ala Arg
        35                  40                  45

Ala Gly Phe Tyr Tyr Thr Gly Val Asn Asp Lys Val Lys Cys Phe Cys
    50                  55                  60

Cys Gly Leu Met Leu Asp Asn Trp Lys Gln Gly Asp Ser Pro Val Glu
65                  70                  75                  80

Lys His Arg Gln Phe Tyr Pro Ser Cys Ser Phe Val Gln Thr Leu Leu
                85                  90                  95

Ser Ala Ser Leu Gln Ser Pro Ser Lys Asn Met Ser Pro Val Lys Ser
            100                 105                 110

Arg Phe Ala His Ser Ser Pro Leu Glu Arg Gly Ile His Ser Asn
        115                 120                 125

Leu Cys Ser Ser Pro Leu Asn Ser Arg Ala Val Glu Asp Phe Ser Ser
    130                 135                 140

Arg Met Asp Pro Cys Ser Tyr Ala Met Ser Thr Glu Glu Ala Arg Phe
145                 150                 155                 160

Leu Thr Tyr Ser Met Trp Pro Leu Ser Phe Leu Ser Pro Ala Glu Leu
                165                 170                 175

Ala Arg Ala Gly Phe Tyr Tyr Ile Gly Pro Gly Asp Arg Val Ala Cys
            180                 185                 190

Phe Ala Cys Gly Gly Lys Leu Ser Asn Trp Glu Pro Lys Asp Tyr Ala
```

-continued

```
                195                 200                 205
Met Ser Glu His Arg Arg His Phe Pro His Cys Pro Phe Leu Glu Asn
    210                 215                 220
Thr Ser Glu Thr Gln Arg Phe Ser Ile Ser Asn Leu Ser Met Gln Thr
225                 230                 235                 240
His Ser Ala Arg Leu Arg Thr Phe Leu Tyr Trp Pro Ser Val Pro
                245                 250                 255
Val Gln Pro Glu Gln Leu Ala Ser Ala Gly Phe Tyr Tyr Val Asp Arg
            260                 265                 270
Asn Asp Asp Val Lys Cys Leu Cys Cys Asp Gly Gly Leu Arg Cys Trp
            275                 280                 285
Glu Pro Gly Asp Asp Pro Trp Ile Glu His Ala Lys Trp Phe Pro Arg
    290                 295                 300
Cys Glu Phe Leu Ile Arg Met Lys Gly Gln Glu Phe Val Asp Glu Ile
305                 310                 315                 320
Gln Ala Arg Tyr Pro His Leu Leu Glu Gln Leu Leu Ser Thr Ser Asp
                325                 330                 335
Thr Pro Gly Glu Glu Asn Ala Asp Pro Thr Glu Thr Val Val His Phe
            340                 345                 350
Gly Pro Gly Glu Ser Ser Lys Asp Val Val Met Met Ser Thr Pro Val
            355                 360                 365
Val Lys Ala Ala Leu Glu Met Gly Phe Ser Arg Ser Leu Val Arg Gln
    370                 375                 380
Thr Val Gln Arg Gln Ile Leu Ala Thr Gly Glu Asn Tyr Arg Thr Val
385                 390                 395                 400
Asn Asp Ile Val Ser Val Leu Leu Asn Ala Glu Asp Glu Arg Arg Glu
                405                 410                 415
Glu Glu Lys Glu Arg Gln Thr Glu Glu Met Ala Ser Gly Asp Leu Ser
            420                 425                 430
Leu Ile Arg Lys Asn Arg Met Ala Leu Phe Gln Gln Leu Thr His Val
            435                 440                 445
Leu Pro Ile Leu Asp Asn Leu Leu Glu Ala Ser Val Ile Thr Lys Gln
    450                 455                 460
Glu His Asp Ile Ile Arg Gln Lys Thr Gln Ile Pro Leu Gln Ala Arg
465                 470                 475                 480
Glu Leu Ile Asp Thr Val Leu Val Lys Gly Asn Ala Ala Ala Asn Ile
                485                 490                 495
Phe Lys Asn Ser Leu Lys Gly Ile Asp Ser Thr Leu Tyr Glu Asn Leu
            500                 505                 510
Phe Val Glu Lys Asn Met Lys Tyr Ile Pro Thr Glu Asp Val Ser Gly
            515                 520                 525
Leu Ser Leu Glu Glu Gln Leu Arg Arg Leu Gln Glu Glu Arg Thr Cys
    530                 535                 540
Lys Val Cys Met Asp Arg Glu Val Ser Ile Val Phe Ile Pro Cys Gly
545                 550                 555                 560
His Leu Val Val Cys Gln Glu Cys Ala Pro Ser Leu Arg Lys Cys Pro
                565                 570                 575
Ile Cys Arg Gly Thr Ile Lys Gly Thr Val Arg Thr Phe Leu Ser
            580                 585                 590
```

(2) INFORMATION FOR SEQ ID NO:43:

(i) SEQUENCE CHARACTERISTICS:
        (A) LENGTH: 11 amino acids (B) TYPE: amino acid
                    (C) STRANDEDNESS: single
                    (D) TOPOLOGY: linear (ii) MOLECULE TYPE: protein (xi) SEQUENCE DESCRIPTION: SEQ ID NO:43:

Met Glu Gln Lys Leu Ile Ser Glu Glu Asp Leu
1               5                   10

(2) INFORMATION FOR SEQ ID NO:44:

(i) SEQUENCE CHARACTERISTICS:
          (A) LENGTH: 635 amino acids
          (B) TYPE: amino acid
          (C) STRANDEDNESS: single
          (D) TOPOLOGY: linear (ii) MOLECULE TYPE: protein (ix) FEATURE:
          (A) NAME/KEY: Other
          (B) LOCATION: 1...1
          (D) OTHER INFORMATION: Xaa at 1,2,3 and 635 can be any amino
                  acid or may be abse (xi) SEQUENCE DESCRIPTION: SEQ ID NO:44:

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Phe Xaa Glu Xaa Xaa Arg
            20                  25                  30

Leu Xaa Thr Phe Xaa Xaa Phe Pro Xaa Xaa Xaa Pro Val Ser Xaa Xaa
            35                  40                  45

Xaa Leu Ala Arg Ala Gly Phe Xaa Tyr Thr Gly Xaa Xaa Asp Xaa Val
    50                  55                  60

Xaa Cys Phe Xaa Cys Xaa Xaa Xaa Asp Xaa Trp Xaa Xaa Gly Asp
65                  70                  75                  80

Ser Xaa Xaa Xaa Xaa His Xaa Xaa Xaa Xaa Pro Xaa Cys Xaa Phe Ile
            85                  90                  95

Xaa Xaa Xaa Xaa Xaa Xaa Xaa Xaa Xaa Xaa Xaa Xaa Xaa Xaa Xaa
            100                 105                 110

Xaa Xaa Xaa Xaa Xaa Xaa Xaa Xaa Xaa Xaa Ser Xaa Xaa Xaa Xaa
            115                 120                 125

Xaa Xaa Xaa Xaa Xaa Xaa Xaa Xaa Xaa Tyr Xaa Xaa Xaa Xaa Xaa
            130                 135                 140

Xaa Xaa Xaa Xaa Xaa Arg Xaa Xaa Glu Xaa Xaa Xaa Xaa Xaa Xaa
145                 150                 155                 160

Xaa Xaa Xaa Xaa Xaa Asp Xaa Ser Asp Xaa Xaa Xaa Xaa Xaa Xaa
            165                 170                 175

Xaa Xaa Xaa Met Xaa Xaa Glu Glu Ala Arg Leu Xaa Thr Phe Xaa Xaa
            180                 185                 190

Trp Pro Xaa Xaa Xaa Xaa Leu Xaa Pro Xaa Glu Leu Ala Xaa Ala Gly
            195                 200                 205

Phe Tyr Tyr Xaa Gly Xaa Xaa Asp Xaa Val Xaa Cys Phe Xaa Cys Gly
210                 215                 220

Gly Lys Leu Xaa Asn Trp Glu Pro Xaa Asp Xaa Ala Xaa Ser Glu His
225                 230                 235                 240

Xaa Arg His Phe Pro Xaa Cys Pro Phe Val Xaa Xaa Xaa Xaa Xaa
            245                 250                 255

Xaa Xaa Xaa Xaa Xaa Xaa Xaa Xaa Xaa Xaa Xaa Xaa Xaa Phe Xaa Xaa

```
              260                 265                 270
Ser Xaa Xaa Pro Xaa Asn Pro Xaa Met Ala Xaa Xaa Xaa Ala (ii) MOLECULE TYPE: cDNA (ix) FEATURE:
        (A) NAME/KEY: Coding Sequence
        (B) LOCATION: 1...0
        (D) OTHER INFORMATION:

(xi) SEQUENCE DESCRIPTION: SEQ ID NO:45:

GAGTTTAATA GATTAAAAAC TTTTGCTAAT TTTCCAAGTG GTAGTCCTGT TTCAGCATCA    60

ACACTGGCAC GAGCAGGGTT TCTTTATACT GGTGAAGGAG ATACCGTGCG GTGCTTTAGT    120

TGTCATGCAG CTGTAGATAG ATGGCAATAT GGAGACTCAG CAGTTGGAAG ACACAGGAAA    180

GTATCCCCAA ATTGCAGATT TATC                                          204

(2) INFORMATION FOR SEQ ID NO:46:

(i) SEQUENCE CHARACTERISTICS:
        (A) LENGTH: 204 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:46:

GAAGAAGCTA GATTAAAGTC CTTTCAGAAC TGGCCAGACT ATGCTCACCT AACCCCAAGA    60

GAGTTAGCAA GTGCTGGACT CTACTACACA GGTATTGGTG ACCAAGTGCA GTGCTTTTGT    120

TGTGGTGGAA AACTGAAAAA TTGGGAACCT TGTGATCGTG CCTGGTCAGA ACACAGGCGA    180

CACTTTCCTA ATTGCTTCTT TGTT                                          204

(2) INFORMATION FOR SEQ ID NO:47:

(i) SEQUENCE CHARACTERISTICS:
        (A) LENGTH: 198 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:47:

TATGAAGCAC GGATCTTTAC TTTTGGGACA TGGATATACT CAGTTAACAA GGAGCAGCTT    60

GCAAGAGCTG GATTTTATGC TTTAGGTGAA GGTGATAAAG TAAAGTGCTT TCACTGTGGA    120

GGAGGGCTAA CTGATTGGAA GCCCAGTGAA GACCCTTGGG AACAACATGC TAAATGGTAT    180

CCAGGGTGCA AATATCTG                                                 198

(2) INFORMATION FOR SEQ ID NO:48:

(i) SEQUENCE CHARACTERISTICS:
        (A) LENGTH: 138 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:48:

GAGCAGCTAA GGCGCCTGCA AGAGGAGAAG CTTTGCAAAA TCTGTATGGA TAGAAATATT    60

GCTATCGTTT TTGTTCCTTG TGGACATCTA GTCACTTGTA AACAATGTGC TGAAGCAGTT    120

GACAAGTGTC CCATGTGC                                                 138

(2) INFORMATION FOR SEQ ID NO:49:

(i) SEQUENCE CHARACTERISTICS:
        (A) LENGTH: 204 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:49:

```
GAGTTTAATA GATTAAAAAC ATTTGCTAAC TTCCCAAGTA GTAGTCCTGT TTCAGCATCA      60

ACATTGGCGC GAGCTGGGTT TCTTTATACC GGTGAAGGAG ACACCGTGCA ATGTTTCAGT     120

TGTCATGCGG CAATAGATAG ATGGCAGTAT GGAGACTCAG CTGTTGGAAG ACACAGGAGA     180

ATATCCCCAA ATTGCAGATT TATC                                            204
```

(2) INFORMATION FOR SEQ ID NO:50:

(i) SEQUENCE CHARACTERISTICS:
        (A) LENGTH: 204 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:50:

```
GAAGAAGCCA GATTGAAGTC ATTTCAGAAC TGGCCGGACT ATGCTCATTT AACCCCCAGA      60

GAGTTAGCTA GTGCTGGCCT CTACTACACA GGGGCTGATG ATCAAGTGCA ATGCTTTTGT     120

TGTGGGGGAA AACTGAAAAA TTGGGAACCC TGTGATCGTG CCTGGTCAGA ACACAGGAGA     180

CACTTTCCCA ATTGCTTTTT TGTT                                            204
```

(2) INFORMATION FOR SEQ ID NO:51:

(i) SEQUENCE CHARACTERISTICS:
        (A) LENGTH: 198 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:51:

```
TATGAAGCAC GGATCGTTAC TTTTGGAACA TGGATATACT CAGTTAACAA GGAGCAGCTT      60

GCAAGAGCTG GATTTTATGC TTTAGGTGAA GGCGATAAAG TGAAGTGCTT CCACTGTGGA     120

GGAGGGCTCA CGGATTGGAA GCCAAGTGAA GACCCCTGGG ACCAGCATGC TAAGTGCTAC     180

CCAGGGTGCA AATACCTA                                                   198
```

(2) INFORMATION FOR SEQ ID NO:52:

(i) SEQUENCE CHARACTERISTICS:
        (A) LENGTH: 138 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:52:

```
GAGCAGCTAA GGCGCCTACA AGAGGAGAAG CTTTCCAAAA TCTGTATGGA TAGAAATATT      60

GCTATCGTTT TTTTTCCTTG TGGACATCTG GCCACTTGTA AACAGTGTGC AGAAGCAGTT     120
```

```
GACAAATGTC CCATGTGC                                                    138
```

(2) INFORMATION FOR SEQ ID NO:53:

(i) SEQUENCE CHARACTERISTICS:
        (A) LENGTH: 204 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:53:

```
GAACTGTACC GAATGTCTAC GTATTCCACT TTTCCTGCTG GGGTTCCTGT CTCAGAAAGG        60

AGTCTTGCTC GTGCTGGTTT CTATTACACT GGTGTGAATG ACAAGGTCAA ATGCTTCTGT       120

TGTGGCCTGA TGCTGGATAA CTGGAAAAGA GGAGACAGTC CTACTGAAAA GCATAAAAAG       180

TTGTATCCTA GCTGCAGATT CGTT                                             204
```

(2) INFORMATION FOR SEQ ID NO:54:

(i) SEQUENCE CHARACTERISTICS:
        (A) LENGTH: 201 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:54:

```
GAAAATGCCA GATTACTTAC TTTTCAGACA TGGCCATTGA CTTTTCTGTC GCCAACAGAT        60

CTGGCACGAG CAGGCTTTTA CTACATAGGA CCTGGAGACA GAGTGGCTTG CTTTGCCTGT       120

GGTGGAAAAT TGAGCAATTG GGAACCGAAG GATAATGCTA TGTCAGAACA CCTGAGACAT       180

TTTCCCAAAT GCCCATTTAT A                                                201
```

(2) INFORMATION FOR SEQ ID NO:55:

(i) SEQUENCE CHARACTERISTICS:
        (A) LENGTH: 204 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:55:

```
CATGCAGCCC GCTTTAAAAC ATTCTTTAAC TGGCCCTCTA GTGTTCTAGT TAATCCTGAG        60

CAGCTTGCAA GTGCGGGTTT TTATTATGTG GGTAACAGTG ATGATGTCAA ATGCTTTTGC       120

TGTGATGGTG GACTCAGGTG TTGGGAATCT GGAGATGATC CATGGGTTCA ACATGCCAAG       180

TGGTTTCCAA GGTGTGAGTA CTTG                                             204
```

(2) INFORMATION FOR SEQ ID NO:56:

(i) SEQUENCE CHARACTERISTICS:
        (A) LENGTH: 138 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:56:

GAACAATTGC GGAGACTACC AGAAGAAAGA ACATGTAAAG TGTGTATGGA CAAAGAAGTG        60

TCCATAGTGT TTATTCCTTG TGGTCATCTA GTAGTATGCA AAGATTGTGC TCCTTCTTTA       120

AGAAAGTGTC CTATTTGT                                                    138

(2) INFORMATION FOR SEQ ID NO:57:

(i) SEQUENCE CHARACTERISTICS:
        (A) LENGTH: 203 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:57:

AGCTGTACCG ATTGTCCACG TATTCAGCTT TTCCCAGGGG AGTTCCTGTG TCAGAAAGGA        60

GTCTGGCTCG TGCTGGCTTT TACTACACTG GTGCCAATGA CAAGGTCAAG TGCTTCTGCT       120

GTGGCCTGAT GCTAGACAAC TGGAAACAAG GGACAGTCC CATGGAGAAG CACAGAAAGT       180

TGTACCCCAG CTGCAACTTT GTA                                              203

(2) INFORMATION FOR SEQ ID NO:58:

(i) SEQUENCE CHARACTERISTICS:
        (A) LENGTH: 201 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:58:

GAGAAGGCCA GATTACTCAC CTATGAAACA TGGCCATTGT CTTTTCTGTC ACCAGCAAAG        60

CTGGCCAAAG CAGGCTTCTA CTACATAGGA CCTGGAGATA GAGTGGCCTG CTTTGCGTGC       120

GATGGGAAAC TGAGCAACTG GAACGTAAG GATGATGCTA TGTCAGAGCA CCAGAGGCAT       180

TTCCCCAGCT GTCCGTTCTT A                                                201

(2) INFORMATION FOR SEQ ID NO:59:

(i) SEQUENCE CHARACTERISTICS:
        (A) LENGTH: 204 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:59:

CACGCAGCCC GTATTAGAAC ATTCTCTAAC TGGCCTTCTA GTGCACTAGT TCATTCCCAG        60

GAACTTGCAA GTGCGGGCTT TTATTATACA GGACACAGTG ATGATGTCAA GTGTTTATGC       120

TGTGATGGTG GGCTGAGGTG CTGGGAATCT GGAGATGACC CCTGGGTGGA ACATGCCAAG       180

TGGTTTCCAA GGTGTGAGTA CTTG                                             204

(2) INFORMATION FOR SEQ ID NO:60:

(i) SEQUENCE CHARACTERISTICS:
        (A) LENGTH: 138 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:60:

```
GAACAGTTGC GGCCCCTCCC GGAGGACAGA ATGTGTAAAG TGTGTATGGA CCGAGAGGTA      60

TCCATCGTGT TCATTCCCTG TGGCCATCTG GTCGTGTGCA AAGACTGCGC TCCCTCTCTG     120

AGGAAGTGTC CCATCTGT                                                   138
```

(2) INFORMATION FOR SEQ ID NO:61:

(i) SEQUENCE CHARACTERISTICS:
        (A) LENGTH: 204 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:61:

```
GAACTCTACA GAATGTCTAC ATATTCAACT TTCCCCGCCG GGGTGCCTGT CTCAGAAAGG      60

AGTCTTGCTC GTGCTGGTTT TTATTATACT GGTGTGAATG ACAAGGTCAA ATGCTTCTGT     120

TGTGGCCTGA TGCTGGATAA CTGGAAACTA GGAGACAGTC CTATTCAAAA GCATAAACAG     180

CTATATCCTA GCTGTAGCTT TATT                                            204
```

(2) INFORMATION FOR SEQ ID NO:62:

(i) SEQUENCE CHARACTERISTICS:
        (A) LENGTH: 201 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:62:

```
GAAGAAGCCA GATTTCTTAC CTACCATATG TGGCCATTAA CTTTTTTGTC ACCATCAGAA      60

TTGGCAAGAG CTGGTTTTTA TTATATAGGA CCTGGAGATA GGGTAGCCTG CTTTGCCTGT     120

GGTGGGAAGC TCAGTAACTG GGAACCAAAG GATGATGCTA TGTCAGAACA CCGGAGGCAT     180

TTTCCCAACT GTCCATTTTT G                                               201
```

(2) INFORMATION FOR SEQ ID NO:63:

(i) SEQUENCE CHARACTERISTICS:
        (A) LENGTH: 204 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:63:

```
CATGCAGCTC GAATGAGAAC ATTTATGTAC TGGCCATCTA GTGTTCCAGT TCAGCCTGAG      60

CAGCTTGCAA GTGCTGGTTT TTATTATGTG GGTCGCAATG ATGATGTCAA ATGCTTTGGT     120

TGTGATGGTG GCTTGAGGTG TTGGGAATCT GGAGATGATC CATGGGTAGA ACATGCCAAG     180

TGGTTTCCAA GGTGTGAGTT CTTG                                            204
```

(2) INFORMATION FOR SEQ ID NO:64:

(i) SEQUENCE CHARACTERISTICS:
        (A) LENGTH: 138 base pairs
        (B) TYPE: nucleic acid
        (C) STRANDEDNESS: single (D) TOPOLOGY: linear (ii) MOLECULE TYPE: cDNA (xi) SEQUENCE DESCRIPTION: SEQ ID NO:64:

GAACAATTGA GGAGGTTGCA AGAAGAACGA ACTTGTAAAG TGTGTATGGA CAAAGAAGTT    60

TCTGTTGTAT TTATTCCTTG TGGTCATCTG GTAGTATGCC AGGAATGTGC CCCTTCTCTA   120

AGAAAATGCC CTATTTGC                                                138

(2) INFORMATION FOR SEQ ID NO:65:

(i) SEQUENCE CHARACTERISTICS:
            (A) LENGTH: 204 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:65:

GAACTCTACC GAATGTCTAC ATATTCAGCT TTTCCCAGGG GAGTTCCTGT CTCAGAGAGG    60

AGTCTGGCTC GTGCTGGCTT TTATTATACA GGTGTGAATG ACAAAGTCAA GTGCTTCTGC   120

TGTGGCCTGA TGTTGGATAA CTGGAAACAA GGGGACAGTC CTGTTGAAAA GCACAGACAG   180

TTCTATCCCA GCTGCAGCTT TGTA                                         204

(2) INFORMATION FOR SEQ ID NO:66:

(i) SEQUENCE CHARACTERISTICS:
            (A) LENGTH: 201 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:66:

GAAGAGGCCA GATTTCTTAC TTACAGTATG TGGCCTTTAA GTTTTCTGTC ACCAGCAGAG    60

CTGGCCAGAG CTGGCTTCTA TTACATAGGG CCTGGAGACA GGGTGGCCTG TTTTGCCTGT   120

GGTGGGAAAC TGAGCAACTG GAACCAAAG GATTATGCTA TGTCAGAGCA CCGCAGACAT    180

TTTCCCCACT GTCCATTTCT G                                            201

(2) INFORMATION FOR SEQ ID NO:67:

(i) SEQUENCE CHARACTERISTICS:
            (A) LENGTH: 204 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:67:

CACTCTGCTC GATTGAGGAC ATTTCTGTAC TGGCCACCTA GTGTTCCTGT TCAGCCCGAG    60

CAGCTTGCAA GTGCTGGATT CTATTACGTG GATCGCAATG ATGATGTCAA GTGCCTTTGT   120

TGTGATGGTG GCTTGAGATG TTGGGAACCT GGAGATGACC CCTGGATAGA ACACGCCAAA   180

TGGTTTCCAA GGTGTGAGTT CTTG                                         204

(2) INFORMATION FOR SEQ ID NO:68:

(i) SEQUENCE CHARACTERISTICS:

-continued

```
        (A) LENGTH: 114 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:68:

GAACGAACTT GCAAAGTGTG TATGGACAGA GAGGTTTCTA TTGTGTTCAT TCCGTGTGGT          60

CATCTAGTAG TCTGCCAGGA ATGTGCCCCT TCTCTAAGGA AGTGCCCCAT CTGC              114
```